US009624546B2

(12) United States Patent
Sampson et al.

(10) Patent No.: US 9,624,546 B2
(45) Date of Patent: Apr. 18, 2017

(54) SCREENING METHODS AND SEQUENCES RELATING THERETO

(75) Inventors: Julian R. Sampson, Llandaff (GB); Jeremy Peter Cheadle, Bichgrove (GB)

(73) Assignee: Myriad Genetics, Inc., Salt Lake City, UT (US)

(*) Notice: Subject to any disclaimer, the term of this patent is extended or adjusted under 35 U.S.C. 154(b) by 1849 days.

(21) Appl. No.: 12/572,121

(22) Filed: Oct. 1, 2009

(65) Prior Publication Data

US 2010/0028900 A1 Feb. 4, 2010

Related U.S. Application Data

(62) Division of application No. 12/048,728, filed on Mar. 14, 2008, now Pat. No. 7,622,258, which is a division of application No. 10/485,999, filed as application No. PCT/GB02/03591 on Aug. 2, 2002, now Pat. No. 7,405,283.

(30) Foreign Application Priority Data

Aug. 3, 2001 (GB) .................................. 01189950

(51) Int. Cl.
C12Q 1/68 (2006.01)
(52) U.S. Cl.
CPC ..... *C12Q 1/6886* (2013.01); *C12Q 2600/156* (2013.01); *C12Q 2600/172* (2013.01)
(58) Field of Classification Search
None
See application file for complete search history.

(56) References Cited

U.S. PATENT DOCUMENTS

| 6,013,473 | A | 1/2000 | Wei |
| 6,051,222 | A | 4/2000 | Wei |
| 6,060,594 | A | 5/2000 | English et al. |
| 6,639,063 | B1 | 10/2003 | Edwards et al. |
| 7,405,283 | B2 * | 7/2008 | Sampson et al. ............ 536/23.1 |
| 7,622,258 | B2 * | 11/2009 | Sampson et al. ............ 435/6.18 |

FOREIGN PATENT DOCUMENTS

WO       WO 97/33903    *  9/1997

OTHER PUBLICATIONS

Dove et al (Cancer Surv, 1995, 25: Abstract).*
Shinmura et al (Cancer letters, May 2001, 166:65-69).*
Al-Tassan et al., "Inherited variants of MYH associated with somatic G:C→T:A mutations in colorectal tumors", *Nature Genetics*, Feb. 2002, 30:227-232.
Audebert et al., "Effect of single mutations in the *OGG1* gene found in human tumors on the substrate specificity of the Ogg1 protein", *Nucleic Acids Research*, Jul. 2000, 28(14):2672-2678.
Boiteux et al., "The Human OGG1 Gene: Structure, Functions, and Its Implication in the Process of Carcinogenesis", *Archives of Biochemistry and Biophysics*, May 1, 2000, 377(1):1-8.
Fearnhead et al., "The ABC of APC", *Human Molecular Genetics*, Apr. 2001, 10(7):721-733.

Gu et al., "Differential DNA recognition and glycosylase activity of the native human MutY homolog (hMYH) and recombinant hMYH expressed in bacteria", *Nucleic Acids Research*, Jun. 2001, 29(12):2666-2674.
Jones et al., "Biallelic germline mutations in MYH predispose to multiple colorectal adenoma and somatic G:C→: A mutations", *Human Molecular Genetics*, Nov. 1, 2002, 11(23):2961-2967.
Nakabeppu, "Molecular genetics and structural biology of human MutT homolog, MTH1", *Mutation Research*, Jun. 2001, 477(1-2):59-70.
Ohtsubo et al., "Identification of human MutY homolog (hMYH) as a repair enzyme for 2-hydroxyadenine in DNA and detection of multiple forms of hMYH located in nuclei and mitochondria", *Nucleic Acids Research*, Mar. 2000, 28(6):1355-1364.
Shinmura et al., "Infrequent mutations of the hOGG1 gene, that is involved in the excision of 8-hydroxyguanine in damaged DNA, in human gastric cancer", *Japan Journal of Cancer Research*, Aug. 1998, 89(8):825-828.
Shinmura et al., "Somatic mutations and single nucleotide polymorphisms of base exicision repair genes involved in the repair of 8-hydroxyguanine in damaged DNA", *Cancer Letters*, May 10, 2001, 166(1):65-69.
Slupska et al., "Cloning and Sequencing a Human Homolog (hMYH) of the *Escherichia coli* mutY Gene Whose Function is Required for the Repair of Oxidative DNA Damage", *Journal of Bacteriology*, Jul. 1996, 178(13):3885-3892.
Sugimura et al., "hOGG1 Ser326Cys polymorphism and lung cancer susceptibility", *Cancer Epidemiol. Biomarkers Prev.*, Aug. 1999, 8(8):669-674.
Stratagene Catalog, 1997/1998, p. 118.
Tsuzuki et al., "Analysis of MTH1 gene function in mice with targeted mutagenesis", *Mutation Research*, Jun. 2, 2001, 477(1-2):71-78.
Wikman et al., "hOGG1 polymorphism and loss of heterozygosity (LOH): Significance for lung cancer susceptibility in a Caucasian population", *Cancer Genetics*, Dec. 15, 2000, 88(6):932-937.
Kundu, Sucharita et al., "Adenine Removal Activity and Bacterial Complementation with the human MutY homologue (MUTYH) and Y165C, G382D, P391L and Q324R variants associated with colorectal cancer", DNA Repair, 8(12), Dec. 3, 2009, pp. 1-29.
Pope, Mary Ann et al., "Insight into the functional consequences of hMYH variants associated with colorectal cancer: distinct differences in the adenine glycosylase activity and the response to AP endonucleases of Y150C and G365D murine MYH", DNA Repair, 4, Jul. 29, 2004, pp. 315-325.
Office Action dated Mar. 3, 2010 issued in corresponding Canadian application No. 2,454,766.
Response to Office Action dated Feb. 25, 2011 filed in corresponding Canadian application No. 2,454,766.
Office Action dated Jun. 22, 2011 issued in corresponding Canadian application No. 2,454,766.
Response to Office Action dated Dec. 6, 2011 filed in corresponding Canadian application No. 2,454,766.
Restriction Requirement dated Sep. 23, 2005 issued in corresponding U.S. Appl. No. 10/485,999.

* cited by examiner

*Primary Examiner* — Sean Aeder
(74) *Attorney, Agent, or Firm* — Myriad Genetics, Inc. IP Department

(57) ABSTRACT

Disclosed are screening methods and sequences related thereto. Disclosed are methods for detecting mutations in the MYH gene of an individual. Also disclosed are methods of genotyping and methods of predicting for an individual the likelihood of developing certain cancers, such as colorectal cancer.

12 Claims, 8 Drawing Sheets

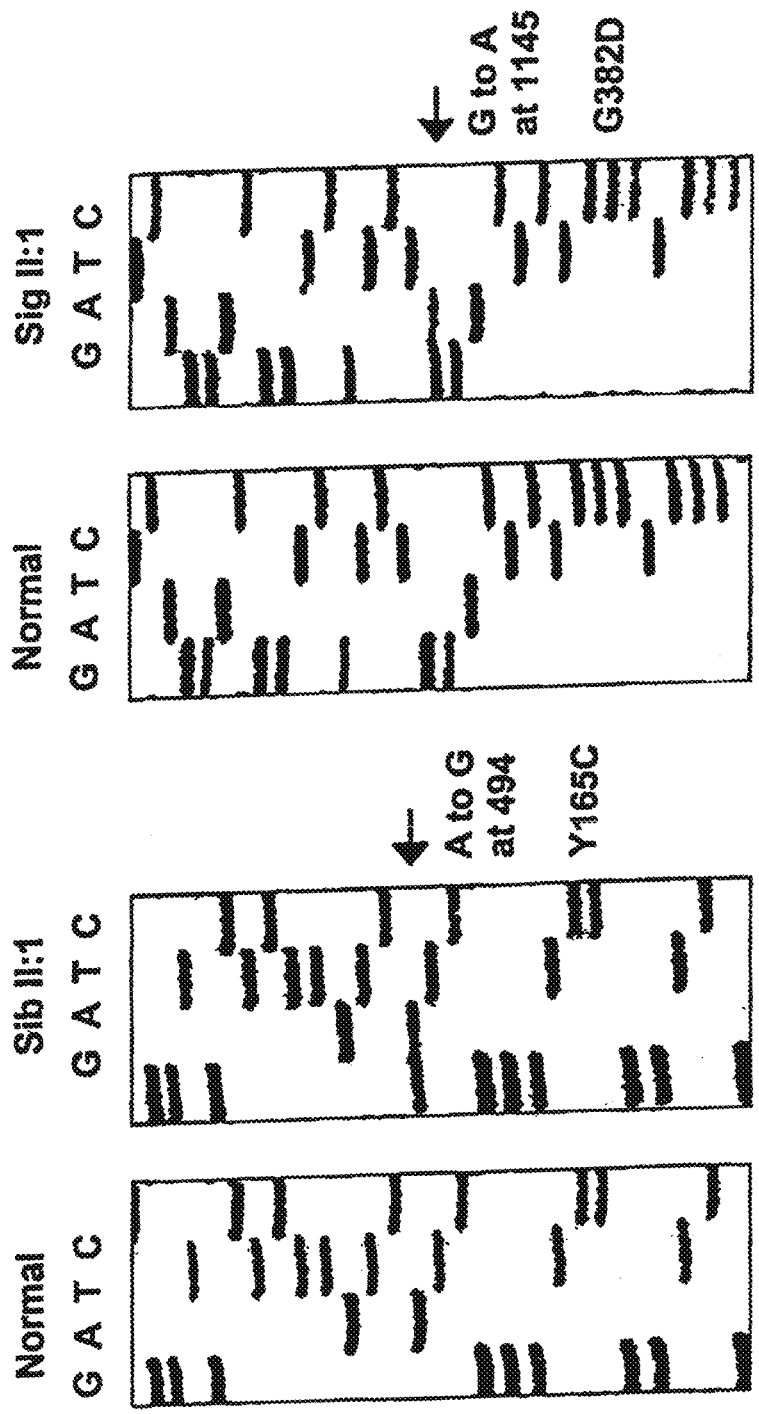

SCREENING METHODS AND SEQUENCES RELATING THERETO

CROSS-REFERENCE TO RELATED APPLICATIONS

This application is a divisional of U.S. application Ser. No. 10/485,999, filed Jul. 14, 2004, now U.S. Pat. No. 7,405,283 (hereinafter the "'283 patent"), and is with U.S. application Ser. No. 12/048,728, filed Mar. 14, 2008, now U.S. Pat. No. 7,622,258, which is also a divisional of the '283 patent; the '283 patent in turn claims the benefit of PCT/GB02/03591, filed Aug. 2, 2002; which claims the benefit of Great Britain application serial no. 01189950, dated Aug. 3, 2001, which are all hereby incorporated by reference in their entirety.

SEQUENCE LISTING

The instant application was filed with a formal Sequence Listing submitted electronically as a text file. This text file, which was named "3004-00-2D-2009-09-30-SEQ-LIST ST25.txt", was created on Sep. 30, 2009, and is 53,365 bytes in size. Its contents are incorporated by reference herein in their entirety.

FIELD OF THE INVENTION

The present invention relates to inherited variations in genes believed to be involved in base excision repair (BER) pathways of humans; to their use in screening patients for defects in BER and thereby for cancers or predisposition to cancers. The invention further relates to screening methods using the variations, and to a diagnostic kit for use in the screening methods.

BACKGROUND OF THE INVENTION

BER pathways play a major role in the repair of mutations caused by reactive oxygen species that are generated during aerobic metabolism, as described in Nature 362, 709-715 (1993). Oxidative DNA damage has been implicated in the aetiology of degenerative diseases, ageing and cancer (Mutat. Res. 250, 3116 (1991), but evidence linking inherited deficiencies of BER to these diseases has been lacking.

8-Oxo-7,8-dihydrodeoxyguanine (8-oxoG), the most stable product of oxidative DNA damage, is highly mutagenic, since it readily mispairs with A residues (Nature 349, 431-434 (1991)), leading to an increased frequency of spontaneous G:C→T:A transversion mutations in repair-deficient bacteria and yeast cells. In E. coli, three enzymes, mutM, mutY and mutT, function synergistically to protect cells from the deleterious effects of guanine oxidation (J. Bacteriol. 174, 6321-6325 (1992)). The mutM DNA glycosylase removes the oxidised base from 8-oxoG:C base pairs in duplex DNA; the mutY DNA glycosylase excises A misincorporated opposite unrepaired 8-oxoG during replication; and mutT is an 8-oxo-dGTPase preventing incorporation of 8-oxo-dGMP into nascent DNA. Human mutM, mutY and mutT homologues have been identified and termed hOGG1 (Proc. Natl. Acad. Sci. (USA) 94, 8016-8020 (1997)), hMYH (J. Bactiol. 178, 3885-3892 (1996)) and hMTH (J. Biol. Chem. 268, 23524-23530 (1993)), respectively. Patent specification no. WO 97/33903 also discloses a human MutY polypeptide and DNA encoding it, together with its potential use in diagnosing a cancer or a susceptibility to a cancer.

Until now, inherited, as distinguished from somatic, defects of BER have not been associated with any human genetic disorder, although mutations of the Escherichia coli BER genes mutM and mutY lead to increased G:C→T:A transversions (Proc. Natl. Acad. Sci. (USA) 85, 2709-2713 (1988); J. Bacteriol. 174, 6321-6325 (1992); Mol. Gen. Genet. 239, 72-76 (1993); and Mol. Gen. Genet. 254, 171-178 (1997)).

SUMMARY OF THE INVENTION

We now provide evidence that inherited defects of human BER genes might also lead to increased spontaneous (somatic, as opposed to hereditary) G:C→T:A transversions in other genes, which control cellular growth and so predispose the individual to cancer. Such other genes include the APC gene, a known tumour suppressor gene for colorectal adenomas and carcinomas. Somatic mutations of APC have been found to occur in most such cancers. Accordingly, we further provide evidence that inherited defects in human BER genes can indicate a predisposition towards cancers in humans.

We studied a family (hereinafter, 'family N') having multiple colorectal adenomas and carcinoma, and excluded an inherited mutation of APC as is seen in familial adenomatous polyposis (FAP) (Hum Mol Genet 10 721-733 (2001)). Eleven tumours from three affected siblings contained eighteen somatic APC mutations. Fifteen were G:C→T:A transversions, a significantly greater proportion than reported in sporadic or FAP associated tumours. Analysis of hMYH revealed that the siblings were compound heterozygotes for the non-conservative missense variants, Y165C (an A to G substitution at nucleotide 494 in exon 7) and G382D (a G to A substitution at nucleotide 1145 in exon 13). G382D has been identified (by Shinmura K et al in Cancer Letters 166 65-69 (2001)) in lung cancer samples from the tumour itself; however, it was not identified as an inherited change that might be useful in the detection of predisposition towards lung (or any other) cancer.

These two changes affect residues that are conserved in E. coli mutY, namely, y82 and g253; y82 lies within the pseudo HhH motif and has been predicted to function in mismatch specificity (Nat Struct Biol 5 1058-1064 (1998)). Assays of adenine glycosylase activity of y82c and g253d mutants with a G:A substrate showed 90- and 6-fold reduction compared to wild type.

These data link the inherited variants in hMYH to the pattern of somatic APC mutation in family N and implicate defective BER in tumour predisposition in humans and other animals. Subsequent studies have revealed additional inherited variants in hMYH. Therefore, we have been able to provide the identity of such inherited variants and a screening method for identifying an individual having a predisposition towards having a cancer as a result of inherited variants in the genes involved in BER.

The present invention therefore provides a variant of hMYH, suitable for use in a screening method of the invention, comprising a polypeptide variant selected from:
  (i) Y165C, as defined herein [SEQ ID NO:1];
  (ii) E466X, as defined herein [SEQ ID NO:3]; and
  (iii) Y90X, as defined herein [SEQ ID NO:4].

The present invention further provides a nucleotide sequence corresponding to any one of the above polypeptide variations, being a nucleotide sequence encoding the polypeptide variant of this invention. Specifically, the nucleotide sequence encoding the polypeptide variants Y165C (SEQ ID NO:1), E466X (SEQ ID NO:3) and Y90X (SEQ ID NO:4)

are defined herein as SEQ ID NO:130, SEQ ID NO:131 and SEQ ID NO:132, respectively.

Accordingly, the present invention further provides a nucleotide sequence
(a) encoding a polypeptide variant according to the invention;
(b) a sequence substantially homologous to or that hybridises to sequence (a) under stringent conditions; or
(c) a sequence substantially homologous to or that hybridizes under stringent conditions to the sequence (a) or (b) but for the degeneracy of the genetic code; or
(d) an oligonucleotide specific for any of the sequences (a), (b) or (c).

Such homologous sequences as are referred to in (b) and (c) also display the functional and biological activity of the variation according to the invention. Preferably, such homologous sequences are at least 90% identical to the sequence (a).

Preferably, there is provided a variant of hMYH, comprising Y165C, or a nucleotide sequence encoding the polypeptide, as defined herein as SEQ ID NO:130.

Such polypeptide and corresponding nucleotide variants are herein collectively referred to as 'variations according to this invention'.

Accordingly, the present invention provides a method for diagnosing susceptibility to cancer comprising determining, from a sample derived from a patient, a mutation comprising a variation according to this invention. In particular, there is provided a screening method for identifying an individual having a pre-disposition towards having a cancer, which screening method comprises the steps of:
(a) obtaining a test sample comprising a nucleotide sequence comprised in a gene in a base excision repair (BER) pathway of the individual or an amino acid sequence of a polypeptide expressed thereby; and
(b) comparing a region of the test sample sequence with the corresponding region of the wild type sequence,
whereby a difference between the test sample sequence and the wild type sequence signifies that the individual is pre-disposed to having the cancer; and
wherein the difference comprises a variation according to this invention, or the known G382D-hMYH or the nucleotide sequence encoding it.

For example, where the variant polypeptide sequence is Y165C-hMYH, this means the human MYH protein in which the 165$^{th}$ amino acid (Y in the wild type) is replaced by C. The corresponding difference in the nucleotide sequence means the gene variant, which is the nucleotide sequence coding for the variant polypeptide (protein) sequence. In the case of Y165C-hMYH, the corresponding nucleotide variant is 494A→G-hMYH, which means the human MYH gene in which the 494$^{th}$ base (A in exon 7 in the wild type) is replaced by G, namely SEQ ID NO:130. However, the variant may also comprise the nucleotide sequence encoding the known G382D-hMYH; or the variant may comprise that encoding E466X-hMYH (1396G→T) or Y90X-hMYH (270C→A).

Preferably, the BER pathway gene is hMYH.

Preferably, in the screening method of the invention, the BER pathway gene is involved in the repair of another gene and protects against G:C→T:A transversion mutations in that gene. More preferably, these G:C→T:A transversion mutations occur at regions of the sequence wherein the G is followed by AA in the sequence and therefore comprise GAA→TAA mutations.

The invention therefore further provides an alternative screening method for identifying an individual having an inherited defect in a BER gene and/or hMYH and/or is pre-disposed to having a cancer, which screening method comprises the steps of:
(a) obtaining a test sample comprising a nucleotide sequence comprised in a marker gene of the individual or an amino acid sequence of a polypeptide expressed thereby, the marker gene being a marker for a disease or condition correlated with the presence of a defect in a BER gene and/or hMYH or cancer; and
(b) comparing a region of the test sample sequence with the following diagnostic sequence [SEQ ID NO: 2] or a peptide sequence encoded thereby:

5'-X-X1-A-A-X2-A-A-3'      [SEQ ID NO: 2]

wherein X is A or T; X1 is G or T; and X2 is G or A.
whereby identity between the region of the test sample sequence and the diagnostic sequence signifies that the individual has an inherited defect in a BER gene and/or hMYH and/or is pre-disposed to having the cancer.

Another aspect of the invention is a diagnostic sequence suitable for use in the alternative screening method, which sequence comprises:
(a)

5'-X-X1-A-A-X2-A-A-3'      [SEQ ID NO: 2]

wherein X is A or T; X1 is G or T; and X2 is G or A;
(b) a sequence substantially homologous to or that hybridises to sequence (a) under stringent conditions; or
(c) a sequence substantially homologous to or that hybridizes under stringent conditions to the sequence (a) or (b) but for the degeneracy of the genetic code; or
(d) an oligonucleotide specific for any of the sequences (a), (b) or (c).

Accordingly, this invention further provides for the use of:
(a) a diagnostic sequence according to the invention, or a polypeptide encoded thereby,
(b) a sequence substantially homologous to or that hybridises to nucleotide sequence (a) under stringent conditions; or
(c) a sequence substantially homologous to or that hybridizes under stringent conditions to the nucleotide sequence (a) or (b) but for the degeneracy of the genetic code; or
(d) an oligonucleotide specific for any of the sequences (a), (b) or (c)
in a therapeutic, diagnostic or detection method, especially for the determination of susceptibility to a disease, such as cancer.

Especially preferred is when the damaged gene is a known marker for the cancer, such as APC (a marker for bowel cancer).

Therefore, in the screening method according to the invention, the cancer is most preferably bowel cancer and/or the damaged gene is APC.

In accordance with the above findings, the present invention therefore still further provides for use of:
(a) a BER gene variant, or a polypeptide encoded thereby, selected from variants of this invention and the known G382D-hMYH or the nucleotide sequence encoding it;
(b) a sequence substantially homologous to or that hybridises to nucleotide sequence (a) under stringent conditions; or
(c) a sequence substantially homologous to or that hybridizes under stringent conditions to the nucleotide sequence (a) or (b) but for the degeneracy of the genetic code; or (d) an oligonucleotide specific for any of the sequences (a), (b) or (c) in a therapeutic, diagnostic or detection method.

Preferably, the BER gene is hMYH and therefore a preferred use is of:

(a) a variant of the hMYH gene, or the hMYH polypeptide encoded thereby, selected from variants of this invention and the known G382D-hMYH or the nucleotide sequence encoding it;
(b) a sequence substantially homologous to or that hybridises to nucleotide sequence (a) under stringent conditions; or
(c) a sequence substantially homologous to or that hybridizes under stringent conditions to the nucleotide sequence (a) or (b) but for the degeneracy of the genetic code; or
(d) an oligonucleotide specific for any of the sequences (a), (b) or (c) in a therapeutic, diagnostic or detection method.

A particularly preferred use is when the BER gene and/or hMYH is for the determination of susceptibility to a disease, such as cancer. Especially preferred is wherein the corresponding wild type BER pathway gene or wild type hMYH gene acts to protect against G:C→T:A transverse mutations in a cancer marker gene, such as APC.

The present invention further provides a kit suitable for use in carrying out the screening method of the invention, which kit comprises one or more of:
(a) an oligo- or poly-nucleotide having a nucleic acid sequence corresponding to a region of a variant BER gene, which region incorporates at least one variation from the corresponding wild-type sequence selected from a variation according to this invention;
(b) an oligo- or poly-nucleotide having a nucleic acid sequence corresponding to the wild-type sequence in the region specified in (a); and/or
(c) one or more reagents suitable for carrying out PCR for amplifying desired regions of the patient's DNA.

A kit suitable for use in carrying out an alternative screening method as described above comprises one or more of:
(a) an oligo- or poly-nucleotide comprising a diagnostic sequence as described herein, or an amino acid sequence encoded thereby;
(b) one or more reagents suitable for carrying out PCR for amplifying desired regions of the patient's DNA; and/or
(c) a 'surrogate marker' that is indicative of or correlated to the presence of a variant of a sequence (a).

Reagents for the kit may include, for example, PCR primers corresponding to the exon of the BER gene, hMYH or a diagnostic sequence according to the invention; and/or primers mentioned herein; and/or other reagents for use in PCR, such as Taq DNA polymerase.

Preferably, any oligonucleotides in the kit comprise in the range of from 5 to 25 base-pairs, such as 10-20 base-pairs for the variant sequences. In any case, the oligonucleotides must be selected so as to be unique for the region selected and not repeated elsewhere in the genome.

Since, in the situation where it is desired to screen for multiple variations, such as in the range of from 15 to 20 or more, a kit comprising up to 40 oligo- or poly-nucleotides or more would be required, in the alternative screening method, therefore, using DNA chip technology, the present invention provides a plurality of oligo- or poly-nucleotides as defined in kit component (a) above immobilised on a solid support.

Other nucleotide detection methods could be used, such as signal amplification methods being pioneered in nanotechnology (such as Q-Dots). Also, single molecule detection methods could be employed (such as STM). In which case, the kit according to this invention may comprise one or more reagents for use in such alternative methods.

Further, suitable, alternative screening methods according to this invention may further comprise obtaining a test sample comprising a BER variant (eg a protein/peptide sequence comprising a variation of hMYH, such as one encoded by a variant of hMYH as identified above) or a peptide sequence encoded by a diagnostic sequence as defined herein that is identifiable by conventional protein sequence methods (including mass spectroscopy, microarray analysis, pyrosequencing, etc), and/or antibody-based methods of detection (eg ELISA), and carrying out one or more such protein sequencing method(s).

Alternatively, the screening method and corresponding kit according to this invention may be based on one or more so-called 'surrogate markers' that are indicative of or correlated to the presence of a variant of a BER gene, hMYH or a diagnostic sequence as defined herein, or the polypeptide encoded thereby, such as proteins/amino acid sequences eg antibodies specific for a BER gene or protein.

Such a "surrogate marker" may therefore comprise:
(a) any biomolecule (including, but not limited to, nucleotides, proteins eg antibodies, sugars, and lipids);
(b) a chemical compound (including, but not limited to, drugs, metabolites thereof, and other chemical compounds); and/or
(c) a physical characteristic,
whose absence, presence, or quantity in an individual is measurable and correlated with the presence of a BER gene variant, hMYH or a diagnostic sequence as defined herein, or a protein encoded thereby.

In which alternative cases, the kit according to this invention may comprise one or more reagents for use in such alternative methods.

It will be evident to the person skilled in the art that, throughout the specification unless the context indicates otherwise, the hMYH gene is classified as an example of a BER pathway gene, but even if hMYH was found to act in an alternative pathway, then the screening methods, kits and uses as described herein in relation to a 'BER gene' would nevertheless apply mutatis mutandis to 'hMYH'.

BRIEF DESCRIPTION OF THE DRAWINGS

The basis for the invention will now be described in more detail with reference to the following Examples and Figures, in which.

DETAILED DESCRIPTION OF THE INVENTION

Example 1

Figure 1:
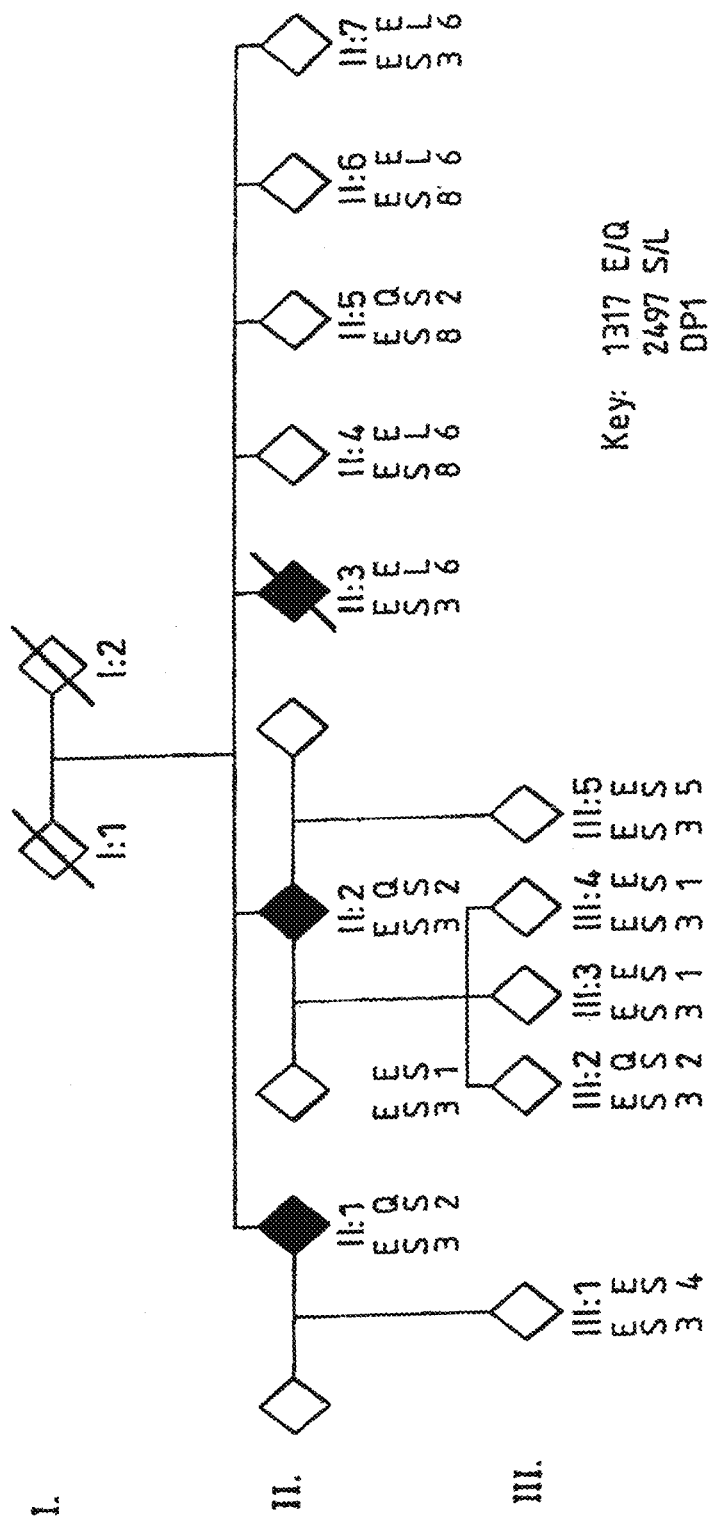
FIG. 1 shows the pedigree of family N. II.1 and II.2 were found to have approximately 50 macroscopically visible adenomas at 59 and 55 years of age. II.3 died following discovery of a colonic adenocarcinoma and an adjacent adenoma at 46 years of age, but without full assessment of the large bowel. II.4-7 were normal on colonoscopic assessment at between 36 and 49 years of age and III.1-III.5 were normal on colonoscopic assessment at between 24 and 33 years of age. APC haplotypes with the intragenic markers E1317Q, S2497L and the closely linked DP1 $(CA)_n$ repeat are shown.

General Methods and Protocols Relating to APC

Samples
Family N: Nucleic Acid was prepared from venous blood samples and from normal colonic mucosa obtained at surgery, using standard methods. Nine colorectal adenomas were obtained at colonoscopy or surgery and one adenoma and a carcinoma were obtained from archived tissues in paraffin blocks. Histopathology was confirmed by independent review. DNA and RNA were prepared from whole tissues that had been snap frozen or from micro-dissected tissue whose nature had been verified histologically on the same or adjacent sections.
Patients with multiple colorectal adenomas: DNA was extracted from venous blood samples from sixteen further unrelated patients with multiple adenomas, with or without co-existing carcinoma. All cases were shown to be normal on sequencing of exon 4 and the alternatively spliced region of exon 9 of APC, mutations in which are associated with AFAP (Hum Mol Genet 10 721-733 (2001). Archived tumour tissue was micro-dissected and DNA extracted using standard methods.
Patients with colorectal cancer: DNA was extracted from venous blood samples using standard methods.
Standard and Long Distance (LD-) PCR and Microsatellite Analysis
Exons 1-3 and 5-14 of APC were amplified using published primers (Cell 66, 589-600 (1991)), and exon 4 was amplified using ex4F (5'-TGCAGTCTTTATTAGCATTGTTT-3' SEQ ID NO:5) and ex4R (5'-TTCAAATAAGTTGTACTGC-CAAG-3' SEQ ID NO:6) which generated a 195 bp product. For DNA extracted from paraffin embedded blocks, exon 15 of APC was amplified as 40 overlapping fragments of 162-285 bp (See Appendix 1, Table 2). Exons 2-15 of β-catenin (Accession Nos. X89579, 13648651) (see Appendix 1, Table 3), 2-11 of p53 (Accession No. U94788) (see Appendix 1, Table 4), 1-16 of hMYH, 1-8 of hOGG1 (Accession Nos. AC066599, AC011610) and 2-5 of hMTH (Accession Nos. D38591-4) were amplified as 18, 11, 16, 11 and 4 fragments, respectively. Standard PCR was carried out in 50 µl reaction volumes containing 100 ng genomic DNA, 25 pmole primers, 0.2 mM dNTPs, 5 µl reaction buffer and 1 U AmpliTaq Gold DNA Polymerase (Applied Biosystems). Cycling parameters were 94° C. 10 mins, followed by 32 cycles of 50-67° C. 1 min, 72° C. 1 min, 94° C. 30 secs, and a final step of 72° C. 10 mins. For DNA extracted from fresh tissue, exon 15 of APC was amplified either as a single 6.67 kb LD-PCR fragment using N15F (1997) 5'-GCAAATCCTAAGAGAGAACAACTGT-3' (SEQ ID NO:7) and N15R1 (8684) 5'-TCCAGAACAAAAAC-CCTCTAACAAG-3' (SEQ ID NO:8), or as two overlapping LD-PCR fragments using N15F (1997) and NS15 4R (5571) 5'-CCTTCAATAGGCGTGTAATG-3' (SEQ ID NO:9) which generated a 3.59 kb product, and NS15 3F (3649) 5'-AAAGCAGTAAAACCGAACAT-3' (SEQ ID NO:10) and N15R (8698) 5'-TCAAATATGGCTTCCAGAACAAA-3' (SEQ ID NO:11) which generated a 5.07 kb product. Exons 10 to 16 of hMYH were amplified as a 3.1 kb LD-PCR fragment using Y10F1L (5'-GCTGATCCAGCA-GCACCCTTGTTT-3' SEQ ID NO:12) and Y16RL (5'-AATGGGGGCTTTCAGAGGTGTCACT-3' SEQ ID NO:13). The 50 µl LD-PCR reaction mixes contained 100 ng genomic DNA, 10 pmol primers, 0.35 mM dNTPs, 5 µl reaction buffer 3 and 1.75 U of Expand Long Template DNA Polymerase (Roche). Cycling parameters were 94° C. 2 mins followed by 33-35 cycles of 56° C. 1 min, 68° C. 4-8 mins (+20 secs per cycle, after cycle number 10) and 94° C. 20 secs, and a final elongation step at 68° C. for 4-8 mins. DNA extracted from normal and tumour tissue was tested for MSI using the markers D2S123, BAT 26, BAT 24, Mfd15, DP1(APC), D18S69 and BAT 25.
RT-PCR and Expression Analysis
100 ng-2 µg RNA was used for first strand cDNA synthesis using oligo (dT)$_{15}$ and Superscript II RNase H⁻ Transcriptase (Invitrogen Life Technologies). Second strand synthesis was carried out in 50 µl reaction volumes using 1 µl cDNA, 25 pmol primers, 0.2 mM dNTPs, 5 µl reaction buffer and 2-5 U AmpliTaq Gold DNA Polymerase. Cycling parameters were 94° C. for 10 mins, followed by 35-40 cycles of 94° C. 1 min, 50-54° C. 1 min, 72° C. 1-3 mins, and a final elongation step at 72° C. for 10 mins. Exons 1-14 of APC were amplified as a 1.958 kb fragment, using the primers previously described (Proc. Natl. Acad. Sci. (USA) 94, 2449-2453 (1997)). To determine the expression levels of individual APC alleles, the exon 11 polymorphism Y486 was assayed in recombinant RT-PCR product clones by restriction digestion or sequence analysis. To characterise aberrant splicing associated with the 423-1G>T somatic mutation, exons 3-12 of APC were amplified by RT-PCR using APCFEx3 (5'-GAGGGTTTGTAAATGGAAGCAG-3' SEQ ID NO:14) and APCjREx11-12 (5'-CTCATGCA-GCCTTTCATAGAGC-3' SEQ ID NO:15), cloned and sequenced. To quantify the expression level of the hMYH allele harbouring G382D, normal colonic mucosa cDNA from sibling II:1 was amplified using rY12F (5'-GTGGT-CAACTTCCCCAGAAA-3' SEQ ID NO:16) and rY14R (5'-GGCCAGCCCATATACTTGAT-3' SEQ ID NO:17), cloned and assayed with a Bgl II digest.

Sequencing

Standard PCR products were sequenced manually using the ThermoSequenase cycle sequencing kit (Amersham), and analysed on 6% polyacrylamide gels. For automated plasmid based sequencing, standard, LD- and RT-PCR products were purified using the PCR purification kit (Qiagen), cloned into pGEM-T Easy (Promega), and propogated in JM109 E. coli; at least twelve recombinant clones of each product were sequenced. Automated sequencing of RT-PCR product clones spanning exons 1-14 of APC was performed using two overlapping bi-directional sequencing reactions: (1) NS1_14F (39) 5'-ATGGCTGCAGCTTCATATGA-3' (SEQ ID NO:18) to NS1_14R2 (1049) 5'-GCTGTCT-TGGGAGCTAGAC-3' (SEQ ID NO:19); (2) NS1_14F2 (892) 5'-ACCATGAAACAGCCAGTGT-3' (SEQ ID NO:20) to NS1_14R (1978) 5'-CTGTGGTCCTCATTTG-TAG-3' (SEQ ID NO:21). Automated sequencing of LD-PCR products and clones spanning exon 15 of APC was performed using eight overlapping bi-directional sequencing reactions: (1) NS15 1F (1997) 5'-GCAAATCCTAAGAGA-GAACA-3' (SEQ ID NO:22) to NS15 8R (3146) 5'-GACTTTGCCTTCCAGAGTTC-3' (SEQ ID NO:23); (2) NS15 2F (2810) 5'-AAGCTCTGCTGCCCATACACA-3' (SEQ ID NO:24) to NS15 7R (3935) 5'-CTGCTATTTGCA-GGGTATTA-3' (SEQ ID NO:25); (3) NS15 3F (3649) 5'-AAAGCAGTAAAACCGAACAT-3' (SEQ ID NO:26) to NS15 3R (4775) 5'-TTGTTGGCATGGCAGAAATA-3' (SEQ ID NO:27); (4) NS15 4F (4480) 5'-TTCTTCCAGAT-GCTGATACT-3' (SEQ ID NO:28) to NS15 4R (5571) 5'-CCTTCAATAGGCGTGTAATG-3' (SEQ ID NO:29); (5) NS15 5F (5234) 5'-GCCCAAAGGGAAAAGTCACA-3' (SEQ ID NO:30) to NS15 5R (6346) 5'-ATTTGCACCTTC-CTGAATAG-3' (SEQ ID NO:31); (6) NS15 6F (6015) 5'-CCTGACTCACAGGGAGAAC-3' (SEQ ID NO:32) to NS15 6R (7135) 5'-CTGTCTACCTGGAGATGTAT-3' (SEQ ID NO:33); (7) NS15 7F (6807) 5'-GCCTC-CAAAAGCCCTAGTGA-3'(SEQ ID NO:34) to NS15 2R (7920) 5'-AGCACCTGAGGAAACGGTCTG-3' (SEQ ID NO:35); (8) NS15 8F (7552) 5'-GAAAACTCCCAC-CTAATCTC-3' (SEQ ID NO:36) to NS15 1R (8684) 5'-AACAAAAACCCTCTAACAAG-3' (SEQ ID NO:37).

Primer nucleotide numbers in parentheses are cited according to Science 253, 661-5 (1991). Automated sequencing of LD-PCR product clones spanning exons 10-16 of hMYH, RT-PCR product clones spanning exons 3-12 of APC and 12-14 of hMYH, and standard PCR product clones, was performed using M13 forward and reverse primers, as previously described (Hum. Mol. Genet 9, 1119-1129 (2000)). Sequence data for >12 clones was aligned (AlignIR v1.2, Li-Cor) and variants in two or more clones from the same allele were analysed by an independent assay on a fresh PCR product, to confirm that they represented real mutations and were not PCR or cloning induced errors.

Assays for Sequence Variants

In APC: Y486 (1458 C>T) in exon 11 was assayed using an Rsa I digest, as previously described (Cell 66, 589-600 (1991)). E1317Q (3949 G>C) in exon 15 was assayed using a Pvu II digest of a 503 bp PCR product generated using E1317QLF (3652) 5'-GCAGTAAAACCGAACATATG-3' (SEQ ID NO:38) and E1317QR (4137) 5'-TG-GACTTTTGGGTGTCTG-3' (SEQ ID NO:39); DNA from paraffin embedded blocks was assayed using a 224 bp PCR product generated with E1317QSF (3934) 5'-CTAATAC-CCTGCAAATAGCA-3' (SEQ ID NO:40) and E1317QR (4137). A545 (1635 A>G) in exon 13 and T1493 (4479 G>A), A1755 (5265 G>A), S1756 (5268 G>T), and S2497L (7491 C>T) in exon 15, were assayed by sequencing.

The somatic APC mutations E1284X (3850 G>T) and E1317X (3949 G>T) in exon 15 were assayed using a Bfr I digest of PCR products generated with E1317QLF and E1317QR. Somatic APC mutations were assigned to an allele by linking them to one of the polymorphic markers using either standard, RT-, or LD-PCR, followed by cloning and sequencing. The following missense variants in hMYH were assayed in 100 normal control patients: V22M (66 G>A) was assayed using an Nco I digest of exon 2 PCR products. Y165C (494 A>G) in exon 7 was assayed using normal (165N 5'-CGCCGGCCACGAGAATGGT-3' SEQ ID NO:41) or mutant (165M 5'-CGCCGGCCACGAGAAT-TGC-3' SEQ ID NO:42) specific ARMS primers together with the common primer 165C (5'-AGTGCTTCCCTG-GAGGTGAGA-3' SEQ ID NO:43). R260Q (779 G>A) in exon 10 was assayed using normal (260N 5'-CTTGGTT-GAAATCTCCTGCCC-3' SEQ ID NO:44) or mutant (260M 5'-CTTGGTTGAAATCTCCTGACT-3' SEQ ID NO:45) specific ARMS primers together with the common primer 260C (5'-CGAGCCATTGGTGCTGATC-3' SEQ ID NO:46). G382D (1145 G>A) was assayed using a Bgl II digest of exon 13 PCR products. S501F (1502 C>T) in exon 16 was assayed using normal (501N 5'-GCTTTTTC-CGACTGCACGCAG-3' SEQ ID NO:47) or mutant (501M 5'-GCTTTTTCCGACTGCACGAAA-3' SEQ ID NO:48) specific ARMS primers together with the common primer 501C (5'-GCATTCCAGGCTAAGCCTAGC-3' SEQ ID NO:49). All ARMS reactions incorporated internal control primers (AJ31 and AJ32) to validate the assay. SSCP and dHPLC analysis at the RTm and RTm+2° C., was carried out as described by Jones et al. (Hum. Genet. 106, 663-668 (2000)).

Somatic APC Mutation Database and Statistical Analysis

We reviewed literature reports of characterised somatic APC mutations in colorectal tumours. This included publications cited in the APC mutation database (Nucleic Acids Res, 24, 121-124 (1996)) and publications from the period 1991-2001 identified through a PubMed search. Reports of truncating mutations that were inconsistent with the published cDNA sequence (Science 253, 661-5 (1991)) were excluded, as were putative missense mutations since the evidence for their pathogenicity was inconclusive. Data on 503 somatic mutations observed in sporadic tumours and 308 somatic mutations observed in FAP and AFAP associated tumours was retrieved. This included cases of allelic loss, nonsense, frameshift and splice site mutations at invariant GT-AG dinucleotides, Statistical analysis was carried out using Fisher's Exact test.

Site Directed Mutagenesis (SDM) and Assays of mutY Glycosylase Activity

SDM with the primers y82c F (5'-GCGCGCGCGGGCG-CAATAGCCAAGCCC-3' SEQ ID NO:50) and g253d_F (5'-CCGCCCCACAAGTCGCTCGGCGGACGC-3' SEQ ID NO:51), cloning, expression and purification of wild type and mutant mutY, was carried out as previously described (Nucleic Acids Res. 29, 553-564 (2001)).

To determine the effect of the y82c and g253d mutations on the intrinsic rate of adenine removal compared to wild type, glycosylase assays were performed under single turnover conditions ([DNA]<[MutY]) as described (Biochem. 37, 14756-14764 (1998)) using a 30 bp duplex containing a centrally-located 8-oxo-G:A or G:A base pair. The amount of active protein (wild type 39%, y82c 53%, g253d 58%) was determined using active site titration methods (Biochem 37, 14756-14764 (1998)). The resulting data were fitted to the single exponential equation: $[P]_t=A_0[1-\exp(-k_{obs}t)]$. Under the conditions used for these experiments, $k_{obs}$ approximates $k_2$ (Biochem 37, 14756-14764 (1998)).

Example 2

Primers, Conditions and Methods for Amplification and Analysis of the Human BER Genes hMYH, hOGG1 and hMTH (1) Standard PCR Exons 1-16 of hMYH, 1-8 of hOGG1 (Accession Nos. AC066599, AC011610) and 2-5 of hMTH (Accession Nos. D38591-4) were amplified as 16, 11 and 4 fragments, respectively (Tables 1-3). Standard PCR was carried out in 50 µl reaction volumes containing 100 ng genomic DNA, 25 pmole primers, 0.2 mM dNTPs, 5 µl reaction buffer and 1 U AmpliTaq Gold DNA Polymerase (Applied Biosystems). Cycling parameters were 94° C. 10 mins, followed by 32 cycles of 50-67° C. 1 min, 72° C. 1 min, 94° C. 30 secs, and a final step of 72° C. 10 mins.

TABLE 1

Primers used for the amplification of hMYH

| Exon | Primer name | Sequence | SEQ NO. | Product size | Annealing Temp. |
|---|---|---|---|---|---|
| 1 | Y1F | 5'-GAAGCTGCGGGAGCTGAAA-3' | 52 | 133 bp | 60° C. |
|   | Y1R | 5'-ATCCCCGACTGCCTGAACC-3' | 53 | | |
| 2 | Y2F | 5'-CTGCATTTGGCTGGGTCTTT-3' | 54 | 263 bp | 54° C. |
|   | Y2R | 5'-CGCACCTGGCCCTTAGTAAG-3' | 55 | | |
| 3 | Y3F | 5'-AGCCTGTGCAGGGATGATTG-3' | 56 | 272 bp | 57° C. |
|   | Y3R | 5'-CAACCCCAGATGAGGAGTTAGG-3' | 57 | | |
| 4 | Y4F | 5'-CTCATCTGGGGTTGCATTGA-3' | 58 | 167 bp | 57° C. |
|   | Y4R | 5'-GGGTTGGCATGAGGACACTG-3' | 59 | | |
| 5 | Y5F | 5'-GGGCAGGTCAGCAGTGTC-3' | 60 | 189 bp | 57° C. |
|   | Y5R | 5'-TACACCCACCCCAAAGTAGA-3' | 61 | | |
| 6 | Y6F | 5'-TACTTTGGGGTGGGTGTAGA-3' | 62 | 185 bp | 54° C. |
|   | Y6R | 5'-AAGAGATCACCCGTCAGTCC-3' | 63 | | |
| 7 | Y7F | 5'-GGGACTGACGGGTGATCTCT-3' | 64 | 186 bp | 54° C. |
|   | Y7R | 5'-TTGGAGTGCAAGACTCAAGATT-3' | 65 | | |
| 8 | Y8F | 5'-CCAGGAGTCTTGGGTGTCTT-3' | 66 | 240 bp | 57° C. |
|   | Y8R | 5'-AGAGGGGCCAAAGAGTTAGC-3' | 67 | | |
| 9 | Y9F | 5'-AACTCTTTGGCCCCTCTGTG-3' | 68 | 196 bp | 57° C. |
|   | Y9R | 5'-GAAGGGAACACTGCTGTGAAG-3' | 69 | | |
| 10 | Y10F | 5'-GTGCTTCAGGGGTGTCTGC-3' | 70 | 262 bp | 57° C. |
|   | Y10R | 5'-TGTCATAGGGCAGAGTCACTCC-3' | 71 | | |
| 11 | Y11F | 5'-TAAGGAGTGACTCTGCCCTATG-3' | 72 | 248 bp | 54° C. |
|   | Y11R | 5'-GCCAAGAGGGGCTTTAGG-3' | 73 | | |
| 12 | Y12F | 5'-AGCCCCTCTTGGCTTGAGTA-3' | 74 | 298 bp | 57° C. |
|   | Y12R | 5'-TGCCGATTCCCTCCATTCT-3' | 75 | | |
| 13 | Y13F | 5'-AGGGCAGTGGCATGAGTAAC-3' | 76 | 242 bp | 57° C. |
|   | Y13R | 5'-GGCTATTCCGCTGCTCACTT-3' | 77 | | |
| 14 | Y14F | 5'-TTGGCTTTTGAGGCTATATCC-3' | 78 | 256 bp | 54° C. |
|   | Y14R | 5'-CATGTAGGAAACACAAGGAAGTA-3' | 79 | | |
| 15 | Y15F | 5'-TGAAGTTAAGGGCAGAACACC-3' | 80 | 205 bp | 54° C. |
|   | Y15R | 5'-GTTCACCCAGACATTCGTTAGT-3' | 81 | | |
| 16 | Y16F | 5'-AGGACAAGGAGAGGATTCTCTG-3' | 82 | 224 bp | 54° C. |
|   | Y16R | 5'-GGAATGGGGGCTTTCAGA-3' | 83 | | |

TABLE 2

Primers used for the amplification of hOGG1

| Exon | Primer name | Sequence | SEQ ID NO. | Product size | Annealing Temp. |
|---|---|---|---|---|---|
| 1 | M1F | 5'-CTTTGGGCGTCGACGAG-3' | 84 | 237 bp | 57° C. |
|   | M1R | 5'-GAGGGGACAGGCTTCTCAG-3' | 85 |   |   |
| 2 | M2F1 | 5'-ATTGAGTGCCAGGGTTGTCA-3' | 86 | 245 bp | 57° C. |
|   | M2R1 | 5'-CGGAACCCCAGTGGTGATAC-3' | 87 |   |   |
|   | M2F2 | 5'-TGTACTAGCGGATCAAGTAT-3' | 88 | 286 bp | 50° C. |
|   | M2R2 | 5'-TGGCAAAACTGAGTCATAG-3' | 89 |   |   |
| 3 | M3F1 | 5'-GTCTGGTGTTGCTTTCTCTAAC-3' | 90 | 229 bp | 50° C. |
|   | M3R1 | 5'-GTGATGCGGGCGATGTT-3' | 91 |   |   |
|   | M3F2 | 5'-TCTCCAGGTGTGCGACTGC-3' | 92 | 275 bp | 57° C. |
|   | M3R2 | 5'-AGGAAGCCTTGAGAAGGTAACC-3' | 93 |   |   |
| 4 | M4F | 5'-GGAAGAACTTGAAGATGCCT-3' | 94 | 296 bp | 55° C. |
|   | M4R | 5'-GCTCATTTCCTGCTCTCC-3' | 95 |   |   |
| 5 | M5F | 5'-CCGGCTTTGGGGCTATA-3' | 96 | 279 bp | 57° C. |
|   | M5R | 5'-GTTTCTACCATCCCAGCCCA-3' | 97 |   |   |
| 6 | M6F | 5'-TACTTCTGTTGATGGGTCAC-3' | 98 | 153 bp | 55° C. |
|   | M6R | 5'-TGGAGGAGAGGAAACCTAG-3' | 99 |   |   |
| 7 | M7F | 5'-ACCTCCCAACACTGTCACTA-3' | 100 | 265 bp | 55° C. |
|   | M7R | 5'-CCCTCCCCAACATGAGA-3' | 101 |   |   |
| 8 | M8F1 | 5'-CTGTGGCCCACGCACTTGTG-3' | 102 | 253 bp | 57° C. |
|   | M8R1 | 5'-ACGTCCTTGGTCCAGCAGTGGT-3' | 103 |   |   |
|   | M8F2 | 5'-GAGAGGGGATTCACAAGGTG-3' | 104 | 287 bp | 55° C. |
|   | M8R2 | 5'-GCCATTAGCTCCAGGCTTAC-3' | 105 |   |   |

TABLE 3

Primers used for the amplification of hMTH

| Exon | Primer Name | Sequence | SEQ ID NO. | Product size | Annealing Temp. |
|---|---|---|---|---|---|
| 2 | T2F | 5'-GCAAGGACAGAGGGCTTTCTG-3' | 106 | 249 bp | 67° C. |
|   | T2R | 5'-CCAGCAGGCCATCAACTGAT-3' | 107 |   |   |
| 3 | T3F | 5'-GCACGTCATGGCTGACTCT-3' | 108 | 246 bp | 57° C. |
|   | T3R | 5'-CTGGGAAAGCCGGTTCTAT-3' | 109 |   |   |
| 4 | T4F | 5'-TCCCTGGGCTGTGTGTAGAT-3' | 110 | 298 bp | 57° C. |
|   | T4R | 5'-GAGATGGGACCCGCATAGT-3' | 111 |   |   |
| 5 | T5F | 5'-TGAAGTTTGGGTTGCACCTC-3' | 112 | 281 bp | 57° C. |
|   | T5R | 5'-AGATGGTTTGCGGCTGTTC-3' | 113 |   |   |

(2) Long-Distance (LD-) PCR

Exons 10 to 16 of hMYH were amplified as a 3.1 kb LD-PCR fragment using Y10F1L (5'-GCTGATCCCAGCAGCACCCTTGTTT-3' SEQ ID NO:114) and Y16RL (5'-AATGGGGGCTTTCAGAGGTGTCACT-3' SEQ ID NO:115). The 50 µl LD-PCR reaction mixes contained 100 ng genomic DNA, 10 pmol primers, 0.35 mM dNTPs, 5 µl reaction buffer 3 and 1.75 U of Expand Long Template DNA Polymerase (Roche). Cycling parameters were 94° C. 2 mins followed by 33-35 cycles of 56° C. 1 min, 68° C. 4-8 mins (+20 secs per cycle, after cycle number 10) and 94° C. 20 secs, and a final elongation step at 68° C. for 4-8 mins.

(3) RT-PCR and Expression Analysis 100 ng-2 µg RNA was used for first strand cDNA synthesis using oligo (dT)$_{15}$ and Superscript II RNase H$^-$ Transcriptase (Invitrogen Life Technologies). Second strand synthesis was carried out in 50 µl reaction volumes using 1 µl cDNA, 25 pmol primers, 0.2 mM dNTPs, 5 µl reaction buffer and 2-5 U AmpliTaq Gold DNA Polymerase. Cycling parameters were 94° C. for 10 mins, followed by 35-40 cycles of 94° C. 1 min, 50-54° C. 1 min, 72° C. 1-3 mins, and a final elongation step at 72° C. for 10 mins. To quantify the expression level of the hMYH allele harbouring G382D, normal colonic mucosa cDNA from sibling II:1 was amplified using rY12F (5'-GTGGTCAACTTCCCCAGAAA-3' SEQ ID NO:116) and rY14R (5'-GGCCAGCCCATATACTTGAT-3' SEQ ID NO:117), cloned and assayed with a Bgl II digest.

(4) Sequencing

Standard PCR products were sequenced manually using the ThermoSequenase cycle sequencing kit (Amersham), and analysed on 6% polyacrylamide gels. For automated plasmid based sequencing, standard, LD- and RT-PCR products were purified using the PCR purification kit (Qiagen), cloned into pGEM-T Easy (Promega), and propagated in JM109 *E. coli*; at least twelve recombinant clones of each product were sequenced. Automated sequencing of LD-PCR product clones spanning exons 10-16 of hMYH, RT-PCR product clones spanning exons 12-14 of hMYH, and standard PCR product clones, was performed using M13 forward and reverse primers.

(5) Single Strand Conformation Polymorphism (SSCP) and Denaturing High Performance Liquid Chromatography (dH-PLC) Analysis SSCP and dHPLC analysis at the RTm and RTm+2° C., was carried out as previously described (Hum. Genet. 106, 663-668 (2000)).

(6) Assays for Sequence Variants

The missense variants in hMYH were assayed in 100 normal control patients (Table 4). All ARMS reactions incorporated internal control primers (AJ31 and AJ32, Hum. Genet. 106, 663-668 (2000)) to validate the assay.

TABLE 4

Assays for missense variants in hMYH

| Variant | Exon | Assay | SEQ ID NO. |
|---|---|---|---|
| V22M (66 G→A) | 2 | NcoI digest | |
| Y165C (494 A→G) | 7 | Normal ARMS (165N 5'-CGCCGGCCACGAGAATGGT-3') | 118 |
| | | Mutant ARMS (165M 5'-CGCCGGCCACGAGAATTGC-3') | 119 |
| | | Common (165C 5'-AGTGCTTCCCTGGAGGTGAGA-3') | 120 |
| R260Q (779 G→A) | 10 | Normal ARMS (260N 5'-CTTGGTTGAAATCTCCTGCCC-3') | 121 |
| | | Mutant ARMS (260M 5'-CTTGGTTGAAATCTCCTGACT-3') | 122 |
| | | Common (260C 5'-CGAGCCATTGGTGCTGATC-3') | 123 |
| H324Q (972 C→G) | 12 | Normal ARMS (324N 5'-CCAGCTCCCAACACTGGAGAC-3') | 124 |
| | | Mutant ARMS (324M 5'-CCAGCTCCCAACACTGGAGAG-3') | 125 |
| | | Common (324C 5'-CCCAGGCTGTTCCAGAACAC-3') | 126 |
| G382D (1145 G→A) | 13 | BglII digest | |
| S501F (1502 C→T) | 16 | Normal ARMS (501N 5'-GCTTTTTCCGACTGCACGCAG-3') | 127 |
| | | Mutant ARMS (501M 5'-GCTTTTTCCGACTGCACGAAA-3') | 128 |
| | | Common (501C 5'-GCATTCCAGGCTAAGCCTAGC-3') | 129 |

Example 3

Investigation of and Data from Family N

As summarised above, and using the methods and materials as described in Examples 1 and 2, we investigated a family N in which three siblings (II:1-3) were affected by multiple colorectal adenomas and carcinoma (FIG. 1). This was a Caucasian family but the method is not limited to any particular ethnic grouping. DNA and RNA extracted from normal colonic mucosa from sibling II:1 and DNA extracted from normal colon tissue embedded within a paraffin block from the deceased sibling II:3, was amplified and sequenced for the 8532 bp open reading frame (ORF) of the APC gene (identification and characterisation of the APC gene is described in Cell 66, 589-600 (1991)).

Five silent base substitutions (1458 C>T [Y486], 1635 A>G [A545], 4479 G>A [T1493], 5265 G>A [A1755] and 5268 G>T [S1756]), and two missense variants (E1317Q and S2497L) were identified, but no clearly pathogenic change was found. Assays of the variants showed that none were present in all three affected siblings and that their shared wild type APC haplotype was also present in five other family members who were phenotypically normal on colonoscopic assessment (FIG. 1). Sequencing of RT-PCR products of exons 1-14 of APC in sibling II:1 confirmed equal expression of both alleles with alternate splicing of exons 9a and 10a, as previously reported and described in Human Mol Genet 10, 735-740 (2001). These data effectively excluded inactivation of APC as the primary inherited defect in family N.

Inherited mutations of the mismatch repair (MMR) genes cause hereditary non-polyposis colorectal cancer (HNPCC) characterised by micro-satellite instability (MSI) in the associated tumours. Assessment for MSI in DNA extracted from each of the available tumours that included five adenomas from sibling II:1, four adenomas from sibling II:2, and one adenoma and one carcinoma from sibling II:3, revealed instability with only one (Mfd15) of the seven markers tested in a single adenoma. This observation, and the multiple adenoma phenotype, provided evidence against the presence of a MMR gene defect in family N.

Figure 2A:
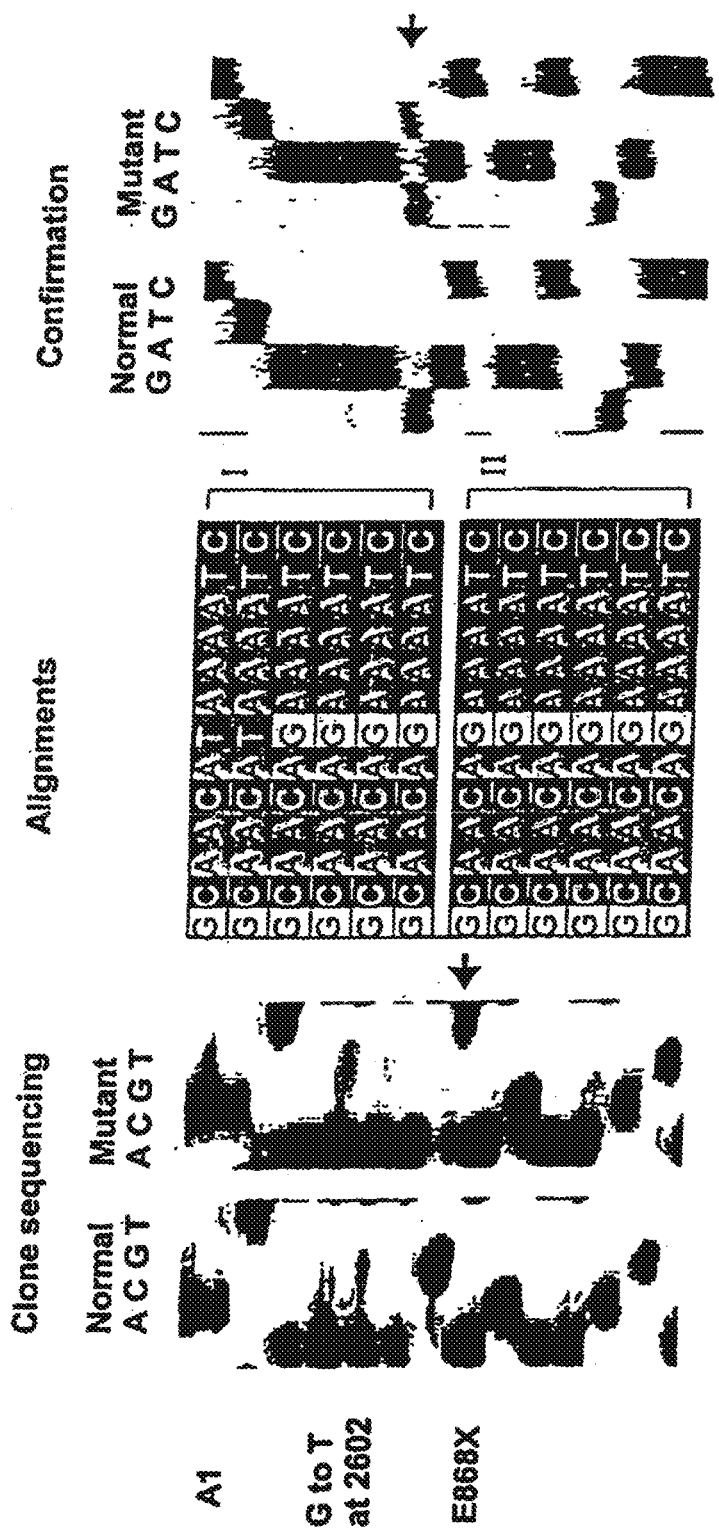
FIG. 2 shows the identification of somatic G:C→T:A mutations of APC in colorectal tumours. Sequences of LD-PCR product clones were aligned. Variants in two or more clones from the same allele (I or II) were confirmed by an independent assay on a fresh PCR product. (a) G>T mutation at position 2602 (E868X) in adenoma A1 confirmed by direct sequencing of standard PCR products. (b) G>T mutation at position 4351 (E1451X) on the second APC allele from adenoma A1 confirmed by direct sequencing of LD-PCR products. (c) G>T mutation at position 3850 (E1284X) in adenoma B5 confirmed by restriction enzyme analysis. Arrows indicate the position of the G:C→T:A mutations on the sequencing gels and the mutant allele on Bfr I cleavage of a PCR product amplified from adenoma B5. M DNA size marker (φ×174 Hae III), −ve wild type control DNA, +ve B5 adenoma DNA.
Figure 2B:
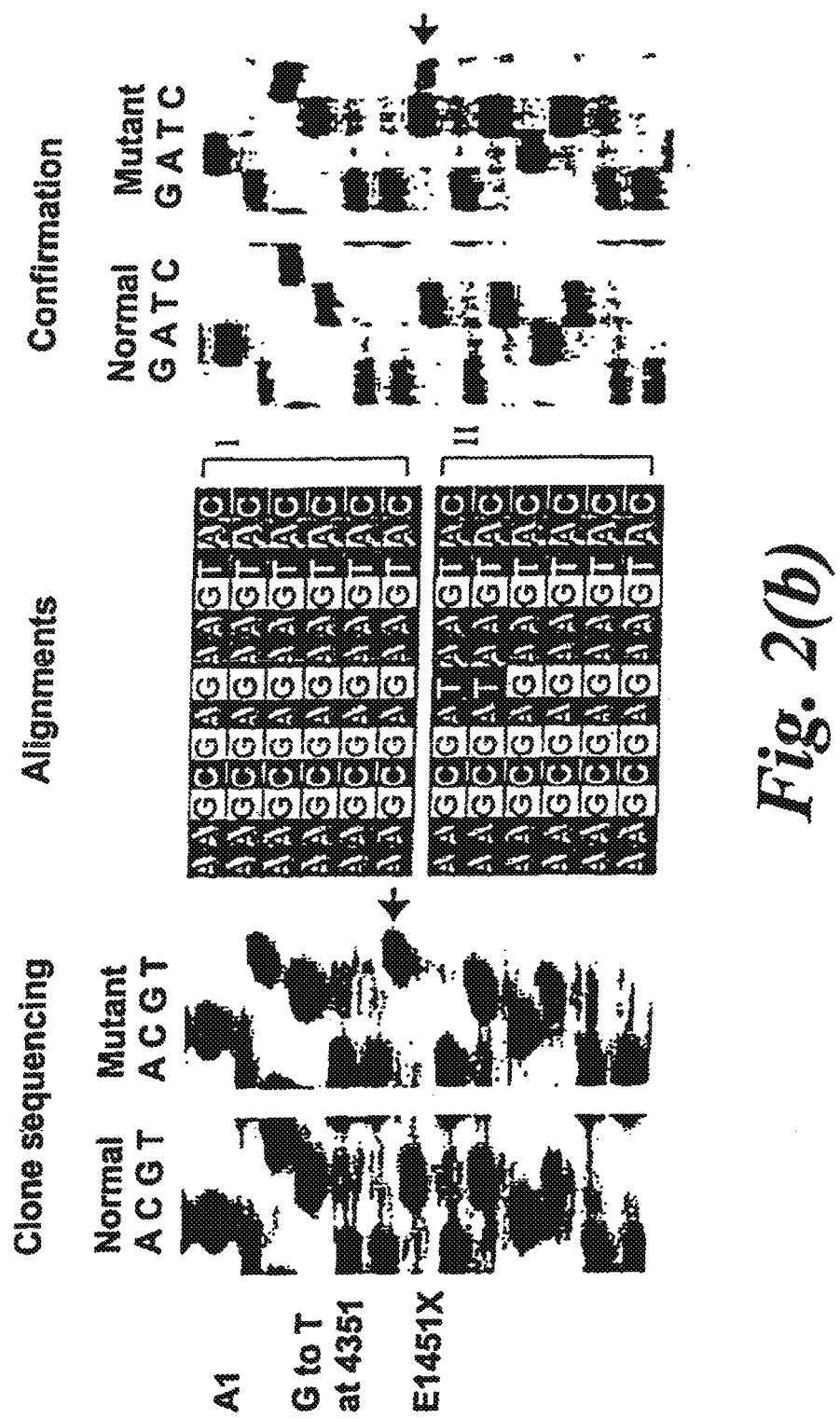
Figure 2C:
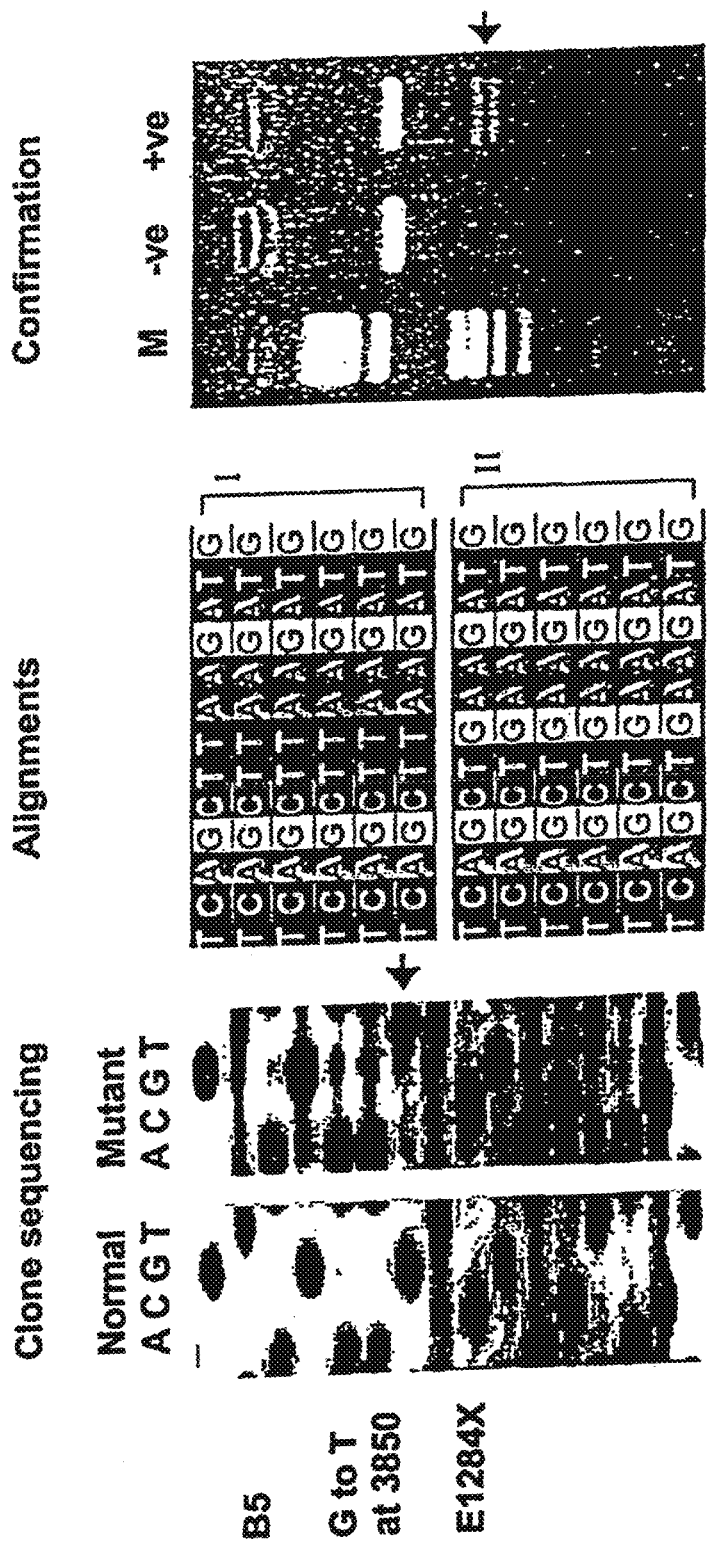

Since biallelic inactivation of APC occurs in most colorectal adenomas and carcinomas (Hum Mol Genet 10 721-733 (2001)), we sequenced the APC ORF to identify somatic mutations in each of the 11 tumours obtained from family N. Eighteen mutations were characterised, of which 15 were G:C→T:A transversions, including 14 nonsense changes and one splice site mutation (Table 5 and FIG. 2). The three remaining mutations were two C:G→T:A transitions at CpG dinucleotides and a case of allelic loss (Table 6).

TABLE 5

Somatic APC mutations identified in family N

| Sample[¶] | Nucleotide change | Amino acid change | No. of clones (x/y)[n^] | Sequence context |
|---|---|---|---|---|
| A1 | 2602 G > T | E868X | 2/6 | AGAAAAT |
| | 4351 G > T | E1451X | 2/6 | AGAAGTA |
| A2 | 721 G > T | E241X | NA | AGAAGCA |
| | 4381 G > T | E1461X | 2/6 | TGAAAAG |
| A3 | 4717 G > T | E1573X | 4/5 | TGAAATA |
| | NI | NI | | |
| A4 | 423-1 G > T[#] | NA | 2/2 | NA |
| | 4351 G > T | E1451X | 6/6 | AGAAGTA |
| A5 | 601 G > T | E201X | NA | GGAAGAA |
| | 4348 C > T | R1450X | 3/6 | NA |
| B2 | 3331 G > T | E1111X | 7/10 | AGAAACA |
| | LOH | LOH | | NA |
| B4 | 3586 C > A | S1196X | 3/7 | TGAAAAT |
| | 3856 G > T | E1286X | 4/5 | TGAAATA |
| B5 | 604 G > T | E202X | 3/6 | AGAACAA |
| | 3850 G > T | E1284X | 6/6 | TGAAGAT |

TABLE 5-continued

Somatic APC mutations identified in family N

| Sample¶ | Nucleotide change | Amino acid change | No. of clones (x/y)ᵝˆ | Sequence context |
|---|---|---|---|---|
| B6 | 2863 G > T | E955X | 5/7 | AGAATAC |
|  | 3949 G > T | E1317X | 4/6 | TGAAGAT |
| C2b | 1495 C > T | R499X | 3/6 | NA |
|  | NI | NI |  |  |
| C1a | NI | NI |  |  |
|  | NI | NI |  |  |

¶Five adenomas from sibling II:1 (A1-5), four adenomas from sibling II:2 (B2, 4-6), and one adenoma (C2b) and one carcinoma (C1a) from sibling II:3 were analysed for somatic APC mutations. Mutations were described according to the established nomenclature system. Biallelic mutations were proven to be on opposite alleles in all tumours, except A2 and A5. 423-1 G > T# was shown to cause skipping of exon 4 and predicted to terminate the reading frame at the 7ᵗʰ codon of exon 5.
ᵝNumber of clones, where x represents the number with the mutation and y represents the total number from that allele. In general, mutations were found in only a proportion of clones. Non-mutated clones from the same allele most likely represent contaminating normal tissue. All mutations were confirmed by an independent assay on a fresh PCR product.
ˆSequence context surrounding the coding region G:C→T:A mutations (underlined) (the sequence of the non-transcribed strand is shown except for S1196X in B4).
NA = not applicable;
NI = not identified.

The carcinoma did not contain any identified APC mutations despite re-sequencing of the ORF in DNA from a second micro-dissected tumour sample. Sequence analysis of the coding regions of β-catenin and p53 in DNA from this carcinoma also failed to identify any somatic mutations, suggesting involvement of an alternative tumourigenic pathway. We compared the proportion of G:C→T:A transversion mutations detected in tumours from family N to a database of 503 reported somatic APC mutations from sporadic colorectal adenomas and carcinomas and 308 somatic mutations from FAP associated tumours. The excess of G:C→T:A transversions in family N was highly significant (15/18 vs. 49/503, P=2.77×10⁻¹² and 15/18 vs. 30/308, P=7.69×10⁻¹² respectively).

Figure 3C:
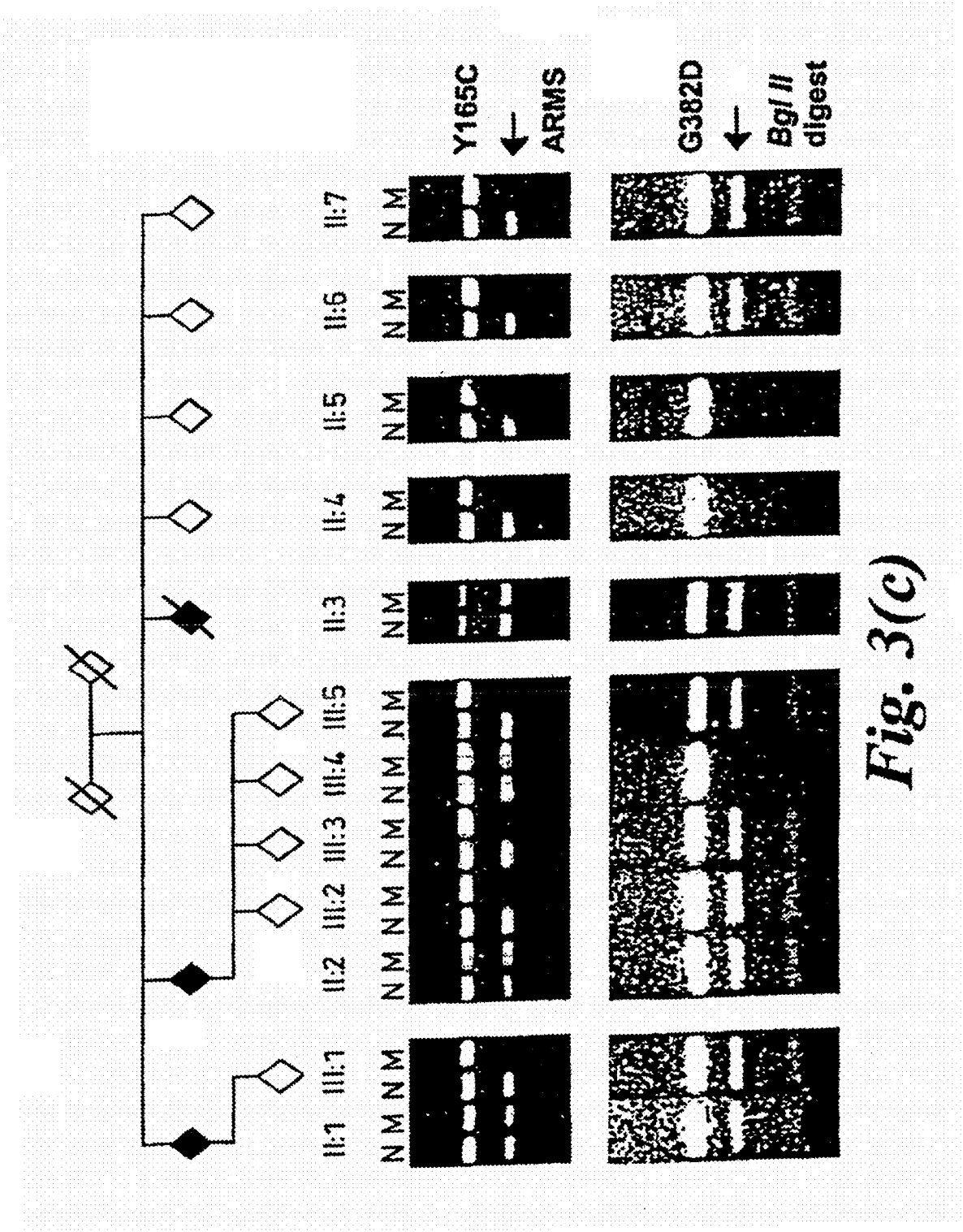
FIG. 3 shows the identification and segregation of germline hMYH variants in family N. Direct sequencing of constitutional DNA from sibling II:1 revealed (a) an A to G substitution at nucleotide 494 in exon 7 corresponding to Y165C (arrow) and (b) a G to A substitution at nucleotide 1145 in exon 13 corresponding to G382D (arrow). (c) Screening for Y165C by ARMS and G382D by a Bgl II digest revealed that the three affected siblings (filled symbols) were compound heterozygotes for these hMYH missense variants, while normal family members (non-filled symbols) were either heterozygous for one of the variants, or normal. N=normal ARMS reaction, M=mutant ARMS reaction. Arrows indicate the positions of the mutant alleles.

To determine if an inherited defect in one of the human BER genes (hOGG1, hMYH or hMTH) was responsible for the pattern of somatic G:C→T:A mutations in family N, DNA extracted from peripheral blood lymphocytes from sibling II:1 was amplified and sequenced for the coding regions of hOGG1, hMYH and hMTH. Two amino acid variants were identified in hMYH, Y165C (an A to G substitution at nucleotide 494 in exon 7) and G382D (a G to A substitution at nucleotide 1145 in exon 13) (FIG. 3). No missense variants or other likely pathogenic changes were identified in hOGG1 or hMTH.

Both hMYH variants were assayed in blood DNA samples from all members of family N and 100 Caucasian control individuals with no history of colorectal adenoma or carcinoma. In family N, the three affected siblings were compound heterozygotes for Y165C and G382D and the unaffected family members were either heterozygous for one of these variants or normal (FIG. 3). Each of the missense variants was also identified once in different normal controls. Since the G to A substitution causing G382D was located at the first base in exon 13, its potential affect on splicing and expression was examined. Only 31 of 100 clones obtained by RT-PCR of normal colonic mucosa total RNA from sibling II:1 harboured the G382D allele, although no aberrant splicing could be detected.

Somatic mutations of hMYH were sought in each of the eleven tumours by dHPLC and SSCP analysis of all exons and by screening for allelic loss by assay of the exon 7 and 13 missense variants. No somatic mutations were identified to suggest that hMYH might function as a tumour suppressor in a manner analogous to the MMR genes in HNPCC (Hum. Mol. Genet. 10, 735-740 (2001)). Neither was there clear evidence for the Y165C or G382D variants being dominant to wild type, since heterozygotes for each were phenotypically normal. Rather, the occurrence of the multiple adenoma phenotype in only the three compound heterozygotes suggested transmission as an autosomal recessive trait.

We then searched for germline mutations of hMYH, hOGG1 and hMTH by sequence analysis of their ORFs in sixteen unrelated patients with between 3 and ~50 colorectal adenomas, with or without carcinoma. hMYH mutations were also sought by dHPLC analysis of all exons in forty-two unrelated patients with colorectal cancer diagnosed at 40 years of age or less or with a family history of at least one first degree relative also affected by colorectal cancer. Several frequent missense polymorphisms were identified, S326C in hOGG1 (Oncogene 16, 3219-32225 (1998)), and V22M, H324Q (J. Bactiol. 178, 3885-3892 (1996)), and S501F in hMYH, but their allele frequencies were not significantly different in the patient groups compared to 100 unaffected controls. One case, MA12, with three adenomas and a carcinoma, was a compound heterozygote for the unique hMYH missense variant R260Q (779 G>A) and the S501F polymorphism. Analysis of the APC ORF in the four tumours revealed two G:C→T:A transversions producing nonsense changes (E477X and S1344X), two frame-shift mutations and one case of allelic loss. Other family members were not available for study and the limited number of tumours precluded establishing a meaningful pattern of APC mutation.

Figures 4A, 4B:
FIG. 4 shows the evolutionary conservation of the variant residues in hMYH. Comparison of the variant residues (a) Y165C and (b) G382D in family N with hMYH homologues from *Homo sapiens* (*H. sap.*), *Mus musculus* (*M. mus.*), *Arabidopsis thaliana* (*A. tha.*), *Schizosaccharomyces pombe* (*S. pom.*), *Hemophilus influenzae* (*H. inf.*), *Vibrio cholerae* (*V. cho.*), *Salmonella typhimurium* (*S. typ.*) and *E. coli* using ClustalW. Arrows indicate the position of the variant residues. Identical, conserved and semi-conserved residues are shaded black, dark grey and light grey respectively. // indicates the position of 18 amino acids in *A. tha.* that are not present in the other organisms.

Comparison of hMYH homologues in bacteria, yeast, plant and mammals revealed identical or similar amino acids at the positions of the non-conservative missense changes identified in family N (FIG. 4). To gain insight into the functional consequences of the missense variants, we assessed the effects of the equivalent E coli mutY mutations, y82c and g253d, on the intrinsic rate of adenine removal from a centrally located 8-oxo-G:A or G:A mismatch in a 30 bp duplex.

Figure 5:
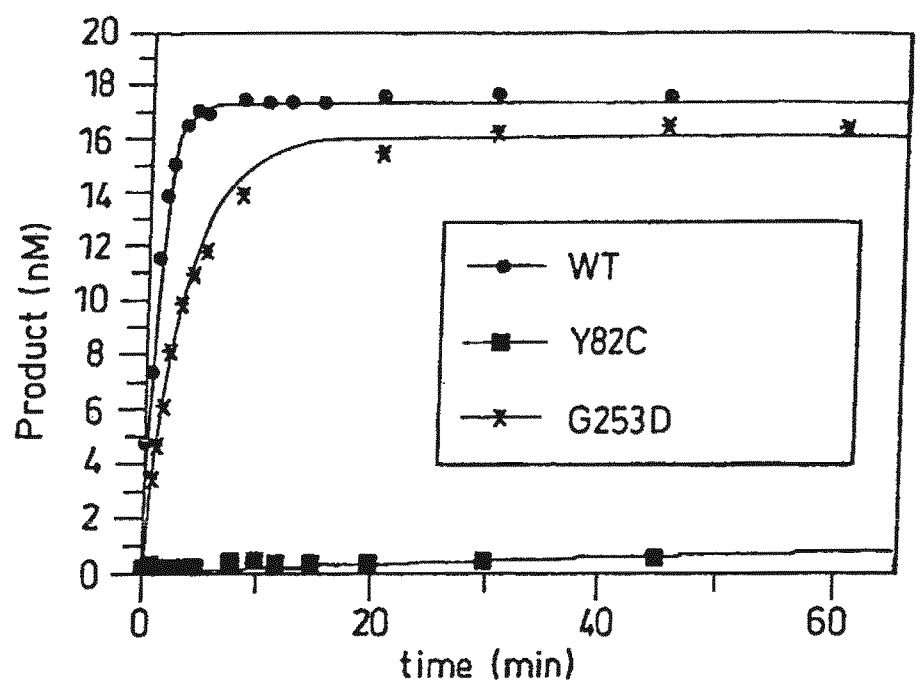
FIG. 5 shows representative plots of single turnover adenine glycosylase assays. Wild type, Y82C, and G253D mutY were assayed for glycosylase activity at 2° C. with a 20 nM duplex DNA substrate containing an 8-oxo G:A mismatch and 30 nM mutY (active site concentration). $k_2$ $(min^{-1})=1.6\pm0.2$ for wild type, $0.26\pm0.05$ for G253D and <0.0006 (estimated) for Y82C. All values represent an average of at least four separate determinations and the error is reported as the standard deviation.

The mutant proteins exhibited significantly slower rates of adenine removal than wild type (FIG. 5). The mutant proteins exhibited approximately ninety-fold (Y82C) and six-fold (G253D) slower rates of adenine removal from the G:A substrate at 37° C. (k2 (min-1)=1.6±0.04 for wild type, 0.04±0.01 for Y82C and 0.22±0.04 for G253D). The high affinity of MutY for 8-oxo-G:A substrates results in reaction rates that are too fast at 37° C. to be measured using our manual methods, and therefore the reaction rates with this duplex were analysed at 4° C. (FIG. 5). The G253D enzyme exhibited a 5-fold decreased rate of adenine removal; while the Y82C enzyme was so severely compromised in its catalytic activity that minimal conversion of substrate to product was observed during the time period that was monitored.

The dramatic effect of the y82c mutation is consistent with the findings of structural studies of mutY (Nat Struct Biol 5 1058-1064 (1998)), which locate y82 within the pseudo-HhH motif (79-gxgyya-84) and suggest a role in mismatch specificity and flipping of adenine into the base specificity pocket. The reduction in activity associated with g253d was similar to that observed with a truncated form of mutY that lacked the C-terminal third of the protein (Nucleic Acids Res. 29, 553-564 (2001)). In the colonic mucosa, the activity of the hMYH G382D allele may be further compromised by the reduced expression we noted on RT-PCR analysis.

The activity of mutY on mismatched DNA substrates is influenced by the immediate sequence context, and methylation interference experiments have shown that mutY interacts with purines including the G:A mismatched bases and two bases each side (J Biol Chem 270 23582-23588 (1995)). Examination of the sequence surrounding the 14 coding region G:C→T:A mutations in family N revealed that the two bases immediately 3' to the mutated G were always AA. Furthermore, 13/14 sites matched three or all bases in a sequence extending one base 5' (A/T) and three bases 3' (G/A,A,A) to the mutated GAA (Table 5).

Inherited factors are thought to play a major role in at least 15% of colorectal cancer cases, but established predisposition genes account only for a minority of these (Cell 87, 159-170 (1996)). The sub-polymorphic frequency of the hMYH variants identified in family N, and the lack of evidence for pathogenic variants in the other multiple adenoma and colorectal cancer cases studied here, suggest that inherited defects of hMYH will prove to be an uncommon cause of colorectal tumour predisposition. The multiple adenoma phenotype in members of family N may reflect the number of somatic mutations required for initiation of adenoma development. Patients with FAP develop hundreds or thousands of adenomas, each requiring only a single somatic APC mutation. The compound heterozygotes in family N may be more comparable to patients with attenuated FAP (AFAP) who develop smaller numbers of adenomas that require two somatic APC mutations for tumour initiation (Nat. Genet. 20, 385-388 (1998)). By contrast, patients with HNPCC develop only one or a few adenomas or carcinomas that require somatic inactivation of a wild type MMR allele and two somatic APC mutations.

Example 4

Investigation of and Data from Seven Unrelated Patients

This example describes the identification of seven further, unrelated patients having multiple colo-rectal adenomas and biallelic germline MYH mutations, including four cases homozygous for truncating mutations. Colo-rectal tumours from these individuals exhibit a significant excess of somatic G:C→T:A mutations, as compared to sporadic and FAP-associated tumours, confirming that biallelic mutations in MYH predispose to CRC.

Methods
Samples

Seventeen unrelated cases of British descent and four unrelated cases of Indian or Pakistani descent, each having multiple colo-rectal adenomas and/or carcinoma were analysed. DNA was prepared from venous blood samples, and from adenoma and carcinoma tissue from colon that had been micro-dissected from paraffin blocks. The nature of all tissues was verified histologically.

PCR Amplification

Exons 4 and 9 of APC, 1-16 of MYH, 1-8 of OGG1 and 2-5 of MTH1 as 2, 16, 11 and 4 fragments, were amplified as previously described (Al-Tassan et al, Nat Genet 30 227-232 (2002)). A ~2.8 kb segment of APC (between codons 653 and 1589) was amplified, which encompassed the somatic mutation cluster region, as eighteen overlapping fragments. Primer sequences are presented in Appendix 1.

Denaturing High Performance Liquid Chromatography (dHPLC) Analysis and Fraction Collection dHPLC was carried out using the 3500HT WAVE nucleic acid fragment analysis system (Transgenomic Ltd, Crewe Hall Weston Road, Crewe CW1 6UZ, UK). To enhance the formation of heteroduplexes prior to analysis, the PCR products were denatured at 94° C. and re-annealed by cooling to 50° C. at a rate of 1° C. per minute. dHPLC was carried out at the melting temperatures predicted by Wavemaker (version 4.1) software (Transgenomic) with a 12% acetonitrile (ACN) gradient over 3 minutes. Samples displaying aberrant dHPLC elution profiles were sequenced directly; those samples without clear sequence variations were re-analysed by isolating and sequencing dHPLC separated heteroduplexes. Fraction collection of heteroduplexes was carried out using a Transgenomic FCW-200 in-line fragment collector and products were eluted in 8% CAN.

Automated Sequencing

Amplification products were purified using the PCR purification kit (Qiagen, 28159 Avenue Stanford, Valencia, Calif. 91355, USA) and automated sequencing was carried out using the Big Dye Terminator Cycle Sequencing kit (Applied Biosystems [ABI], Applied Biosystems, 850 Lincoln Center Drive, Foster City, Calif. 94404, USA) according to the manufacturer's instructions. Sequencing reactions were purified by isopropanol precipitation and analysed on an ABI PRISM 3100 Genetic Analyser. Mutations were described according to the established nomenclature system (Antonarakis et al, Hum Mat 11 1-3 (1998)).

Assays for Sequence Variants

All germline mutations in MYH and somatic mutations in APC were confirmed by sequencing two independent PCR products and/or dHPLC separated heteroduplexes, in forward and/or reverse directions. The germline mutations Y90X, G382D and E466X in MYH were further confirmed by restriction enzyme digestion (using RsaI, BglII and ApoI, respectively). The common polymorphism 972 C>G (H324Q) in exon 12 of MYH was assayed by sequencing.

Somatic APC Mutation Database and Statistical Analysis

A database of 503 somatic mutations observed in sporadic colo-rectal tumours, and 308 somatic mutations observed in FAP and AFAP associated colo-rectal tumours was compiled (Al-Tassan et al Nat Genet 30 227-232 (2002) and Example 1). Statistical analyses were carried out using Fisher's Exact and the chi-squared tests.

Results
Biallelic Germline Mutations in MYH

No germline APC truncating mutations were identified. Sequencing of the entire open reading frame (ORF) of MYH in these cases revealed seven patients with biallelic mutations (Table 6), six of which were presumed to be homozygous for MYH variants since no wild type allele could be detected upon sequence analysis.

One Pakistani case (MA27) was homozygous for the exon 3 nonsense mutation Y90X (270 C>A); two British cases (MA22 and MA34) were homozygous for the exon 7 missense mutation Y165C (494 A>G); one British case (MA25) was compound heterozygous for Y165C/G382D (1145 G>A); and three Indian cases (MA20, MA24 and MA26) were homozygous for the exon 14 nonsense mutation E466X (1396 G>T). No samples were available from any of the parents of these patients, all of whom were unaffected, or any other family members. No patients carried single mutant MYH alleles.

The recurrent MYH variants Y90X (2 mutations) and Y165C (5 mutations) were found in association with the G allele of the exon 12 polymorphism 972 C>G (H324Q), and the recurrent variant E466X (6 mutations) was always found in association with the C allele. Sequencing of the entire ORFs of OGG1 and MTH1 in the fourteen MYH negative cases did not identify any likely pathogenic changes.

TABLE 6

Biallelic germline MYH mutations in patients with multiple colo-rectal adenomas

| Patient | Exon | Nucleotide Change | Amino Acid Change | Ethnic Background |
|---|---|---|---|---|
| MA27 | 3 | 270 C > A | Y90X | Pakistani |
|  | 3 | 270 C > A | Y90X |  |
| MA22 | 7 | 494 A > G | Y165C | British |
|  | 7 | 494 A > G | Y165C |  |
| MA34 | 7 | 494 A > G | Y165C | British |
|  | 7 | 494 A > G | Y165C |  |
| MA25 | 7 | 494 A > G | Y165C | British |
|  | 13 | 1145 G > A | G382D |  |
| MA20 | 14 | 1396 G > T | E466X | Indian |
|  | 14 | 1396 G > T | E466X |  |
| MA24 | 14 | 1396 G > T | E466X | Indian |
|  | 14 | 1396 G > T | E466X |  |
| MA26 | 14 | 1396 G > T | E466X | Indian |
|  | 14 | 1396 G > T | E466X |  |

Identification of Somatic G:C→T:A Mutations in Colo-Rectal Tumours

Using denaturing high performance liquid chromatography (dHPLC) analysis, we sought somatic mutations in the APC gene in colo-rectal tumours isolated from the patients with biallelic germline MYH mutations.

A region of APC was screened, spanning codons 653 to 1589 which encompassed the mutation cluster region (MCR, codons 1286 to 1513, Miyoshi et al, Hum Mol Genet 1 229-233 (1992)), a known hotspot for somatic mutations (Fearnhead et al, Hum Mol Genet 10 721-733 (2001)). In total, 50 somatic mutations were identified of which 49 were G:C→T:A transversion mutations.

The proportion of somatic G:C→T:A transversion mutations in APC that were detected in colo-rectal tumours from patients with biallelic MYH mutations were compared to a database of 503 reported somatic APC mutations from sporadic colo-rectal adenomas and carcinomas, and 308 somatic mutations from FAP associated colo-rectal tumours. The excess of somatic G:C→T:A transversions in patients with biallelic MYH mutations was highly significant.

Sequence Surrounding the Somatic G:C→T:A Mutations

Examination of the sequence context surrounding the somatic G:C→T:A mutations revealed that the two bases immediately 3' to the mutated G were always AA, irrespective of the nature of the germline MYH mutations. The preponderance of G:C→T:A mutations at GAA sequences is highly significant, since other sequences that could undergo G:C→T:A mutation to stop codons are equally prevalent in the APC coding region (216 GAA sites vs 213 non-GAA sites, $\chi^2=13.28$, $P=2.7\times10^{-4}$).

Conclusions

In this study, another patient compound heterozygous for Y165C/G382D and two patients homozygous for Y165C have been identified. More significantly, four unrelated patients homozygous for nonsense mutations in MYH have been identified. Homozygosity for MYH variants (as opposed to a point mutation on one allele and a large deletion on the other allele) is considered highly likely, since one of the six patients was shown to be from a family with known consanguinity, and four patients were from Indian families, which are known to have a high frequency of first and second cousin marriages. None of the patients harboured truncating mutations in exon 4 or the alternatively spliced region of exon 9 of APC, which would have been consistent with AFAP, and none of the parents who carried single mutant MYH alleles, showed signs of CRC. Therefore, these data unequivocally confirm that biallelic inactivation of MYH predisposes to colo-rectal adenoma and carcinoma.

The recurrent mutations Y90X, Y165C and E466X cannot be readily explained in terms of the well characterised mechanisms of hypermutagenesis, and are associated with specific (and different) alleles of the polymorphism 972 C>G in exon 12 of MYH. These mutations are therefore probably not independent mutational events, but derived from the same ancestoral chromosomes. In total, four British families that are either homozygous for Y165C or compound heterozygous for Y165C/G382D, three Indian families that are homozygous for E466X and a single Indian or Pakistani family that is homozygous for Y90X have been identified. Different mutations in MYH may therefore be more frequent in different ethnic populations, consistent with founder effects, and diagnostic screening strategies may have to be optimised accordingly.

In this study, an unusually high frequency of somatic G:C→T:A mutations was observed in colo-rectal tumours from patients with biallelic MYH mutations, and this confirms the pathogenicity of the germline variants.

Together with the earlier study, likely pathogenic variants in the BER genes OGG1 or MTH1 have not been detected in over thirty cases with multiple colo-rectal adenoma and carcinoma.

In conclusion, the above Example provides evidence for a novel autosomal recessive colo-rectal tumour pre-disposition syndrome, and this is the first reported inherited disorder of base excision repair in humans.

Appendix 1

TABLE 1

Primers used for the amplification of exon 4 of APC.

| Primer name | Sequence | SEQ ID NO. |
|---|---|---|
| ex4F | 5'-TGCAGTCTTTATTAGCATTGTTT-3' | 5 |
| ex4R | 5'-TTCAAATAAGTTGTACTGCCAAG-3' | 6 |

TABLE 2

Primers used for the amplification of exon 15 of APC for DNA extracted from paraffin embedded tissue. The nucleotide numbers in the primer names are cited according to Accession number NM_000038 (Kinzler et al. 1991, Josyln et al. 1991). All primers were used at an annealing temperature of 50° C..

| Primer name | Sequence | SEQ ID NO. | Product size |
|---|---|---|---|
| APCintron14F1 | 5'-CTTCTATCCTTTTATTTGCTTGTT-3' | 133 | 232 bp |
| APC2136R1 | 5'-GCTAACTGCCCCCATGTC-3' | 134 | |
| APC2113F2 | 5'-CTAAAGACCAGGAAGCATTATG-3' | 135 | 281 bp |
| APC2375R2 | 5'-ATGAGATGCCTTGGGACTT-3' | 136 | |
| APC2327F3 | 5'-ATTAGATGCTCAGCACTTATCAGA-3' | 137 | 221 bp |
| APC2526R3 | 5'-ATGAAGAGGAGCTGGGTAACAC-3' | 138 | |
| APC2486F4 | 5'-TGGCAACATGACTGTCCTTTCA-3' | 139 | 242 bp |
| APC2706R4 | 5'-TGGCTGACACTTCTTCCATGAC-3' | 140 | |
| APC2657F5 | 5'-TTCAAAGCGAGGTTTGCAGATC-3' | 141 | 177 bp |
| APC2812R5 | 5'-GAATGTGTATGGGCAGCAGAGC-3' | 142 | |
| APC2785F6 | 5'-CAGATGAGAGAAATGCACTTAGAA-3' | 143 | 204 bp |
| APC2968R6 | 5'-CAATCGAGGGTTTCATTTGAC-3' | 144 | |
| APC2884F7 | 5'-TGCCTTATGCCAAATTAGAATA-3' | 145 | 162 bp |
| APC3027R7 | 5'-CGGCTGGGTATTGACCATA-3' | 146 | 162 bp |
| APC2968F8 | 5'-GTCAAATGAAACCCTCGATTGA-3' | 147 | 195 bp |
| APC3141R8 | 5'-TTTGCCTTCCAGAGTTCAACTG-3' | 148 | |
| APC3047F9 | 5'-CCTAGCCCATAAAATACATAGTGC-3' | 149 | 212 bp |
| APC3235R9 | 5'-TTGTACTTTGATTCCTTGATTGTC-3' | 150 | |
| APC3182F10 | 5'-ATGGGCAAGACCCAAACACATA-3' | 151 | 204 bp |
| APC3363R10 | 5'-CCCACTCGATTTGTTTCTGAACC-3' | 152 | |
| APC3332F11 | 5'-TGTTTCTCCATACAGGTCACG-3' | 153 | 240 bp |
| APC3551R11 | 5'-TCAATAGGCTGATCCACATGA-3' | 154 | |
| APC3460F12 | 5'-CCAATTATAGTGAACGTTACTCTG-3' | 155 | 247 bp |
| APC3686R12 | 5'-GATGAAGGTGTGGACGTATTC-3' | 156 | |
| APC3648F13 | 5'-CAAAGCAGTAAAACCGAACAT-3' | 157 | 277 bp |
| APC3903R13 | 5'-CTTCCTGTGTCGTCTGATTACA-3' | 158 | |
| APC3871F14 | 5'-CATCTTTGTCATCAGCTGAAGA-3' | 159 | 263 bp |
| APC4114R14 | 5'-ACCACTTTTGGAGGGAGATT-3' | 160 | |
| APC4001F15 | 5'-CGAAGTTCCAGCAGTGTCAC-3' | 161 | 245 bp |
| APC4227R15 | 5'-TGGCAATCGAACGACTCTC-3' | 162 | |
| APC4167F16 | 5'-GTTCAGGAGACCCCACTCAT-3' | 163 | 260 bp |
| APC4405R16 | 5'-CTCTTTTCAGCAGTAGGTGCTT-3' | 164 | |
| APC4379F17 | 5'-AACCAAGCGAGAAGTACCTAA-3' | 165 | 275 bp |
| APC4633R17 | 5'-ATTCTGTTTCATTCCCATTGT-3' | 166 | |
| APC4540F18 | 5'-CTTGTTCATCCAGCCTGAGT-3' | 167 | 265 bp |
| APC4786R18 | 5'-CGTGATGACTTTGTTGGCA-3' | 168 | |
| APC4658F19 | 5'-GCAGCCTAAAGAATCAAATGA-3' | 169 | 258 bp |
| APC4895R19 | 5'-GGTTGCAACCTGTTTTGTGAT-3' | 170 | |
| APC4850F27 | 5'-TGTGGCAAGGAAACCAAGTC-3' | 171 | 273 bp |
| APC5100R27 | 5'-CTGCCTTCTGTAGGAATGGTATC-3' | 172 | |
| APC5067F28 | 5'-GGAGGAGCACAGTCAGGTGA-3' | 173 | 245 bp |
| APC5292R28 | 5'-GAAGACGACGCAGATGCTTG-3' | 174 | |
| APC5251F29 | 5'-ACAAGCCTTTCCGTGTGA-3' | 175 | 217 bp |
| APC5445R29 | 5'-TCTTTGTTGTCTGAGAAAACTCT-3' | 176 | |
| APC5344F30 | 5'-AAAAGAAACCAACTTCACCAGT-3' | 177 | 248 bp |
| APC5571R30 | 5'-TCCTTCAATAGGCGTGTAATG-3' | 178 | |

TABLE 2-continued

Primers used for the amplification of exon 15 of APC for DNA extracted from paraffin embedded tissue. The nucleotide numbers in the primer names are cited according to Accession number NM_000038 (Kinzler et al. 1991, Josyln et al. 1991). All primers were used at an annealing temperature of 50° C..

| Primer name | Sequence | SEQ ID NO. | Product size |
|---|---|---|---|
| APC5550F31 | 5'-TTTGCTTTTGATTCACCTCA-3' | 179 | 262 bp |
| APC5791R31 | 5'-GTTTAGGCTGACCTCGATTTA-3' | 180 | |
| APC5709F32 | 5'-GAGGCTAAAGTTACCAGCCAC-3' | 181 | 266 bp |
| APC5953R32 | 5'-TTTTCTTGGTCAATGTCACTGA-3' | 182 | |
| APC5911F33 | 5'-ATACTCCAGTTTGCTTTTCTCAT-3' | 183 | 244 bp |
| APC6133R33 | 5'-AACAGGTCATCTTCAGAGTCAA-3' | 184 | |
| APC6049F34 | 5'-CATCAGGCTATGCTCCTAAAT-3' | 185 | 279 bp |
| APC6307R34 | 5'-CTGAATCAGGGGATAGACCAT-3' | 186 | |
| APC6239F35 | 5'-TATGGGTGGCATATTAGGTGA-3' | 187 | 246 bp |
| APC6465R35 | 5'-TGAAATGGTGATCCCAGAGA-3' | 188 | |
| APC6414F36 | 5'-AGACAAGCTTCGTCTGATTCA-3' | 189 | 264 bp |
| APC6658R36 | 5'-CATTTGGCCTGAAATTTCTG-3' | 190 | |
| APC6527F37 | 5'-AGGCCCACGAATTCTAAAA-3' | 191 | 247 bp |
| APC6751R37 | 5'-AGGACTTGTACTTGAGGAGCTAT-3' | 192 | |
| APC6726F38 | 5'-ATGATTCATATTCCAGGAGTTCG-3' | 193 | 261 bp |
| APC6970R38 | 5'-TGGTTGCTGGGCAGGTC-3' | 194 | |
| APC6942F39 | 5'-TCAGGATCTAGAGATTCGACCC-3' | 195 | 220 bp |
| APC7141R39 | 5'-GGCTCATCTGTCTACCTGGAG-3' | 196 | |
| APC7100F40 | 5'-TTCAACTAAGTCCTCAGGTTCT-3' | 197 | 269 bp |
| APC7348R40 | 5'-TGAAAGTTGACTGGCGTACTA-3' | 198 | |
| APC7309F41 | 5'-CAAGTGGAAGTGAATCTGATAGA-3' | 199 | 240 bp |
| APC7531R41 | 5'-ATCCACCAGCCTGAACAG-3' | 200 | |
| APC7463F42 | 5'-TAGGTCCCAGGCACAAACTC-3' | 201 | 262 bp |
| APC7705R42 | 5'-GCTTACTCGAGGAAGGGATG-3' | 202 | |
| APC7683F43 | 5'-CGTGAGCACAGCAAACATTC-3' | 203 | 256 bp |
| APC7920R43 | 5'-CACCTGAGGAAACGGTCTG-3' | 204 | |
| APC7852F44 | 5'-AAGTATCCGCAAAAGGAACAT-3' | 205 | 238 bp |
| APC8072R44 | 5'-TCAATCACCGGGGGAGTA-3' | 206 | |
| APC8025F45 | 5'-GACTGTCCCATTAACAATCCTAG-3' | 207 | 238 bp |
| APC8241R45 | 5'-GTCCTGGTTTTATCTCAGTTCC-3' | 208 | |
| APC8165F46 | 5'-CAGTGTTCCCATGCGTACC-3' | 209 | 263 bp |
| APC8407R46 | 5'-TATCTGCGCTGCTTTTCCTAG-3' | 210 | |
| APC8371F47 | 5'-CTGCCAGAGTGACTCCTTTT-3' | 211 | 285 bp |
| APC8632R47 | 5'-TCTTTTAAAGTTTCATTTGAAACA-3' | 212 | |

TABLE 3

Primers used for the amplification of CTNNB1. All primers were used at an annealing temperature of 50° C..

| Exon | Name | Primer sequence | SEQ ID NO. | Product size |
|---|---|---|---|---|
| 2 | b cat2F | 5'-AGGTCTGCGTTTCACTAACCT-3' | 213 | 244 bp |
| | b cat2R | 5'-AGCCCCAATTCAGTAACTAAAG-3' | 214 | |

TABLE 3-continued

Primers used for the amplification of CTNNB1.
All primers were used at an annealing
temperature of 50° C..

| Exon | Name | Primer sequence | SEQ ID NO. | Product size |
|---|---|---|---|---|
| 3 | b cat3F1 | 5'-CATCTGCTTTCTTGGCTGTC-3' | 215 | 280 bp |
|   | b cat3R1 | 5'-AGGATTGCCTTTACCACTCAG-3' | 216 |   |
|   | b cat3F2 | 5'-GTTAGTCACTGGCAGCAACAG-3' | 217 | 230 bp |
|   | b cat3R2 | 5'-CTCAAAACTGCATTCTGACTTTC-3' | 218 |   |
| 4 | b cat4F1 | 5'-TGCTGAACTGTGGATAGTGAGTG-3' | 219 | 162 bp |
|   | b cat4R1 | 5'-TAGTGGGATGAGCAGCATCAA-3' | 220 |   |
|   | b cat4F2 | 5'-GCTGCTATGTTCCCTGAGACAT-3' | 221 | 260 bp |
|   | b cat4R2 | 5'-TGAGCATTTACTTCAAAGCAGACT-3' | 222 |   |
| 5 | b cat5F1 | 5'-AGGGGAGTAGTTTCAGAATGTCT-3' | 223 | 248 bp |
|   | b cat5R1 | 5'-GGGAAAGGTTATGCAAGGTC-3' | 224 |   |
|   | b cat5F2 | 5'-AGATGGTGTCTGCTATTGTACGT-3' | 225 | 227 bp |
|   | b cat5R2 | 5'-GCCTCATCAGAAATATTGTGAGT-3' | 226 |   |
| 6 | b cat6F | 5'-ACTCACAATATTTCTGATGAGGC-3' | 227 | 289 bp |
|   | b cat6R | 5'-AGGTGTCCAATGCTCCATG-3' | 228 |   |
| 7 | b cat7F | 5'-AAAATAGGTTGGTAATATGGCTC-3' | 229 | 271 bp |
|   | b cat7R | 5'-TGCAGATGCTATACACAAGACTC-3' | 230 |   |
| 8 | b cat8F | 5'-AGGATTGATAGGCACTTCTAGCT-3' | 231 | 219 bp |
|   | b cat8R | 5'-CAAGCACATACTCATCTTGACTCT-3' | 232 |   |
| 9 | b cat9F1 | 5'-AGAGTCAAGATGAGTATGTGCTTG-3' | 233 | 218 bp |
|   | b cat9R1 | 5'-CAGTACGCACAAGAGCCTCTA-3' | 234 |   |
|   | b cat9F2 | 5'-ATAAGAACAAGATGATGGTCTGC-3' | 235 | 270 bp |
|   | b cat9R2 | 5'-CAATTCTGCAACAAAGGTAAATT-3' | 236 |   |
| 10 | b cat10F | 5'-GATTTTGTTGAGTTGTATGCCA-3' | 237 | 240 bp |
|   | b cat10R | 5'-TTTTAGATAGCCAGGTATCACTG-3' | 238 |   |
| 11 | b cat11F | 5'-TACGGGGAACTTCGGGTA-3' | 239 | 263 bp |
|   | b cat11R | 5'-TGGACATAAAACCTAGAACACTTC-3' | 240 |   |
| 12 | b cat12F | 5'-GGCTTGCCATGTTTTAGCTT-3' | 241 | 243 bp |
|   | b cat12R | 5'-ACATCTGCTAAAGGCTTTGGT-3' | 242 |   |
| 13 | b cat13F | 5'-AAGTCTCAGTTTTTCCTCAAGG-3' | 243 | 197 bp |
|   | b cat13R | 5'-CCAGATAAATAACTGCTCACATT-3' | 244 |   |
| 14 | b cat14F | 5'-CCTTGCTTTGTGCATGTTTA-3' | 245 | 122 bp |
|   | b cat14R | 5'-TGATCTGGAGTTAATCGAGAAA-3' | 246 |   |
| 15 | b cat15F | 5'-TTTTGTTGACACCCTGACTCTT-3' | 247 | 286 bp |
|   | b cat15R | 5'-AAAGTATTTTACCCAAACTGGC-3' | 248 |   |

TABLE 4

Primers used for the amplification of TP53.
Part of exon 4 and all of exons 5-9 were amplified
using the primers designed by Dahiya et al. 1996
(Br. J. Cancer 74, 264-268).

| Exon | Primer name | Sequence | SEQ ID NO. | Product size | Annealing Temp. |
|---|---|---|---|---|---|
| 2 | P53_2F | 5'-CCTCTTGCAGCAGCCAGACT-3' | 249 | 215 bp | 57° C. |
|   | P53_2R | 5'-AGCAGAAAGTCAGTCCCATGAAT-3' | 250 |   |   |
| 3 | P53_3F | 5'-AGCGAAAATTCATGGGACTGA-3' | 251 | 204 bp | 50° C. |
|   | P53_3R | 5'-TCCGGGGACAGCATCAAAT-3' | 252 |   |   |
| 4 | P53_4F1 | 5'-CTCTTTTCACCCATCTACAGTCC-3' | 253 | 225 bp | 57° C. |
|   | P53_4F1 | 5'-TCTGGGAAGGGACAGAAGAT-3' | 254 |   |   |
| 10 | P53_10F | 5'-GTTGCTTTTGATCCGTCATAAA-3' | 255 | 233 bp | 54° C. |
|   | P53_10R | 5'-AGGAAGGGGCTGAGGTCAC-3' | 256 |   |   |

TABLE 4-continued

Primers used for the amplification of TP53.
Part of exon 4 and all of exons 5-9 were amplified
using the primers designed by Dahiya et al. 1996
(Br. J. Cancer 74, 264-268).

| Exon | Primer name | Sequence | SEQ ID NO. | Product size | Annealing Temp. |
|---|---|---|---|---|---|
| 11 | P53_11F | 5'-ACCCTCTCACTCATGTGATGTCA-3' | 257 | 250 bp | 50° C. |
|    | P53_11R | 5'-GTGCTTCTGACGCACACCTATT-3' | 258 | | |

TABLE 5

Primers used for the amplification of hMYH

| Exon | Primer name | Sequence | SEQ ID NO. | Product size | Annealing Temp. |
|---|---|---|---|---|---|
| 1 | Y1F | 5'-GAAGCTGCGGGAGCTGAAA-3' | 52 | 133 bp | 60° C. |
|   | Y1R | 5'-ATCCCCGACTGCCTGAACC-3' | 53 | | |
| 2 | Y2F | 5'-CTGCATTTGGCTGGGTCTTT-3' | 54 | 263 bp | 54° C. |
|   | Y2R | 5'-CGCACCTGGCCCTTAGTAAG-3' | 55 | | |
| 3 | Y3F | 5'-AGCCTGTGCAGGGATGATTG-3' | 56 | 272 bp | 57° C. |
|   | Y3R | 5'-CAACCCCAGATGAGGAGTTAGG-3' | 57 | | |
| 4 | Y4F | 5'-CTCATCTGGGGTTGCATTGA-3' | 58 | 167 bp | 57° C. |
|   | Y4R | 5'-GGGTTGGCATGAGGACACTG-3' | 59 | | |
| 5 | Y5F | 5'-GGGCAGGTCAGCAGTGTC-3' | 60 | 189 bp | 57° C. |
|   | Y5R | 5'-TACACCCACCCCAAAGTAGA-3' | 61 | | |
| 6 | Y6F | 5'-TACTTTGGGGTGGGTGTAGA-3' | 62 | 185 bp | 54° C. |
|   | Y6R | 5'-AAGAGATCACCCGTCAGTCC-3' | 63 | | |
| 7 | Y7F | 5'-GGGACTGACGGGTGATCTCT-3' | 64 | 186 bp | 54° C. |
|   | Y7R | 5'-TTGGAGTGCAAGACTCAAGATT-3' | 65 | | |
| 8 | Y8F | 5'-CCAGGAGTCTTGGGTGTCTT-3' | 66 | 240 bp | 57° C. |
|   | Y8R | 5'-AGAGGGGCCAAAGAGTTAGC-3' | 67 | | |
| 9 | Y9F | 5'-AACTCTTTGGCCCCTCTGTG-3' | 68 | 196 bp | 57° C. |
|   | Y9R | 5'-GAAGGGAACACTGCTGTGAAG-3' | 69 | | |
| 10 | Y10F | 5'-GTGCTTCAGGGGTGTCTGC-3' | 70 | 262 bp | 57° C. |
|    | Y10R | 5'-TGTCATAGGGCAGAGTCACTCC-3' | 71 | | |
| 11 | Y11F | 5'-TAAGGAGTGACTCTGCCCTATG-3' | 72 | 248 bp | 54° C. |
|    | Y11R | 5'-GCCAAGAGGGGCTTTAGG-3' | 73 | | |
| 12 | Y12F | 5'-AGCCCCTCTTGGCTTGAGTA-3' | 74 | 298 bp | 57° C. |
|    | Y12R | 5'-TGCCGATTCCCTCCATTCT-3' | 75 | | |
| 13 | Y13F | 5'-AGGGCAGTGGCATGAGTAAC-3' | 76 | 242 bp | 57° C. |
|    | Y13R | 5'-GGCTATTCCGCTGCTCACTT-3' | 77 | | |
| 14 | Y14F | 5'-TTGGCTTTTGAGGCTATATCC-3' | 78 | 256 bp | 54° C. |
|    | Y14R | 5'-CATGTAGGAAACACAAGGAAGTA-3' | 79 | | |
| 15 | Y15F | 5'-TGAAGTTAAGGGCAGAACACC-3' | 80 | 205 bp | 54° C. |
|    | Y15R | 5'-GTTCACCCAGACATTCGTTAGT-3' | 81 | | |
| 16 | Y16F | 5'-AGGACAAGGAGAGGATTCTCTG-3' | 82 | 224 bp | 54° C. |
|    | Y16R | 5'-GGAATGGGGGCTTTCAGA-3' | 83 | | |

TABLE 6

Primers used for the amplification of hOGG1

| Exon | Primer name | Sequence | SEQ ID NO. | Product size | Annealing Temp. |
|---|---|---|---|---|---|
| 1 | M1F | 5'-CTTTGGGCGTCGACGAG-3' | 84 | 237 bp | 57° C. |
|   | M1R | 5'-GAGGGGACAGGCTTCTCAG-3' | 85 | | |
| 2 | M2F1 | 5'-ATTGAGTGCCAGGGTTGTCA-3' | 86 | 245 bp | 57° C. |
|   | M2R1 | 5'-CGGAACCCCAGTGGTGATAC-3' | 87 | | |
|   | M2F2 | 5'-TGTACTAGCGGATCAAGTAT-3' | 88 | 286 bp | 50° C. |
|   | M2R2 | 5'-TGGCAAAACTGAGTCATAG-3' | 89 | | |
| 3 | M3F1 | 5'-GTCTGGTGTTGCTTTCTCTAAC-3' | 90 | 229 bp | 50° C. |
|   | M3R1 | 5'-GTGATGCGGGCGATGTT-3' | 91 | | |
|   | M3F2 | 5'-TCTCCAGGTGTGCGACTGC-3' | 92 | 275 bp | 57° C. |
|   | M3R2 | 5'-AGGAAGCCTTGAGAAGGTAACC-3' | 93 | | |
| 4 | M4F | 5'-GGAAGAACTTGAAGATGCCT-3' | 94 | 296 bp | 55° C. |
|   | M4R | 5'-GCTCATTTCCTGCTCTCC-3' | 95 | | |
| 5 | M5F | 5'-CCGGCTTTGGGGCTATA-3' | 96 | 279 bp | 57° C. |
|   | M5R | 5'-GTTTCTACCATCCCAGCCCA-3' | 97 | | |
| 6 | M6F | 5'-TACTTCTGTTGATGGGTCAC-3' | 98 | 153 bp | 55° C. |
|   | M6R | 5'-TGGAGGAGAGGAAACCTAG-3' | 99 | | |
| 7 | M7F | 5'-ACCTCCCAACACTGTCACTA-3' | 100 | 265 bp | 55° C. |
|   | M7R | 5'-CCCTCCCCAACATGAGA-3' | 101 | | |
| 8 | M8F1 | 5'-CTGTGGCCCACGCACTTGTG-3' | 102 | 253 bp | 57° C. |
|   | M8R1 | 5'-ACGTCCTTGGTCCAGCAGTGGT-3' | 103 | | |
|   | M8F2 | 5'-GAGAGGGGATTCACAAGGTG-3' | 104 | 287 bp | 55° C. |
|   | M8R2 | 5'-GCCATTAGCTCCAGGCTTAC-3' | 105 | | |

TABLE 7

Primers used for the amplification of hMTH

| Exon | Primer Name | Sequence | SEQ ID NO. | Product size | Annealing Temp. |
|---|---|---|---|---|---|
| 2 | T2F | 5'-GCAAGGACAGAGGGCTTTCTG-3' | 106 | 249 bp | 67° C. |
|   | T2R | 5'-CCAGCAGGCCATCAACTGAT-3' | 107 | | |
| 3 | T3F | 5'-GCACGTCATGGCTGACTCT-3' | 108 | 246 bp | 57° C. |
|   | T3R | 5'-CTGGGAAAGCCGGTTCTAT-3' | 109 | | |
| 4 | T4F | 5'-TCCCTGGGCTGTGTGTAGAT-3' | 110 | 298 bp | 57° C. |
|   | T4R | 5'-GAGATGGGACCCGCATAGT-3' | 111 | | |
| 5 | T5F | 5'-TGAAGTTTGGGTTGCACCTC-3' | 112 | 281 bp | 57° C. |
|   | T5R | 5'-AGATGGTTTGCGGCTGTTC-3' | 113 | | |

TABLE 8

LD-PCR primers used for the amplification of exon 15 of APC for DNA extracted from fresh tissue. Primer nucleotide numbers in parentheses are cited according to Accession No. NM_000038.

| Primer name | Sequence | SEQ ID NO. | Product Size |
|---|---|---|---|
| N15F (1997) | 5'-GCAAATCCTAAGAGAGAACAACTGT-3' | 7 | 6.67 kb |
| N15R1 (8684) | 5'-TCCAGAACAAAAACCCTCTAACAAG-3' | 8 | |
| N15F (1997) | 5'-GCAAATCCTAAGAGAGAACAACTGT-3' | 7 | 3.59 kb |
| NS15 4R (5571) | 5'-CCTTCAATAGGCGTGTAATG-3' | 9 | |
| NS15 3F (3649) | 5'-AAAGCAGTAAAACCGAACAT-3' | 10 | 5.07 kb |
| N15R (8698) | 5'-TCAAATATGGCTTCCAGAACAAA-3' | 11 | |

TABLE 9

LD-PCR primers used for the amplification of exons 10 to 16 of hMYH.

| Primer name | Sequence | SEQ ID NO. | Product Size |
|---|---|---|---|
| Y10F1L | 5'-GCTGATCCCAGCAGCACCCTTGTTT-3' | 12 | 3.1 kb |
| Y16RL | 5'-AATGGGGGCTTTCAGAGGTGTCACT-3' | 13 | |

TABLE 10

Primers used for RT-PCR analysis.

| Region amplified | Primer name | Sequence | SEQ ID NO. |
|---|---|---|---|
| Exons 3-12 of APC | APCFEx3 | 5'-GAGGGTTTGTAAATGGAAGCAG-3' | 14 |
| | APCjREx11-12 | 5'-CTCATGCAGCCTTTCATAGAGC-3' | 15 |
| Exons 12-14 of Hmyh | rY12F | 5'-GTGGTCAACTTCCCCAGAAA-3' | 16 |
| Exons 12-14 of hMYH | rY14R | 5'-GGCCAGCCCATATACTTGAT-3' | 17 |

TABLE 11

Bi-directional sequencing reactions for automated sequencing of RT-PCR product clones spanning exons 1-14 of APC.

| Reaction | Primer name | Sequence | SEQ ID NO. |
|---|---|---|---|
| 1 | NS1_14F (39) | 5'-ATGGCTGCAGCTTCATATGA-3' | 18 |
| | NS1_14R2 (1049) | 5'-GCTGTCTTGGGAGCTAGAC-3' | 19 |
| 2 | NS1_14F2 (892) | 5'-ACCATGAAACAGCCAGTGT-3' | 20 |
| | NS1_14R (1978) | 5'-CTGTGGTCCTCATTTGTAG-3' | 21 |

TABLE 12

Bi-directional sequencing reactions for automated sequencing of LD-PCR products and clones spanning exon 15 of APC.

| Reaction | Primer name | Sequence | SEQ ID NO. |
|---|---|---|---|
| 1 | NS15 1F (1997) | 5'-GCAAATCCTAAGAGAGAACA-3' | 22 |
| | NS15 8R (3146) | 5'-GACTTTGCCTTCCAGAGTTC-3' | 23 |
| 2 | NS15 2F (2810) | 5'-AAGCTCTGCTGCCCATACACA-3' | 24 |
| | NS15 7R (3935) | 5'-CTGCTATTTGCAGGGTATTA-3' | 25 |
| 3 | NS15 3F (3649) | 5'-AAAGCAGTAAAACCGAACAT-3' | 26 |
| | NS15 3R (4775) | 5'-TTGTTGGCATGGCAGAAATA-3' | 27 |
| 4 | NS15 4F (4480) | 5'-TTCTTCCAGATGCTGATACT-3' | 28 |
| | NS15 4R (5571) | 5'-CCTTCAATAGGCGTGTAATG-3' | 29 |
| 5 | NS15 5F (5234) | 5'-GCCCAAAGGGAAAAGTCACA-3' | 30 |
| | NS15 5R (6346) | 5'-ATTTGCACCTTCCTGAATAG-3' | 31 |
| 6 | NS15 6F (6015) | 5'-CCTGACTCACAGGGAGAAC-3' | 32 |
| | NS15 6R (7135) | 5'-CTGTCTACCTGGAGATGTAT-3' | 33 |
| 7 | NS15 7F (6807) | 5'-GCCTCCAAAAGCCCTAGTGA-3' | 34 |
| | NS15 2R (7920) | 5'-AGCACCTGAGGAAACGGTCTG-3' | 35 |
| 8 | NS15 8F (7552) | 5'-GAAAACTCCCACCTAATCTC-3' | 36 |
| | NS15 1R (8684) | 5'-AACAAAAACCCTCTAACAAG-3' | 37 |

TABLE 13

Primers used to assay for E1317Q

| Primer name | Sequence | SEQ ID NO. |
|---|---|---|
| E1317QLF (3652) | 5'-GCAGTAAAACCGAACATATG-3' | 38 |
| E1317QR (4137) | 5'-TGGACTTTTGGGTGTCTG-3' | 39 |
| E1317QSF (3934) | 5'-CTAATACCCTGCAAATAGCA-3' | 40 |
| E1317QR (4137) | 5'-TGGACTTTTGGGTGTCTG-3' | 39 |

TABLE 14

Assays for missense variants in hMYH.
All ARMS reactions incorporated internal control primers (AJ31 and AJ32, Jones et al. 2000) to validate the assay.

| Variant | Exon | Assay | SEQ ID NO. |
|---|---|---|---|
| V22M (66 G→A) | 2 | NcoI digest | |
| Y165C (494 A→G) | 7 | Normal ARMS (165N 5'-CGCCGGCCACGAGAATGGT-3') | 41 |
| | | Mutant ARMS (165M 5'-CGCCGGCCACGAGAATTGC-3') | 42 |
| | | Common (165C 5'-AGTGCTTCCCTGGAGGTGAGA-3') | 43 |
| R260Q (779 G→A) | 10 | Normal ARMS (260N 5'-CTTGGTTGAAATCTCCTGCCC-3') | 44 |
| | | Mutant ARMS (260M 5'-CTTGGTTGAAATCTCCTGACT-3') | 45 |
| | | Common (260C 5'-CGAGCCATTGGTGCTGATC-3') | 46 |
| H324Q (972 C→G) | 12 | Normal ARMS (324N 5'-CCAGCTCCCAACACTGGAGAC-3') | 124 |
| | | Mutant ARMS (324M 5'-CCAGCTCCCAACACTGGAGAG-3') | 125 |
| | | Common (324C 5'-CCCAGGCTGTTCCAGAACAC-3') | 126 |
| G382D (1145 G→A) | 13 | BglII digest | |
| S501F (1502 C→T) | 16 | Normal ARMS (501N 5'-GCTTTTTCCGACTGCACGCAG-3') | 47 |
| | | Mutant ARMS (501M 5'-GCTTTTTCCGACTGCACGAAA-3') | 48 |
| | | Common (501C 5'-GCATTCCAGGCTAAGCCTAGC-3') | 49 |

TABLE 15

Primers used for site directed mutagenesis of mutY

| Mutation | Primer name | Sequence | SEQ ID NO. |
|---|---|---|---|
| Y82C | Y82C_F | 5'-GCGCGCGCGGGCGCAATAGCCAAGCCC-3' | 50 |
| G253D | G253D_F | 5'-CCGCCCCACAAGTCGCTCGGCGGACGC-3' | 51 |

Appendix 2

Y165C Mutant Sequence

Mutant hMYH sequence: 494 A to G (Y165C) mutant. The mutant codon and amino acid indicated in bold and underlined (Single letter amino acid sequence (SEQ ID NO. 1) above and cDNA sequence (SEQ ID NO. 130) below).

```
    M   T   P   L   V   S   R   L   S   R   L   W   A    13
   ATG ACA CCG CTC GTC TCC CGC CTG AGT CGT CTG TGG GCC    39

I   M   R   K   P   R   A   A   V   G   S   G   H    26
   ATC ATG AGG AAG CCA CGA GCA GCC GTG GGA AGT GGT CAC    78

R   K   Q   A   A   S   Q   E   G   R   Q   K   H    39
   AGG AAG CAG GCA GCC AGC CAG GAA GGG AGG CAG AAG CAT   117

A   K   N   N   S   Q   A   K   P   S   A   C   D    52
   GCT AAG AAC AAC AGT CAG GCC AAG CCT TCT GCC TGT GAT   156

G   L   A   R   Q   P   E   E   V   L   Q   A        65
   GGC CTG GCC AGG CAG CCG GAA GAG GTG GTA TTG CAG GCC   195

S   V   S   S   Y   H   L   F   R   D   V   A   E    78
   TCT GTC TCC TCA TAC CAT CTA TTC AGA GAC GTA GCT GAA   234

V   T   A   F   R   G   S   L   L   S   W   Y   D    91
   GTC ACA GCC TTC CGA GGG AGC CTG CTA AGC TGG TAC GAC   273

Q   E   K   R   D   L   P   W   R   R   R   A   E   104
   CAA GAG AAA CGG GAC CTA CCA TGG AGA AGA CGG GCA GAA   312

D   E   M   D   L   D   R   R   A   Y   A   V   W   117
   GAT GAG ATG GAC CTG GAC AGG CGG GCA TAT GCT GTG TGG   351

V   S   E   V   M   L   Q   Q   T   Q   V   A   T   130
   GTC TCA GAG GTC ATG CTG CAG CAG ACC CAG GTT GCC ACT   390

V   I   N   Y   Y   T   G   W   M   Q   K   W   P   143
   GTG ATC AAC TAC TAT ACC GGA TGG ATG CAG AAG TGG CCT   429
```

```
              T   L   Q   D   L   A   S   A   S   L   E   E   V   156
             ACA CTG CAG GAC CTG GCC AGT GCT TCC CTG GAG GAG GTG    468
              N   Q   L   W   A   G   L   G  [C]  Y   S   R   G   169
             AAT CAA CTC TGG GCT GGC CTG GGC TGC TAT TCT CGT GGC    507
              R   R   L   Q   E   G   A   R   K   V   V   E   E   182
             CGG CGG CTG CAG GAG GGA GCT CGG AAG GTG GTA GAG GAG    546
              L   G   G   H   M   P   R   T   A   E   T   L   Q   195
             CTA GGG GGC CAC ATG CCA CGT ACA GCA GAG ACC CTG CAG    585
              Q   L   L   P   G   V   G   R   Y   T   A   G   A   208
             CAG CTC CTG CCT GGC GTG GGG CGC TAC ACA GCT GGG GCC    624
              I   A   S   I   A   F   G   Q   A   T   G   V   V   221
             ATT GCC TCT ATC GCC TTT GGC CAG GCA ACC GGT GTG GTG    663
              D   G   N   V   A   R   V   L   C   R   V   R   A   234
             GAT GGC AAC GTA GCA CGG GTG CTG TGC CGT GTC CGA GCC    702
              I   G   A   D   P   S   S   T   L   V   S   Q   Q   247
             ATT GGT GCT GAT CCC AGC AGC ACC CTT GTT TCC CAG CAG    741
              L   W   G   L   A   Q   Q   L   V   D   P   A   R   260
             CTC TGG GGT CTA GCC CAG CAG CTG GTG GAC CCA GCC CGG    780
              P   G   D   F   N   Q   A   A   M   E   L   G   A   273
             CCA GGA GAT TTC AAC CAA GCA GCC ATG GAG CTA GGG GCC    819
              T   V   C   T   P   Q   R   P   L   C   S   Q   C   286
             ACA GTG TGT ACC CCA CAG CGC CCA CTG TGC AGC CAG TGC    858
              P   V   E   S   L   C   R   A   R   Q   R   V   E   299
             CCT GTG GAG AGC CTG TGC CGG GCA CGC CAG AGA GTG GAG    897
              Q   E   Q   L   L   A   S   G   S   L   S   G   S   312
             CAG GAA CAG CTC TTA GCC TCA GGG AGC CTG TCG GGC AGT    936
              P   D   V   E   E   C   A   P   N   T   G   Q   C   325
             CCT GAC GTG GAG GAG TGT GCT CCC AAC ACT GGA CAG TGC    975
              H   L   C   L   P   P   S   E   P   W   D   Q   T   338
             CAC CTG TGC CTG CCT CCC TCG GAG CCC TGG GAC CAG ACC   1014
              L   G   V   V   N   F   P   R   K   A   S   R   K   351
             CTG GGA GTG GTC AAC TTC CCC AGA AAG GCC AGC CGC AAG   1053
              P   P   R   E   E   S   S   A   T   C   V   L   E   364
             CCC CCC AGG GAG GAG AGC TCT GCC ACC TGT GTT CTG GAA   1092
              Q   P   G   A   L   G   A   Q   I   L   L   V   Q   377
             CAG CCT GGG GCC CTT GGG GCC CAA ATT CTG CTG GTG CAG   1131
              R   P   N   S   G   L   L   A   G   L   W   E   F   390
             AGG CCC AAC TCA GGT CTG CTG GCA GGA CTG TGG GAG TTC   1170
              P   S   V   T   W   E   P   S   E   Q   L   Q   R   403
             CCG TCC GTG ACC TGG GAG CCC TCA GAG CAG CTT CAG CGC   1209
              K   A   L   L   Q   E   L   Q   R   W   A   G   P   416
             AAG GCC CTG CTG CAG GAA CTA CAG CGT TGG GCT GGG CCC   1248
              L   P   A   T   H   L   R   H   L   G   E   V   V   429
             CTC CCA GCC ACG CAC CTC CGG CAC CTT GGG GAG GTT GTC   1287
              H   T   F   S   H   I   K   L   T   Y   Q   V   Y   442
             CAC ACC TTC TCT CAC ATC AAG CTG ACA TAT CAA GTA TAT   1326
              G   L   A   L   E   G   Q   T   P   V   T   T   V   455
             GGG CTG GCC TTG GAA GGG CAG ACC CCA GTG ACC ACC GTA   1365
              P   P   G   A   R   W   L   T   Q   E   E   F   H   468
             CCA CCA GGT GCT CGC TGG CTG ACG CAG GAG GAA TTT CAC   1404
              T   A   A   V   S   T   A   M   K   K   V   F   R   481
             ACC GCA GCT GTT TCC ACC GCC ATG AAA AAG GTT TTC CGT   1443
              V   Y   Q   G   Q   Q   P   G   T   C   M   G   S   494
             GTG TAT CAG GGC CAA CAG CCA GGG ACC TGT ATG GGT TCC   1482
              K   R   S   Q   V   S   S   P   C   S   R   K   K   407
             AAA AGG TCC CAG GTG TCC TCT CCG TGC AGT CGG AAA AAG   1521
              P   R   M   G   Q   Q   V   L   D   N   F   F   R   520
             CCC CGC ATG GGC CAG CAA GTC CTG GAT AAT TTC TTT CGG   1560
              S   H   I   S   T   D   A   H   S   L   N   S   A   533
             TCT CAC ATC TCC ACT GAT GCA CAC AGC CTC AAC AGT GCA   1599
              A   Q   *                                             535
             GCC CAG TGA                                           1608
```

E466X Mutant Sequence

Mutant hMYH sequence: 1396 G to T (E466X) mutant. The mutant codon and amino acid indicated in bold and underlined (Single letter amino acid sequence (SEQ ID NO. 3) above and cDNA sequence (SEQ ID NO. 131) below).

```
  M   T   P   L   V   S   R   L   S   R   L   W   A    13
ATG ACA CCG CTC GTC TCC CGC CTG AGT CGT CTG TGG GCC    39

I   M   R   K   P   R   A   A   V   G   S   G   H    26
ATC ATG AGG AAG CCA CGA GCA GCC GTG GGA AGT GGT CAC    78

R   K   Q   A   A   S   Q   E   G   R   Q   K   H    39
AGG AAG CAG GCA GCC AGC CAG GAA GGG AGG CAG AAG CAT   117

A   K   N   N   S   Q   A   K   P   S   A   C   D    52
GCT AAG AAC AAC AGT CAG GCC AAG CCT TCT GCC TGT GAT   156

G   L   A   R   Q   P   E   E   V   V   L   Q   A    65
GGC CTG GCC AGG CAG CCG GAA GAG GTG GTA TTG CAG GCC   195

S   V   S   S   Y   H   L   F   R   D   V   A   E    78
TCT GTC TCC TCA TAC CAT CTA TTC AGA GAC GTA GCT GAA   234

V   T   A   F   R   G   S   L   L   S   W   Y   D    91
GTC ACA GCC TTC CGA GGG AGC CTG CTA AGC TGG TAC GAC   273

Q   E   K   R   D   L   P   W   R   R   R   A   E   104
CAA GAG AAA CGG GAC CTA CCA TGG AGA AGA CGG GCA GAA   312

D   E   M   D   L   D   R   R   A   Y   A   V   W   117
GAT GAG ATG GAC CTG GAC AGG CGG GCA TAT GCT GTG TGG   351

V   S   E   V   M   L   Q   Q   T   Q   V   A   T   130
GTC TCA GAG GTC ATG CTG CAG CAG ACC CAG GTT GCC ACT   390

V   I   N   Y   Y   T   G   W   M   Q   K   W   P   143
GTG ATC AAC TAC TAT ACC GGA TGG ATG CAG AAG TGG CCT   429

T   L   Q   D   L   A   S   A   S   L   E   E   V   156
ACA CTG CAG GAC CTG GCC AGT GCT TCC CTG GAG GAG GTG   468

N   Q   L   W   A   G   L   G   Y   Y   S   R   G   169
AAT CAA CTC TGG GCT GGC CTG GGC TAC TAT TCT CGT GGC   507

R   R   L   Q   E   G   A   R   K   V   V   E   E   182
CGG CGG CTG CAG GAG GGA GCT CGG AAG GTG GTA GAG GAG   546

L   G   G   H   M   P   R   T   A   E   T   L   Q   195
CTA GGG GGC CAC ATG CCA CGT ACA GCA GAG ACC CTG CAG   585

Q   L   L   P   G   V   G   R   Y   T   A   G   A   208
CAG CTC CTG CCT GGC GTG GGG CGC TAC ACA GCT GGG GCC   624

I   A   S   I   A   F   G   Q   A   T   G   V   V   221
ATT GCC TCT ATC GCC TTT GGC CAG GCA ACC GGT GTG GTG   663

D   G   N   V   A   R   V   L   C   R   V   R   A   234
GAT GGC AAC GTA GCA CGG GTG CTG TGC CGT GTC CGA GCC   702

I   G   A   D   P   S   S   T   L   V   S   Q   Q   247
ATT GGT GCT GAT CCC AGC AGC ACC CTT GTT TCC CAG CAG   741

L   W   G   L   A   Q   Q   L   V   D   P   A   R   260
CTC TGG GGT CTA GCC CAG CAG CTG GTG GAC CCA GCC CGG   780

P   G   D   F   N   Q   A   M   E   L   G   A       273
CCA GGA GAT TTC AAC CAA GCA GCC ATG GAG CTA GGG GCC   819

T   V   C   T   P   Q   R   P   L   C   S   Q   C   286
ACA GTG TGT ACC CCA CAG CGC CCA CTG TGC AGC CAG TGC   858

P   V   E   S   L   C   R   A   R   Q   R   V   E   299
CCT GTG GAG AGC CTG TGC CGG GCA CGC CAG AGA GTG GAG   897

Q   E   Q   L   L   A   S   G   S   L   S   G   S   312
CAG GAA CAG CTC TTA GCC TCA GGG AGC CTG TCG GGC AGT   936

P   D   V   E   E   C   A   P   N   T   G   Q   C   325
CCT GAC GTG GAG GAG TGT GCT CCC AAC ACT GGA CAG TGC   975

H   L   C   L   P   P   S   E   P   W   D   Q   T   338
CAC CTG TGC CTG CCT CCC TCG GAG CCC TGG GAC CAG ACC  1014

L   G   V   V   N   F   P   R   K   A   S   R   K   351
CTG GGA GTG GTC AAC TTC CCC AGA AAG GCC AGC CGC AAG  1053
```

```
                                           -continued
  P   P   R   E   E   S   S   A   T   C   V   L   E   364
CCC CCC AGG GAG GAG AGC TCT GCC ACC TGT GTT CTG GAA 1092

Q   P   G   A   L   G   A   Q   I   L   L   V   Q   377
CAG CCT GGG GCC CTT GGG GCC CAA ATT CTG CTG GTG CAG 1131

R   P   N   S   G   L   L   A   G   L   W   E   F   390
AGG CCC AAC TCA GGT CTG CTG GCA GGA CTG TGG GAG TTC 1170

P   S   V   T   W   E   P   S   E   Q   L   Q   R   403
CCG TCC GTG ACC TGG GAG CCC TCA GAG CAG CTT CAG CGC 1209

K   A   L   L   Q   E   L   Q   R   W   A   G   P   416
AAG GCC CTG CTG CAG GAA CTA CAG CGT TGG GCT GGG CCC 1248

L   P   A   T   H   L   R   H   L   G   E   V   V   429
CTC CCA GCC ACG CAC CTC CGG CAC CTT GGG GAG GTT GTC 1287

H   T   F   S   H   I   K   L   T   Y   Q   V   Y   442
CAC ACC TTC TCT CAC ATC AAG CTG ACA TAT CAA GTA TAT 1326

G   L   A   L   E   G   Q   T   P   V   T   T   V   455
GGG CTG GCC TTG GAA GGG CAG ACC CCA GTG ACC ACC GTA 1365

P   P   G   A   R   W   L   T   Q   E   X   F   H   468
CCA CCA GGT GCT CGC TGG CTG ACG CAG GAG TAA TTT CAC 1404

T   A   A   V   S   T   A   M   K   K   V   F   R   481
ACC GCA GCT GTT TCC ACC GCC ATG AAA AAG GTT TTC CGT 1443

V   Y   Q   G   Q   Q   P   G   T   C   M   G   S   494
GTG TAT CAG GGC CAA CAG CCA GGG ACC TGT ATG GGT TCC 1482

K   R   S   Q   V   S   S   P   C   S   R   K   K   407
AAA AGG TCC CAG GTG TCC TCT CCG TGC AGT CGG AAA AAG 1521

P   R   M   G   Q   Q   V   L   D   N   F   F   R   520
CCC CGC ATG GGC CAG CAA GTC CTG GAT AAT TTC TTT CGG 1560

S   H   I   S   T   D   A   H   S   L   N   S   A   533
TCT CAC ATC TCC ACT GAT GCA CAC AGC CTC AAC AGT GCA 1599

A   Q   *                                           535
GCC CAG TGA                                          1608
```

Y90X Mutant Sequence

Mutant hMYH sequence: 270 C to A (Y90X) mutant. The mutant codon and amino acid indicated in bold and underlined (Single letter amino acid sequence (SEQ ID NO. 4) above and cDNA sequence (SEQ ID NO. 132) below).

```
  M   T   P   L   V   S   R   L   S   R   L   W   A   13
ATG ACA CCG CTC GTC TCC CGC CTG AGT CGT CTG TGG GCC  39

I   M   R   K   P   R   A   A   V   G   S   G   H   26
ATC ATG AGG AAG CCA CGA GCA GCC GTG GGA AGT GGT CAC  78

R   K   Q   A   A   S   Q   E   G   R   Q   K   H   39
AGG AAG CAG GCA GCC AGC CAG GAA GGG AGG CAG AAG CAT 117

A   K   N   N   S   Q   A   K   P   S   A   C   D   52
GCT AAG AAC AAC AGT CAG GCC AAG CCT TCT GCC TGT GAT 156

G   L   R   Q   P   E   E   V   V   L   Q   A       65
GGC CTG GCC AGG CAG CCG GAA GAG GTG GTA TTG CAG GCC 195

S   V   S   S   Y   H   L   F   R   D   V   A   E   78
TCT GTC TCC TCA TAC CAT CTA TTC AGA GAC GTA GCT GAA 234

V   T   A   F   R   G   S   L   L   S   W   X   D   91
GTC ACA GCC TTC CGA GGG AGC CTG CTA AGC TGG TAA GAC 273

Q   E   K   R   D   L   P   W   R   R   A   E      104
CAA GAG AAA CGG GAC CTA CCA TGG AGA AGA CGG GCA GAA 312

D   E   M   D   L   D   R   R   A   Y   A   V   W  117
GAT GAG ATG GAC CTG GAC AGG CGG GCA TAT GCT GTG TGG 351

V   S   E   V   M   L   Q   Q   T   Q   V   A   T  130
GTC TCA GAG GTC ATG CTG CAG CAG ACC CAG GTT GCC ACT 390

V   I   N   Y   Y   T   G   W   M   Q   K   W   P  143
GTG ATC AAC TAC TAT ACC GGA TGG ATG CAG AAG TGG CCT 429

T   L   Q   D   L   A   S   A   S   L   E   E   V  156
ACA CTG CAG GAC CTG GCC AGT GCT TCC CTG GAG GAG GTG 468
```

```
  N   Q   L   W   A   G   L   G   Y   Y   S   R   G    169
AAT CAA CTC TGG GCT GGC CTG GGC TAC TAT TCT CGT GGC    507

R   R   L   Q   E   G   A   R   K   V   V   E   E    182
CGG CGG CTG CAG GAG GGA GCT CGG AAG GTG GTA GAG GAG    546

L   G   G   H   M   P   R   T   A   E   T   L   Q    195
CTA GGG GGC CAC ATG CCA CGT ACA GCA GAG ACC CTG CAG    585

Q   L   L   P   G   V   G   R   Y   T   A   G   A    208
CAG CTC CTG CCT GGC GTG GGG CGC TAC ACA GCT GGG GCC    624

I   A   S   I   A   F   G   Q   A   T   G   V   V    221
ATT GCC TCT ATC GCC TTT GGC CAG GCA ACC GGT GTG GTG    663

D   G   N   V   A   R   V   L   C   R   V   R   A    234
GAT GGC AAC GTA GCA CGG GTG CTG TGC CGT GTC CGA GCC    702

I   G   A   D   P   S   S   T   L   V   S   Q   Q    247
ATT GGT GCT GAT CCC AGC AGC ACC CTT GTT TCC CAG CAG    741

L   W   G   L   A   Q   Q   L   V   D   P   A   R    260
CTC TGG GGT CTA GCC CAG CAG CTG GTG GAC CCA GCC CGG    780

P   G   D   F   N   Q   A   A   M   E   L   G   A    273
CCA GGA GAT TTC AAC CAA GCA GCC ATG GAG CTA GGG GCC    819

T   V   C   T   P   Q   R   P   L   C   S   Q   C    286
ACA GTG TGT ACC CCA CAG CGC CCA CTG TGC AGC CAG TGC    858

P   V   E   S   L   C   R   A   R   Q   R   V   E    299
CCT GTG GAG AGC CTG TGC CGG GCA CGC CAG AGA GTG GAG    897

Q   E   Q   L   L   A   S   G   S   L   S   G   S    312
CAG GAA CAG CTC TTA GCC TCA GGG AGC CTG TCG GGC AGT    936

P   D   V   E   E   C   A   P   N   T   G   Q   C    325
CCT GAC GTG GAG GAG TGT GCT CCC AAC ACT GGA CAG TGC    975

H   L   C   L   P   P   S   E   P   W   D   Q   T    338
CAC CTG TGC CTG CCT CCC TCG GAG CCC TGG GAC CAG ACC   1014

L   G   V   V   N   F   P   R   K   A   S   R   K    351
CTG GGA GTG GTC AAC TTC CCC AGA AAG GCC AGC CGC AAG   1053

P   P   R   E   E   S   S   A   T   C   V   L   E    364
CCC CCC AGG GAG GAG AGC TCT GCC ACC TGT GTT CTG GAA   1092

Q   P   G   A   L   G   A   Q   I   L   L   V   Q    377
CAG CCT GGG GCC CTT GGG GCC CAA ATT CTG CTG GTG CAG   1131

R   P   N   S   G   L   L   A   G   L   W   E   F    390
AGG CCC AAC TCA GGT CTG CTG GCA GGA CTG TGG GAG TTC   1170

P   S   V   T   W   E   P   S   E   Q   L   Q   R    403
CCG TCC GTG ACC TGG GAG CCC TCA GAG CAG CTT CAG CGC   1209

K   A   L   L   Q   E   L   Q   R   W   A   G   P    416
AAG GCC CTG CTG CAG GAA CTA CAG CGT TGG GCT GGG CCC   1248

L   P   A   T   H   L   R   H   L   G   E   V   V    429
CTC CCA GCC ACG CAC CTC CGG CAC CTT GGG GAG GTT GTC   1287

H   T   F   S   H   I   K   L   T   Y   Q   V   Y    422
CAC ACC TTC TCT CAC ATC AAG CTG ACA TAT CAA GTA TAT   1326

G   L   A   L   E   G   Q   T   P   V   T   T   V    455
GGG CTG GCC TTG GAA GGG CAG ACC CCA GTG ACC ACC GTA   1365

P   P   G   A   R   W   L   T   Q   E   E   F   H    468
CCA CCA GGT GCT CGC TGG CTG ACG CAG GAG GAA TTT CAC   1404

T   A   A   V   S   T   A   M   K   K   V   F   R    481
ACC GCA GCT GTT TCC ACC GCC ATG AAA AAG GTT TTC CGT   1443

V   Y   Q   G   Q   Q   P   G   T   C   M   G   S    494
GTG TAT CAG GGC CAA CAG CCA GGG ACC TGT ATG GGT TCC   1482

K   R   S   Q   V   S   S   P   C   S   R   K   K    407
AAA AGG TCC CAG GTG TCC TCT CCG TGC AGT CGG AAA AAG   1521

P   R   M   G   Q   Q   V   L   D   N   F   F   R    520
CCC CGC ATG GGC CAG CAA GTC CTG GAT AAT TTC TTT CGG   1560

S   H   I   S   T   D   A   H   S   L   N   S   A    533
TCT CAC ATC TCC ACT GAT GCA CAC AGC CTC AAC AGT GCA   1599

A   Q   *                                            535
GCC CAG TGA                                           1608
```

What is claimed is:

1. A method for screening a sample for a mutation in an MYH nucleic acid comprising:
   obtaining a sample of an individual;
   analyzing an MYH nucleic acid in said sample; and
   detecting a mutation in said MYH nucleic acid of said sample resulting in the amino acid variant Y165C.

2. The method according to claim 1, wherein said mutation is at position 494.

3. The method according to claim 2, wherein the mutation at position 494 is A→G.

4. The method according to claim 1, wherein said analyzing step comprises amplifying, from said sample, said MYH nucleic acid, or a portion thereof.

5. The method according to claim 4, further comprising sequencing the amplified MYH nucleic acid, or a portion thereof, of the individual.

6. The method according to claim 1, wherein if the individual has said mutation, determining whether the individual is homozygous for said mutation.

7. The method according to claim 1, wherein if the individual has said mutation, determining whether the individual is compound heterozygous for any other mutations.

8. The method according to claim 1, further comprising identifying said individual as having a history of colorectal adenomas or cancer, having at least one family member diagnosed with colorectal cancer, or having an increased risk for colorectal cancer.

9. The method according to claim 8, wherein said identifying step is performed before said detecting step.

10. A method of genotyping, comprising:
   detecting, in a sample of an individual identified as (a) diagnosed with colorectal cancer, (b) diagnosed with colorectal adenomas, (c) having at least one family member diagnosed with colorectal cancer, or (d) at an increased risk for colorectal cancer, that the individual has a nucleotide variant in an MYH nucleic acid of the individual that results in the amino acid variant Y165C.

11. The method according to claim 10, wherein said detecting comprises amplifying, from a sample obtained from the individual, said MYH nucleic acid, or a portion thereof.

12. The method according to claim 1, wherein if the individual has said mutation, determining whether the individual is compound heterozygous for any other mutations.

* * * * *

SEQUENCE LISTING

<160> NUMBER OF SEQ ID NOS: 258

<210> SEQ ID NO 1
<211> LENGTH: 535
<212> TYPE: PRT
<213> ORGANISM: Homo sapiens

<400> SEQUENCE: 1

Met Thr Pro Leu Val Ser Arg Leu Ser Arg Leu Trp Ala Ile Met Arg
1               5                   10                  15

Lys Pro Arg Ala Ala Val Gly Ser Gly His Arg Lys Gln Ala Ala Ser
            20                  25                  30

Gln Glu Gly Arg Gln Lys His Ala Lys Asn Asn Ser Gln Ala Lys Pro
        35                  40                  45

Ser Ala Cys Asp Gly Leu Ala Arg Gln Pro Glu Glu Val Val Leu Gln
    50                  55                  60

Ala Ser Val Ser Ser Tyr His Leu Phe Arg Asp Val Ala Glu Val Thr
65                  70                  75                  80

Ala Phe Arg Gly Ser Leu Leu Ser Trp Tyr Asp Gln Glu Lys Arg Asp
                85                  90                  95

Leu Pro Trp Arg Arg Arg Ala Glu Asp Glu Met Asp Leu Asp Arg Arg
            100                 105                 110

Ala Tyr Ala Val Trp Val Ser Glu Val Met Leu Gln Gln Thr Gln Val
        115                 120                 125

Ala Thr Val Ile Asn Tyr Tyr Thr Gly Trp Met Gln Lys Trp Pro Thr
    130                 135                 140

Leu Gln Asp Leu Ala Ser Ala Ser Leu Glu Glu Val Asn Gln Leu Trp
145                 150                 155                 160

Ala Gly Leu Gly Cys Tyr Ser Arg Gly Arg Arg Leu Gln Glu Gly Ala
                165                 170                 175

Arg Lys Val Val Glu Glu Leu Gly Gly His Met Pro Arg Thr Ala Glu
            180                 185                 190

Thr Leu Gln Gln Leu Leu Pro Gly Val Gly Arg Tyr Thr Ala Gly Ala
        195                 200                 205

Ile Ala Ser Ile Ala Phe Gly Gln Ala Thr Gly Val Val Asp Gly Asn
    210                 215                 220

Val Ala Arg Val Leu Cys Arg Val Arg Ala Ile Gly Ala Asp Pro Ser
225                 230                 235                 240

Ser Thr Leu Val Ser Gln Gln Leu Trp Gly Leu Ala Gln Gln Leu Val
                245                 250                 255

Asp Pro Ala Arg Pro Gly Asp Phe Asn Gln Ala Ala Met Glu Leu Gly
            260                 265                 270

Ala Thr Val Cys Thr Pro Gln Arg Pro Leu Cys Ser Gln Cys Pro Val
        275                 280                 285

Glu Ser Leu Cys Arg Ala Arg Gln Arg Val Glu Gln Glu Gln Leu Leu
    290                 295                 300

Ala Ser Gly Ser Leu Ser Gly Ser Pro Asp Val Glu Glu Cys Ala Pro
305                 310                 315                 320

Asn Thr Gly Gln Cys His Leu Cys Leu Pro Pro Ser Glu Pro Trp Asp
                325                 330                 335

Gln Thr Leu Gly Val Val Asn Phe Pro Arg Lys Ala Ser Arg Lys Pro
            340                 345                 350

Pro Arg Glu Glu Ser Ser Ala Thr Cys Val Leu Glu Gln Pro Gly Ala
        355                 360                 365

```
Leu Gly Ala Gln Ile Leu Leu Val Gln Arg Pro Asn Ser Gly Leu Leu
    370                 375                 380
Ala Gly Leu Trp Glu Phe Pro Ser Val Thr Trp Glu Pro Ser Glu Gln
385                 390                 395                 400
Leu Gln Arg Lys Ala Leu Leu Gln Glu Leu Gln Arg Trp Ala Gly Pro
                405                 410                 415
Leu Pro Ala Thr His Leu Arg His Leu Gly Glu Val Val His Thr Phe
            420                 425                 430
Ser His Ile Lys Leu Thr Tyr Gln Val Tyr Gly Leu Ala Leu Glu Gly
        435                 440                 445
Gln Thr Pro Val Thr Thr Val Pro Pro Gly Ala Arg Trp Leu Thr Gln
    450                 455                 460
Glu Glu Phe His Thr Ala Ala Val Ser Thr Ala Met Lys Lys Val Phe
465                 470                 475                 480
Arg Val Tyr Gln Gly Gln Pro Gly Thr Cys Met Gly Ser Lys Arg
                485                 490                 495
Ser Gln Val Ser Ser Pro Cys Ser Arg Lys Lys Pro Arg Met Gly Gln
                500                 505                 510
Gln Val Leu Asp Asn Phe Phe Arg Ser His Ile Ser Thr Asp Ala His
            515                 520                 525
Ser Leu Asn Ser Ala Ala Gln
            530                 535

<210> SEQ ID NO 2
<211> LENGTH: 7
<212> TYPE: DNA
<213> ORGANISM: Homo sapiens

<400> SEQUENCE: 2 wkaaraa                                                                    7

<210> SEQ ID NO 3
<211> LENGTH: 465
<212> TYPE: PRT
<213> ORGANISM: Homo sapiens

<400> SEQUENCE: 3

Met Thr Pro Leu Val Ser Arg Leu Ser Arg Leu Trp Ala Ile Met Arg
1               5                   10                  15
Lys Pro Arg Ala Ala Val Gly Ser Gly His Arg Lys Gln Ala Ala Ser
                20                  25                  30
Gln Glu Gly Arg Gln Lys His Ala Lys Asn Asn Ser Gln Ala Lys Pro
            35                  40                  45
Ser Ala Cys Asp Gly Leu Ala Arg Gln Pro Glu Glu Val Val Leu Gln
    50                  55                  60
Ala Ser Val Ser Ser Tyr His Leu Phe Arg Asp Val Ala Glu Val Thr
65                  70                  75                  80
Ala Phe Arg Gly Ser Leu Leu Ser Trp Tyr Asp Gln Glu Lys Arg Asp
                85                  90                  95
Leu Pro Trp Arg Arg Arg Ala Glu Asp Glu Met Asp Leu Asp Arg Arg
                100                 105                 110
Ala Tyr Ala Val Trp Val Ser Glu Val Met Leu Gln Gln Thr Gln Val
            115                 120                 125
Ala Thr Val Ile Asn Tyr Tyr Thr Gly Trp Met Gln Lys Trp Pro Thr
    130                 135                 140
```

-continued

```
Leu Gln Asp Leu Ala Ser Ala Ser Leu Glu Glu Val Asn Gln Leu Trp
145                 150                 155                 160

Ala Gly Leu Gly Tyr Tyr Ser Arg Gly Arg Leu Gln Glu Gly Ala
                165                 170                 175

Arg Lys Val Val Glu Glu Leu Gly Gly His Met Pro Arg Thr Ala Glu
            180                 185                 190

Thr Leu Gln Gln Leu Leu Pro Gly Val Gly Arg Tyr Thr Ala Gly Ala
        195                 200                 205

Ile Ala Ser Ile Ala Phe Gly Gln Ala Thr Gly Val Val Asp Gly Asn
    210                 215                 220

Val Ala Arg Val Leu Cys Arg Val Arg Ala Ile Gly Ala Asp Pro Ser
225                 230                 235                 240

Ser Thr Leu Val Ser Gln Gln Leu Trp Gly Leu Ala Gln Gln Leu Val
                245                 250                 255

Asp Pro Ala Arg Pro Gly Asp Phe Asn Gln Ala Ala Met Glu Leu Gly
            260                 265                 270

Ala Thr Val Cys Thr Pro Gln Arg Pro Leu Cys Ser Gln Cys Pro Val
        275                 280                 285

Glu Ser Leu Cys Arg Ala Arg Gln Arg Val Glu Gln Glu Gln Leu Leu
    290                 295                 300

Ala Ser Gly Ser Leu Ser Gly Ser Pro Asp Val Glu Glu Cys Ala Pro
305                 310                 315                 320

Asn Thr Gly Gln Cys His Leu Cys Leu Pro Pro Ser Glu Pro Trp Asp
                325                 330                 335

Gln Thr Leu Gly Val Val Asn Phe Pro Arg Lys Ala Ser Arg Lys Pro
            340                 345                 350

Pro Arg Glu Glu Ser Ser Ala Thr Cys Val Leu Glu Gln Pro Gly Ala
        355                 360                 365

Leu Gly Ala Gln Ile Leu Leu Val Gln Arg Pro Asn Ser Gly Leu Leu
    370                 375                 380

Ala Gly Leu Trp Glu Phe Pro Ser Val Thr Trp Glu Pro Ser Glu Gln
385                 390                 395                 400

Leu Gln Arg Lys Ala Leu Leu Gln Glu Leu Gln Arg Trp Ala Gly Pro
                405                 410                 415

Leu Pro Ala Thr His Leu Arg His Leu Gly Glu Val Val His Thr Phe
            420                 425                 430

Ser His Ile Lys Leu Thr Tyr Gln Val Tyr Gly Leu Ala Leu Glu Gly
        435                 440                 445

Gln Thr Pro Val Thr Thr Val Pro Pro Gly Ala Arg Trp Leu Thr Gln
    450                 455                 460

Glu
465

<210> SEQ ID NO 4
<211> LENGTH: 89
<212> TYPE: PRT
<213> ORGANISM: Homo sapiens

<400> SEQUENCE: 4

Met Thr Pro Leu Val Ser Arg Leu Ser Arg Leu Trp Ala Ile Met Arg
1               5                   10                  15

Lys Pro Arg Ala Ala Val Gly Ser Gly His Arg Lys Gln Ala Ala Ser
            20                  25                  30

Gln Glu Gly Arg Gln Lys His Ala Lys Asn Asn Ser Gln Ala Lys Pro
        35                  40                  45
```

```
Ser Ala Cys Asp Gly Leu Ala Arg Gln Pro Glu Glu Val Val Leu Gln
 50                  55                  60

Ala Ser Val Ser Ser Tyr His Leu Phe Arg Asp Val Ala Glu Val Thr
 65                  70                  75                  80

Ala Phe Arg Gly Ser Leu Leu Ser Trp
             85

<210> SEQ ID NO 5
<211> LENGTH: 23
<212> TYPE: DNA
<213> ORGANISM: Homo sapiens

<400> SEQUENCE: 5
tgcagtcttt attagcattg ttt                                          23

<210> SEQ ID NO 6
<211> LENGTH: 23
<212> TYPE: DNA
<213> ORGANISM: Homo sapiens

<400> SEQUENCE: 6
ttcaaataag ttgtactgcc aag                                          23

<210> SEQ ID NO 7
<211> LENGTH: 25
<212> TYPE: DNA
<213> ORGANISM: Homo sapiens

<400> SEQUENCE: 7
gcaaatccta agagagaaca actgt                                        25

<210> SEQ ID NO 8
<211> LENGTH: 25
<212> TYPE: DNA
<213> ORGANISM: Homo sapiens

<400> SEQUENCE: 8
tccagaacaa aaaccctcta acaag                                        25

<210> SEQ ID NO 9
<211> LENGTH: 20
<212> TYPE: DNA
<213> ORGANISM: Homo sapiens

<400> SEQUENCE: 9
ccttcaatag gcgtgtaatg                                              20

<210> SEQ ID NO 10
<211> LENGTH: 20
<212> TYPE: DNA
<213> ORGANISM: Homo sapiens

<400> SEQUENCE: 10
aaagcagtaa aaccgaacat                                              20

<210> SEQ ID NO 11
<211> LENGTH: 23
<212> TYPE: DNA
<213> ORGANISM: Homo sapiens

<400> SEQUENCE: 11
tcaaatatgg cttccagaac aaa                                          23
```

-continued

```
<210> SEQ ID NO 12
<211> LENGTH: 25
<212> TYPE: DNA
<213> ORGANISM: Homo sapiens

<400> SEQUENCE: 12
gctgatccca gcagcaccct tgttt                                  25

<210> SEQ ID NO 13
<211> LENGTH: 25
<212> TYPE: DNA
<213> ORGANISM: Homo sapiens

<400> SEQUENCE: 13
aatgggggct ttcagaggtg tcact                                  25

<210> SEQ ID NO 14
<211> LENGTH: 22
<212> TYPE: DNA
<213> ORGANISM: Homo sapiens

<400> SEQUENCE: 14
gagggtttgt aaatggaagc ag                                     22

<210> SEQ ID NO 15
<211> LENGTH: 22
<212> TYPE: DNA
<213> ORGANISM: Homo sapiens

<400> SEQUENCE: 15
ctcatgcagc ctttcataga gc                                     22

<210> SEQ ID NO 16
<211> LENGTH: 20
<212> TYPE: DNA
<213> ORGANISM: Homo sapiens

<400> SEQUENCE: 16
gtggtcaact tccccagaaa                                        20

<210> SEQ ID NO 17
<211> LENGTH: 20
<212> TYPE: DNA
<213> ORGANISM: Homo sapiens

<400> SEQUENCE: 17
ggccagccca tatacttgat                                        20

<210> SEQ ID NO 18
<211> LENGTH: 20
<212> TYPE: DNA
<213> ORGANISM: Homo sapiens

<400> SEQUENCE: 18
atggctgcag cttcatatga                                        20

<210> SEQ ID NO 19
<211> LENGTH: 19
<212> TYPE: DNA
<213> ORGANISM: Homo sapiens

<400> SEQUENCE: 19
gctgtcttgg gagctagac                                         19
```

```
<210> SEQ ID NO 20
<211> LENGTH: 19
<212> TYPE: DNA
<213> ORGANISM: Homo sapiens

<400> SEQUENCE: 20
accatgaaac agccagtgt                                                  19

<210> SEQ ID NO 21
<211> LENGTH: 19
<212> TYPE: DNA
<213> ORGANISM: Homo sapiens

<400> SEQUENCE: 21
ctgtggtcct catttgtag                                                  19

<210> SEQ ID NO 22
<211> LENGTH: 20
<212> TYPE: DNA
<213> ORGANISM: Homo sapiens

<400> SEQUENCE: 22
gcaaatccta agagagaaca                                                 20

<210> SEQ ID NO 23
<211> LENGTH: 20
<212> TYPE: DNA
<213> ORGANISM: Homo sapiens

<400> SEQUENCE: 23
gactttgcct tccagagttc                                                 20

<210> SEQ ID NO 24
<211> LENGTH: 21
<212> TYPE: DNA
<213> ORGANISM: Homo sapiens

<400> SEQUENCE: 24
aagctctgct gcccatacac a                                               21

<210> SEQ ID NO 25
<211> LENGTH: 20
<212> TYPE: DNA
<213> ORGANISM: Homo sapiens

<400> SEQUENCE: 25
ctgctatttg cagggtatta                                                 20

<210> SEQ ID NO 26
<211> LENGTH: 20
<212> TYPE: DNA
<213> ORGANISM: Homo sapiens

<400> SEQUENCE: 26
aaagcagtaa aaccgaacat                                                 20

<210> SEQ ID NO 27
<211> LENGTH: 20
<212> TYPE: DNA
<213> ORGANISM: Homo sapiens

<400> SEQUENCE: 27
ttgttggcat ggcagaaata                                                 20
```

```
<210> SEQ ID NO 28
<211> LENGTH: 20
<212> TYPE: DNA
<213> ORGANISM: Homo sapiens

<400> SEQUENCE: 28
ttcttccaga tgctgatact                                               20

<210> SEQ ID NO 29
<211> LENGTH: 20
<212> TYPE: DNA
<213> ORGANISM: Homo sapiens

<400> SEQUENCE: 29
ccttcaatag gcgtgtaatg                                               20

<210> SEQ ID NO 30
<211> LENGTH: 20
<212> TYPE: DNA
<213> ORGANISM: Homo sapiens

<400> SEQUENCE: 30
gcccaaaggg aaaagtcaca                                               20

<210> SEQ ID NO 31
<211> LENGTH: 20
<212> TYPE: DNA
<213> ORGANISM: Homo sapiens

<400> SEQUENCE: 31
atttgcacct tcctgaatag                                               20

<210> SEQ ID NO 32
<211> LENGTH: 19
<212> TYPE: DNA
<213> ORGANISM: Homo sapiens

<400> SEQUENCE: 32
cctgactcac agggagaac                                                19

<210> SEQ ID NO 33
<211> LENGTH: 20
<212> TYPE: DNA
<213> ORGANISM: Homo sapiens

<400> SEQUENCE: 33
ctgtctacct ggagatgtat                                               20

<210> SEQ ID NO 34
<211> LENGTH: 20
<212> TYPE: DNA
<213> ORGANISM: Homo sapiens

<400> SEQUENCE: 34
gcctccaaaa gccctagtga                                               20

<210> SEQ ID NO 35
<211> LENGTH: 21
<212> TYPE: DNA
<213> ORGANISM: Homo sapiens

<400> SEQUENCE: 35
agcacctgag gaaacggtct g                                             21
```

```
<210> SEQ ID NO 36
<211> LENGTH: 20
<212> TYPE: DNA
<213> ORGANISM: Homo sapiens

<400> SEQUENCE: 36
gaaaactccc acctaatctc                                               20

<210> SEQ ID NO 37
<211> LENGTH: 20
<212> TYPE: DNA
<213> ORGANISM: Homo sapiens

<400> SEQUENCE: 37
aacaaaaacc ctctaacaag                                               20

<210> SEQ ID NO 38
<211> LENGTH: 20
<212> TYPE: DNA
<213> ORGANISM: Homo sapiens

<400> SEQUENCE: 38
gcagtaaaac cgaacatatg                                               20

<210> SEQ ID NO 39
<211> LENGTH: 18
<212> TYPE: DNA
<213> ORGANISM: Homo sapiens

<400> SEQUENCE: 39
tggacttttg ggtgtctg                                                 18

<210> SEQ ID NO 40
<211> LENGTH: 20
<212> TYPE: DNA
<213> ORGANISM: Homo sapiens

<400> SEQUENCE: 40
ctaataccct gcaaatagca                                               20

<210> SEQ ID NO 41
<211> LENGTH: 19
<212> TYPE: DNA
<213> ORGANISM: Homo sapiens

<400> SEQUENCE: 41
cgccggccac gagaatggt                                                19

<210> SEQ ID NO 42
<211> LENGTH: 19
<212> TYPE: DNA
<213> ORGANISM: Homo sapiens

<400> SEQUENCE: 42
cgccggccac gagaattgc                                                19

<210> SEQ ID NO 43
<211> LENGTH: 21
<212> TYPE: DNA
<213> ORGANISM: Homo sapiens

<400> SEQUENCE: 43
agtgcttccc tggaggtgag a                                             21
```

```
<210> SEQ ID NO 44
<211> LENGTH: 21
<212> TYPE: DNA
<213> ORGANISM: Homo sapiens

<400> SEQUENCE: 44
cttggttgaa atctcctgcc c                                            21

<210> SEQ ID NO 45
<211> LENGTH: 21
<212> TYPE: DNA
<213> ORGANISM: Homo sapiens

<400> SEQUENCE: 45
cttggttgaa atctcctgac t                                            21

<210> SEQ ID NO 46
<211> LENGTH: 19
<212> TYPE: DNA
<213> ORGANISM: Homo sapiens

<400> SEQUENCE: 46
cgagccattg gtgctgatc                                               19

<210> SEQ ID NO 47
<211> LENGTH: 21
<212> TYPE: DNA
<213> ORGANISM: Homo sapiens

<400> SEQUENCE: 47 gcttttccg actgcacgca g                                             21

<210> SEQ ID NO 48
<211> LENGTH: 21
<212> TYPE: DNA
<213> ORGANISM: Homo sapiens

<400> SEQUENCE: 48 gcttttccg actgcacgaa a                                             21

<210> SEQ ID NO 49
<211> LENGTH: 21
<212> TYPE: DNA
<213> ORGANISM: Homo sapiens

<400> SEQUENCE: 49
gcattccagg ctaagcctag c                                            21

<210> SEQ ID NO 50
<211> LENGTH: 27
<212> TYPE: DNA
<213> ORGANISM: Homo sapiens

<400> SEQUENCE: 50
gcgcgcgcgg gcgcaatagc caagccc                                      27

<210> SEQ ID NO 51
<211> LENGTH: 27
<212> TYPE: DNA
<213> ORGANISM: Homo sapiens

<400> SEQUENCE: 51
ccgccccaca agtcgctcgg cggacgc                                      27
```

-continued

<210> SEQ ID NO 52
<211> LENGTH: 19
<212> TYPE: DNA
<213> ORGANISM: Homo sapiens

<400> SEQUENCE: 52
gaagctgcgg gagctgaaa                                                   19

<210> SEQ ID NO 53
<211> LENGTH: 19
<212> TYPE: DNA
<213> ORGANISM: Homo sapiens

<400> SEQUENCE: 53
atccccgact gcctgaacc                                                   19

<210> SEQ ID NO 54
<211> LENGTH: 20
<212> TYPE: DNA
<213> ORGANISM: Homo sapiens

<400> SEQUENCE: 54
ctgcatttgg ctgggtcttt                                                  20

<210> SEQ ID NO 55
<211> LENGTH: 20
<212> TYPE: DNA
<213> ORGANISM: Homo sapiens

<400> SEQUENCE: 55
cgcacctggc ccttagtaag                                                  20

<210> SEQ ID NO 56
<211> LENGTH: 20
<212> TYPE: DNA
<213> ORGANISM: Homo sapiens

<400> SEQUENCE: 56
agcctgtgca gggatgattg                                                  20

<210> SEQ ID NO 57
<211> LENGTH: 22
<212> TYPE: DNA
<213> ORGANISM: Homo sapiens

<400> SEQUENCE: 57
caaccccaga tgaggagtta gg                                               22

<210> SEQ ID NO 58
<211> LENGTH: 20
<212> TYPE: DNA
<213> ORGANISM: Homo sapiens

<400> SEQUENCE: 58
ctcatctggg gttgcattga                                                  20

<210> SEQ ID NO 59
<211> LENGTH: 20
<212> TYPE: DNA
<213> ORGANISM: Homo sapiens

<400> SEQUENCE: 59
gggttggcat gaggacactg                                                  20

```
<210> SEQ ID NO 60
<211> LENGTH: 18
<212> TYPE: DNA
<213> ORGANISM: Homo sapiens

<400> SEQUENCE: 60
gggcaggtca gcagtgtc                                                   18

<210> SEQ ID NO 61
<211> LENGTH: 20
<212> TYPE: DNA
<213> ORGANISM: Homo sapiens

<400> SEQUENCE: 61
tacacccacc ccaaagtaga                                                 20

<210> SEQ ID NO 62
<211> LENGTH: 20
<212> TYPE: DNA
<213> ORGANISM: Homo sapiens

<400> SEQUENCE: 62
tactttgggg tgggtgtaga                                                 20

<210> SEQ ID NO 63
<211> LENGTH: 20
<212> TYPE: DNA
<213> ORGANISM: Homo sapiens

<400> SEQUENCE: 63
aagagatcac ccgtcagtcc                                                 20

<210> SEQ ID NO 64
<211> LENGTH: 20
<212> TYPE: DNA
<213> ORGANISM: Homo sapiens

<400> SEQUENCE: 64
gggactgacg ggtgatctct                                                 20

<210> SEQ ID NO 65
<211> LENGTH: 22
<212> TYPE: DNA
<213> ORGANISM: Homo sapiens

<400> SEQUENCE: 65
ttggagtgca agactcaaga tt                                              22

<210> SEQ ID NO 66
<211> LENGTH: 20
<212> TYPE: DNA
<213> ORGANISM: Homo sapiens

<400> SEQUENCE: 66
ccaggagtct tgggtgtctt                                                 20

<210> SEQ ID NO 67
<211> LENGTH: 20
<212> TYPE: DNA
<213> ORGANISM: Homo sapiens

<400> SEQUENCE: 67
agaggggcca aagagttagc                                                 20
```

```
<210> SEQ ID NO 68
<211> LENGTH: 20
<212> TYPE: DNA
<213> ORGANISM: Homo sapiens

<400> SEQUENCE: 68
aactctttgg ccectctgtg                                              20

<210> SEQ ID NO 69
<211> LENGTH: 21
<212> TYPE: DNA
<213> ORGANISM: Homo sapiens

<400> SEQUENCE: 69
gaagggaaca ctgctgtgaa g                                            21

<210> SEQ ID NO 70
<211> LENGTH: 19
<212> TYPE: DNA
<213> ORGANISM: Homo sapiens

<400> SEQUENCE: 70
gtgcttcagg ggtgtctgc                                               19

<210> SEQ ID NO 71
<211> LENGTH: 22
<212> TYPE: DNA
<213> ORGANISM: Homo sapiens

<400> SEQUENCE: 71
tgtcataggg cagagtcact cc                                           22

<210> SEQ ID NO 72
<211> LENGTH: 22
<212> TYPE: DNA
<213> ORGANISM: Homo sapiens

<400> SEQUENCE: 72
taaggagtga ctctgcccta tg                                           22

<210> SEQ ID NO 73
<211> LENGTH: 18
<212> TYPE: DNA
<213> ORGANISM: Homo sapiens

<400> SEQUENCE: 73
gccaagaggg gctttagg                                                18

<210> SEQ ID NO 74
<211> LENGTH: 20
<212> TYPE: DNA
<213> ORGANISM: Homo sapiens

<400> SEQUENCE: 74
agcccctctt ggcttgagta                                              20

<210> SEQ ID NO 75
<211> LENGTH: 19
<212> TYPE: DNA
<213> ORGANISM: Homo sapiens

<400> SEQUENCE: 75
tgccgattcc ctccattct                                               19
```

```
<210> SEQ ID NO 76
<211> LENGTH: 20
<212> TYPE: DNA
<213> ORGANISM: Homo sapiens

<400> SEQUENCE: 76
agggcagtgg catgagtaac                                              20

<210> SEQ ID NO 77
<211> LENGTH: 20
<212> TYPE: DNA
<213> ORGANISM: Homo sapiens

<400> SEQUENCE: 77
ggctattccg ctgctcactt                                              20

<210> SEQ ID NO 78
<211> LENGTH: 21
<212> TYPE: DNA
<213> ORGANISM: Homo sapiens

<400> SEQUENCE: 78
ttggcttttg aggctatatc c                                            21

<210> SEQ ID NO 79
<211> LENGTH: 23
<212> TYPE: DNA
<213> ORGANISM: Homo sapiens

<400> SEQUENCE: 79
catgtaggaa acacaaggaa gta                                          23

<210> SEQ ID NO 80
<211> LENGTH: 21
<212> TYPE: DNA
<213> ORGANISM: Homo sapiens

<400> SEQUENCE: 80
tgaagttaag ggcagaacac c                                            21

<210> SEQ ID NO 81
<211> LENGTH: 22
<212> TYPE: DNA
<213> ORGANISM: Homo sapiens

<400> SEQUENCE: 81
gttcacccag acattcgtta gt                                           22

<210> SEQ ID NO 82
<211> LENGTH: 22
<212> TYPE: DNA
<213> ORGANISM: Homo sapiens

<400> SEQUENCE: 82
aggacaagga gaggattctc tg                                           22

<210> SEQ ID NO 83
<211> LENGTH: 18
<212> TYPE: DNA
<213> ORGANISM: Homo sapiens

<400> SEQUENCE: 83
ggaatggggg ctttcaga                                                18
```

-continued

<210> SEQ ID NO 84
<211> LENGTH: 17
<212> TYPE: DNA
<213> ORGANISM: Homo sapiens

<400> SEQUENCE: 84
ctttgggcgt cgacgag                                                  17

<210> SEQ ID NO 85
<211> LENGTH: 19
<212> TYPE: DNA
<213> ORGANISM: Homo sapiens

<400> SEQUENCE: 85
gaggggacag gcttctcag                                                19

<210> SEQ ID NO 86
<211> LENGTH: 20
<212> TYPE: DNA
<213> ORGANISM: Homo sapiens

<400> SEQUENCE: 86
attgagtgcc agggttgtca                                               20

<210> SEQ ID NO 87
<211> LENGTH: 20
<212> TYPE: DNA
<213> ORGANISM: Homo sapiens

<400> SEQUENCE: 87
cggaacccca gtggtgatac                                               20

<210> SEQ ID NO 88
<211> LENGTH: 20
<212> TYPE: DNA
<213> ORGANISM: Homo sapiens

<400> SEQUENCE: 88
tgtactagcg gatcaagtat                                               20

<210> SEQ ID NO 89
<211> LENGTH: 19
<212> TYPE: DNA
<213> ORGANISM: Homo sapiens

<400> SEQUENCE: 89
tggcaaaact gagtcatag                                                19

<210> SEQ ID NO 90
<211> LENGTH: 22
<212> TYPE: DNA
<213> ORGANISM: Homo sapiens

<400> SEQUENCE: 90
gtctggtgtt gctttctcta ac                                            22

<210> SEQ ID NO 91
<211> LENGTH: 17
<212> TYPE: DNA
<213> ORGANISM: Homo sapiens

<400> SEQUENCE: 91
gtgatgcggg cgatgtt                                                  17

-continued

```
<210> SEQ ID NO 92
<211> LENGTH: 19
<212> TYPE: DNA
<213> ORGANISM: Homo sapiens

<400> SEQUENCE: 92
tctccaggtg tgcgactgc                                              19

<210> SEQ ID NO 93
<211> LENGTH: 22
<212> TYPE: DNA
<213> ORGANISM: Homo sapiens

<400> SEQUENCE: 93
aggaagcctt gagaaggtaa cc                                          22

<210> SEQ ID NO 94
<211> LENGTH: 20
<212> TYPE: DNA
<213> ORGANISM: Homo sapiens

<400> SEQUENCE: 94
ggaagaactt gaagatgcct                                             20

<210> SEQ ID NO 95
<211> LENGTH: 18
<212> TYPE: DNA
<213> ORGANISM: Homo sapiens

<400> SEQUENCE: 95
gctcatttcc tgctctcc                                               18

<210> SEQ ID NO 96
<211> LENGTH: 17
<212> TYPE: DNA
<213> ORGANISM: Homo sapiens

<400> SEQUENCE: 96
ccggctttgg ggctata                                                17

<210> SEQ ID NO 97
<211> LENGTH: 20
<212> TYPE: DNA
<213> ORGANISM: Homo sapiens

<400> SEQUENCE: 97
gtttctacca tcccagccca                                             20

<210> SEQ ID NO 98
<211> LENGTH: 20
<212> TYPE: DNA
<213> ORGANISM: Homo sapiens

<400> SEQUENCE: 98
tacttctgtt gatgggtcac                                             20

<210> SEQ ID NO 99
<211> LENGTH: 19
<212> TYPE: DNA
<213> ORGANISM: Homo sapiens

<400> SEQUENCE: 99
tggaggagag gaaacctag                                              19
```

```
<210> SEQ ID NO 100
<211> LENGTH: 20
<212> TYPE: DNA
<213> ORGANISM: Homo sapiens

<400> SEQUENCE: 100
acctcccaac actgtcacta                                               20

<210> SEQ ID NO 101
<211> LENGTH: 17
<212> TYPE: DNA
<213> ORGANISM: Homo sapiens

<400> SEQUENCE: 101
ccctccccaa catgaga                                                  17

<210> SEQ ID NO 102
<211> LENGTH: 20
<212> TYPE: DNA
<213> ORGANISM: Homo sapiens

<400> SEQUENCE: 102
ctgtggccca cgcacttgtg                                               20

<210> SEQ ID NO 103
<211> LENGTH: 22
<212> TYPE: DNA
<213> ORGANISM: Homo sapiens

<400> SEQUENCE: 103
acgtccttgg tccagcagtg gt                                            22

<210> SEQ ID NO 104
<211> LENGTH: 20
<212> TYPE: DNA
<213> ORGANISM: Homo sapiens

<400> SEQUENCE: 104 gagagggat tcacaaggtg                                                20

<210> SEQ ID NO 105
<211> LENGTH: 20
<212> TYPE: DNA
<213> ORGANISM: Homo sapiens

<400> SEQUENCE: 105
gccattagct ccaggcttac                                               20

<210> SEQ ID NO 106
<211> LENGTH: 21
<212> TYPE: DNA
<213> ORGANISM: Homo sapiens

<400> SEQUENCE: 106
gcaaggacag agggctttct g                                             21

<210> SEQ ID NO 107
<211> LENGTH: 20
<212> TYPE: DNA
<213> ORGANISM: Homo sapiens

<400> SEQUENCE: 107
ccagcaggcc atcaactgat                                               20
```

```
<210> SEQ ID NO 108
<211> LENGTH: 19
<212> TYPE: DNA
<213> ORGANISM: Homo sapiens

<400> SEQUENCE: 108
gcacgtcatg gctgactct                                              19

<210> SEQ ID NO 109
<211> LENGTH: 19
<212> TYPE: DNA
<213> ORGANISM: Homo sapiens

<400> SEQUENCE: 109
ctgggaaagc cggttctat                                              19

<210> SEQ ID NO 110
<211> LENGTH: 20
<212> TYPE: DNA
<213> ORGANISM: Homo sapiens

<400> SEQUENCE: 110
tccctgggct gtgtgtagat                                             20

<210> SEQ ID NO 111
<211> LENGTH: 19
<212> TYPE: DNA
<213> ORGANISM: Homo sapiens

<400> SEQUENCE: 111
gagatgggac ccgcatagt                                              19

<210> SEQ ID NO 112
<211> LENGTH: 20
<212> TYPE: DNA
<213> ORGANISM: Homo sapiens

<400> SEQUENCE: 112
tgaagtttgg gttgcacctc                                             20

<210> SEQ ID NO 113
<211> LENGTH: 19
<212> TYPE: DNA
<213> ORGANISM: Homo sapiens

<400> SEQUENCE: 113
agatggtttg cggctgttc                                              19

<210> SEQ ID NO 114
<211> LENGTH: 25
<212> TYPE: DNA
<213> ORGANISM: Homo sapiens

<400> SEQUENCE: 114
gctgatccca gcagcaccct tgttt                                       25

<210> SEQ ID NO 115
<211> LENGTH: 25
<212> TYPE: DNA
<213> ORGANISM: Homo sapiens

<400> SEQUENCE: 115
aatgggggct ttcagaggtg tcact                                       25
```

```
<210> SEQ ID NO 116
<211> LENGTH: 20
<212> TYPE: DNA
<213> ORGANISM: Homo sapiens

<400> SEQUENCE: 116
gtggtcaact tccccagaaa                                                20

<210> SEQ ID NO 117
<211> LENGTH: 20
<212> TYPE: DNA
<213> ORGANISM: Homo sapiens

<400> SEQUENCE: 117
ggccagccca tatacttgat                                                20

<210> SEQ ID NO 118
<211> LENGTH: 19
<212> TYPE: DNA
<213> ORGANISM: Homo sapiens

<400> SEQUENCE: 118
cgccggccac gagaatggt                                                 19

<210> SEQ ID NO 119
<211> LENGTH: 19
<212> TYPE: DNA
<213> ORGANISM: Homo sapiens

<400> SEQUENCE: 119
cgccggccac gagaattgc                                                 19

<210> SEQ ID NO 120
<211> LENGTH: 21
<212> TYPE: DNA
<213> ORGANISM: Homo sapiens

<400> SEQUENCE: 120
agtgcttccc tggaggtgag a                                              21

<210> SEQ ID NO 121
<211> LENGTH: 21
<212> TYPE: DNA
<213> ORGANISM: Homo sapiens

<400> SEQUENCE: 121
cttggttgaa atctcctgcc c                                              21

<210> SEQ ID NO 122
<211> LENGTH: 21
<212> TYPE: DNA
<213> ORGANISM: Homo sapiens

<400> SEQUENCE: 122
cttggttgaa atctcctgac t                                              21

<210> SEQ ID NO 123
<211> LENGTH: 19
<212> TYPE: DNA
<213> ORGANISM: Homo sapiens

<400> SEQUENCE: 123
cgagccattg gtgctgatc                                                 19
```

```
<210> SEQ ID NO 124
<211> LENGTH: 21
<212> TYPE: DNA
<213> ORGANISM: Homo sapiens

<400> SEQUENCE: 124
ccagctccca acactggaga c                                              21

<210> SEQ ID NO 125
<211> LENGTH: 21
<212> TYPE: DNA
<213> ORGANISM: Homo sapiens

<400> SEQUENCE: 125
ccagctccca acactggaga g                                              21

<210> SEQ ID NO 126
<211> LENGTH: 20
<212> TYPE: DNA
<213> ORGANISM: Homo sapiens

<400> SEQUENCE: 126
cccaggctgt tccagaacac                                                20

<210> SEQ ID NO 127
<211> LENGTH: 21
<212> TYPE: DNA
<213> ORGANISM: Homo sapiens

<400> SEQUENCE: 127 gcttttccg actgcacgca g                                               21

<210> SEQ ID NO 128
<211> LENGTH: 21
<212> TYPE: DNA
<213> ORGANISM: Homo sapiens

<400> SEQUENCE: 128 gcttttccg actgcacgaa a                                               21

<210> SEQ ID NO 129
<211> LENGTH: 21
<212> TYPE: DNA
<213> ORGANISM: Homo sapiens

<400> SEQUENCE: 129
gcattccagg ctaagcctag c                                              21

<210> SEQ ID NO 130
<211> LENGTH: 1608
<212> TYPE: DNA
<213> ORGANISM: Homo sapiens

<400> SEQUENCE: 130
atgacaccgc tcgtctcccg cctgagtcgt ctgtgggcca tcatgaggaa gccacgagca     60
gccgtgggaa gtggtcacag gaagcaggca gccagccagg aagggaggca gaagcatgct    120
aagaacaaca gtcaggccaa gccttctgcc tgtgatggcc tggccaggca gccggaagag    180
gtggtattgc aggcctctgt ctcctcatac catctattca gagacgtagc tgaagtcaca    240
gccttccgag ggagcctgct aagctggtac gaccaagaga acgggacct accatggaga    300 agacgggcag aagatgagat ggacctggac aggcgggcat atgctgtgtg ggtctcagag    360
```

| | |
|---|---|
| gtcatgctgc agcagaccca ggttgccact gtgatcaact actataccgg atggatgcag | 420 |
| aagtggccta cactgcagga cctggccagt gcttccctgg aggaggtgaa tcaactctgg | 480 |
| gctggcctgg gctgctattc tcgtggccgg cggctgcagg agggagctcg gaaggtggta | 540 |
| gaggagctag ggggccacat gccacgtaca gcagagaccc tgcagcagct cctgcctggc | 600 |
| gtggggcgct acacagctgg ggccattgcc tctatcgcct ttggccaggc aaccggtgtg | 660 |
| gtggatggca acgtagcacg ggtgctgtgc cgtgtccgag ccattggtgc tgatcccagc | 720 |
| agcacccttg tttcccagca gctctggggt ctagcccagc agctggtgga cccagcccgg | 780 |
| ccaggagatt tcaaccaagc agccatgagc tagggggcca cagtgtgtac cccacagcgc | 840 |
| ccactgtgca gccagtgccc tgtggagagc ctgtgccggg cacgccagag agtggagcag | 900 |
| gaacagctct tagcctcagg gagcctgtcg ggcagtcctg acgtggagga gtgtgctccc | 960 |
| aacactggac agtgccacct gtgcctgcct ccctcggagc cctgggacca gaccctggga | 1020 |
| gtggtcaact tccccagaaa ggccagccgc aagcccccca gggaggagag ctctgccacc | 1080 |
| tgtgttctgg aacagcctgg ggcccttggg gcccaaattc tgctggtgca gaggcccaac | 1140 |
| tcaggtctgc tggcaggact gtgggagttc ccgtccgtga cctgggagcc ctcagagcag | 1200 |
| cttcagcgca aggccctgct gcaggaacta cagcgttggg ctgggcccct cccagccacg | 1260 |
| cacctccggc accttgggga ggttgtccac accttctctc acatcaagct gacatatcaa | 1320 |
| gtatatgggc tggccttgga agggcagacc ccagtgacca ccgtaccacc aggtgctcgc | 1380 |
| tggctgacgc aggaggaatt tcacaccgca gctgtttcca ccgccatgaa aaaggttttc | 1440 |
| cgtgtgtatc agggccaaca gccagggacc tgtatgggtt ccaaaaggtc ccaggtgtcc | 1500 |
| tctccgtgca gtcggaaaaa gccccgcatg gccagcaag tcctggataa tttctttcgg | 1560 |
| tctcacatct ccactgatgc acacagcctc aacagtgcag cccagtga | 1608 |

<210> SEQ ID NO 131
<211> LENGTH: 1608
<212> TYPE: DNA
<213> ORGANISM: Homo sapiens

<400> SEQUENCE: 131

| | |
|---|---|
| atgacaccgc tcgtctcccg cctgagtcgt ctgtgggcca tcatgaggaa gccacgagca | 60 |
| gccgtgggaa gtggtcacag gaagcaggca gccagccagg aagggaggca gaagcatgct | 120 |
| aagaacaaca gtcaggccaa gccttctgcc tgtgatggcc tggccaggca gccggaagag | 180 |
| gtggtattgc aggcctctgt ctcctcatac catctattca gagacgtagc tgaagtcaca | 240 |
| gccttccgag ggagcctgct aagctggtac gaccaagaga acgggaccct accatggaga | 300 |
| agacgggcag aagatgagat ggacctggac aggcgggcat atgctgtgtg ggtctcagag | 360 |
| gtcatgctgc agcagaccca ggttgccact gtgatcaact actataccgg atggatgcag | 420 |
| aagtggccta cactgcagga cctggccagt gcttccctgg aggaggtgaa tcaactctgg | 480 |
| gctggcctgg gctactattc tcgtggccgg cggctgcagg agggagctcg gaaggtggta | 540 |
| gaggagctag ggggccacat gccacgtaca gcagagaccc tgcagcagct cctgcctggc | 600 |
| gtggggcgct acacagctgg ggccattgcc tctatcgcct ttggccaggc aaccggtgtg | 660 |
| gtggatggca acgtagcacg ggtgctgtgc cgtgtccgag ccattggtgc tgatcccagc | 720 |
| agcacccttg tttcccagca gctctggggt ctagcccagc agctggtgga cccagcccgg | 780 |
| ccaggagatt tcaaccaagc agccatgagc tagggggcca cagtgtgtac cccacagcgc | 840 |
| ccactgtgca gccagtgccc tgtggagagc ctgtgccggg cacgccagag agtggagcag | 900 |

| | |
|---|---|
| gaacagctct tagcctcagg gagcctgtcg ggcagtcctg acgtggagga gtgtgctccc | 960 |
| aacactggac agtgccacct gtgcctgcct ccctcggagc cctgggacca gaccctggga | 1020 |
| gtggtcaact tccccagaaa ggccagccgc aagcccccca gggaggagag ctctgccacc | 1080 |
| tgtgttctgg aacagcctgg ggccttggg gcccaaattc tgctggtgca gaggcccaac | 1140 |
| tcaggtctgc tggcaggact gtgggagttc ccgtccgtga cctgggagcc ctcagagcag | 1200 |
| cttcagcgca aggccctgct gcaggaacta cagcgttggg ctgggcccct cccagccacg | 1260 |
| cacctccggc accttgggga ggttgtccac accttctctc acatcaagct gacatatcaa | 1320 |
| gtatatgggc tggccttgga agggcagacc ccagtgacca ccgtaccacc aggtgctcgc | 1380 |
| tggctgacgc aggagtaatt tcacaccgca gctgtttcca ccgccatgaa aaaggttttc | 1440 |
| cgtgtgtatc agggccaaca gccagggacc tgtatgggtt ccaaaaggtc ccaggtgtcc | 1500 |
| tctccgtgca gtcggaaaaa gccccgcatg ggccagcaag tcctggataa tttctttcgg | 1560 |
| tctcacatct ccactgatgc acacagcctc aacagtgcag cccagtga | 1608 |

<210> SEQ ID NO 132
<211> LENGTH: 1608
<212> TYPE: DNA
<213> ORGANISM: Homo sapiens

<400> SEQUENCE: 132

| | |
|---|---|
| atgacaccgc tcgtctcccg cctgagtcgt ctgtgggcca tcatgaggaa gccacgagca | 60 |
| gccgtgggaa gtggtcacag gaagcaggca gccagccagg aagggaggca gaagcatgct | 120 |
| aagaacaaca gtcaggccaa gccttctgcc tgtgatggcc tggccaggca gccggaagag | 180 |
| gtggtattgc aggcctctgt ctcctcatac catctattca gagacgtagc tgaagtcaca | 240 |
| gccttccgag ggagcctgct aagctggtaa gaccaagaga acgggacct accatggaga | 300 |
| agacgggcag aagatgagat ggacctggac aggcgggcat atgctgtgtg gtctcagag | 360 |
| gtcatgctgc agcagaccca ggttgccact gtgatcaact actataccgg atggatgcag | 420 |
| aagtggccta cactgcagga cctggccagt gcttccctgg aggaggtgaa tcaactctgg | 480 |
| gctggcctgg gctactattc tcgtggccgg cggctgcagg agggagctcg gaaggtggta | 540 |
| gaggagctag ggggccacat gccacgtaca gcagagaccc tgcagcagct cctgcctggc | 600 |
| gtggggcgct acacagctgg ggccattgcc tctatcgcct ttggccaggc aaccggtgtg | 660 |
| gtggatggca acgtagcacg ggtgctgtgc cgtgtccgag ccattggtgc tgatcccagc | 720 |
| agcacccttg tttcccagca gctctggggt ctagcccagc agctggtgga cccagcccgg | 780 |
| ccaggagatt tcaaccaagc agccatggag ctaggggcca cagtgtgtac cccacagcgc | 840 |
| ccactgtgca gccagtgccc tgtggagagc ctgtgccggg cacgccagag agtggagcag | 900 |
| gaacagctct tagcctcagg gagcctgtcg ggcagtcctg acgtggagga gtgtgctccc | 960 |
| aacactggac agtgccacct gtgcctgcct ccctcggagc cctgggacca gaccctggga | 1020 |
| gtggtcaact tccccagaaa ggccagccgc aagcccccca gggaggagag ctctgccacc | 1080 |
| tgtgttctgg aacagcctgg ggccttggg gcccaaattc tgctggtgca gaggcccaac | 1140 |
| tcaggtctgc tggcaggact gtgggagttc ccgtccgtga cctgggagcc ctcagagcag | 1200 |
| cttcagcgca aggccctgct gcaggaacta cagcgttggg ctgggcccct cccagccacg | 1260 |
| cacctccggc accttgggga ggttgtccac accttctctc acatcaagct gacatatcaa | 1320 |
| gtatatgggc tggccttgga agggcagacc ccagtgacca ccgtaccacc aggtgctcgc | 1380 |
| tggctgacgc aggaggaatt tcacaccgca gctgtttcca ccgccatgaa aaaggttttc | 1440 |

```
cgtgtgtatc agggccaaca gccagggacc tgtatgggtt ccaaaaggtc ccaggtgtcc    1500
tctccgtgca gtcggaaaaa gccccgcatg ggccagcaag tcctggataa tttctttcgg    1560
tctcacatct ccactgatgc acacagcctc aacagtgcag cccagtga                 1608
```

<210> SEQ ID NO 133
<211> LENGTH: 24
<212> TYPE: DNA
<213> ORGANISM: Homo sapiens

<400> SEQUENCE: 133

```
cttctatcct tttatttgct tgtt                                              24
```

<210> SEQ ID NO 134
<211> LENGTH: 18
<212> TYPE: DNA
<213> ORGANISM: Homo sapiens

<400> SEQUENCE: 134

```
gctaactgcc cccatgtc                                                     18
```

<210> SEQ ID NO 135
<211> LENGTH: 22
<212> TYPE: DNA
<213> ORGANISM: Homo sapiens

<400> SEQUENCE: 135

```
ctaaagacca ggaagcatta tg                                                22
```

<210> SEQ ID NO 136
<211> LENGTH: 19
<212> TYPE: DNA
<213> ORGANISM: Homo sapiens

<400> SEQUENCE: 136

```
atgagatgcc ttgggactt                                                    19
```

<210> SEQ ID NO 137
<211> LENGTH: 24
<212> TYPE: DNA
<213> ORGANISM: Homo sapiens

<400> SEQUENCE: 137

```
attagatgct cagcacttat caga                                              24
```

<210> SEQ ID NO 138
<211> LENGTH: 22
<212> TYPE: DNA
<213> ORGANISM: Homo sapiens

<400> SEQUENCE: 138

```
atgaagagga gctgggtaac ac                                                22
```

<210> SEQ ID NO 139
<211> LENGTH: 22
<212> TYPE: DNA
<213> ORGANISM: Homo sapiens

<400> SEQUENCE: 139

```
tggcaacatg actgtccttt ca                                                22
```

```
<210> SEQ ID NO 140
<211> LENGTH: 22
<212> TYPE: DNA
<213> ORGANISM: Homo sapiens

<400> SEQUENCE: 140
tggctgacac ttcttccatg ac                                              22

<210> SEQ ID NO 141
<211> LENGTH: 22
<212> TYPE: DNA
<213> ORGANISM: Homo sapiens

<400> SEQUENCE: 141
ttcaaagcga ggtttgcaga tc                                              22

<210> SEQ ID NO 142
<211> LENGTH: 22
<212> TYPE: DNA
<213> ORGANISM: Homo sapiens

<400> SEQUENCE: 142
gaatgtgtat gggcagcaga gc                                              22

<210> SEQ ID NO 143
<211> LENGTH: 24
<212> TYPE: DNA
<213> ORGANISM: Homo sapiens

<400> SEQUENCE: 143
cagatgagag aaatgcactt agaa                                            24

<210> SEQ ID NO 144
<211> LENGTH: 21
<212> TYPE: DNA
<213> ORGANISM: Homo sapiens

<400> SEQUENCE: 144
caatcgaggg tttcatttga c                                               21

<210> SEQ ID NO 145
<211> LENGTH: 22
<212> TYPE: DNA
<213> ORGANISM: Homo sapiens

<400> SEQUENCE: 145
tgccttatgc caaattagaa ta                                              22

<210> SEQ ID NO 146
<211> LENGTH: 19
<212> TYPE: DNA
<213> ORGANISM: Homo sapiens

<400> SEQUENCE: 146
cggctgggta ttgaccata                                                  19

<210> SEQ ID NO 147
<211> LENGTH: 22
<212> TYPE: DNA
<213> ORGANISM: Homo sapiens

<400> SEQUENCE: 147
gtcaaatgaa accctcgatt ga                                              22
```

-continued

```
<210> SEQ ID NO 148
<211> LENGTH: 22
<212> TYPE: DNA
<213> ORGANISM: Homo sapiens

<400> SEQUENCE: 148
tttgccttcc agagttcaac tg                                            22

<210> SEQ ID NO 149
<211> LENGTH: 24
<212> TYPE: DNA
<213> ORGANISM: Homo sapiens

<400> SEQUENCE: 149
cctagcccat aaaatacata gtgc                                          24

<210> SEQ ID NO 150
<211> LENGTH: 24
<212> TYPE: DNA
<213> ORGANISM: Homo sapiens

<400> SEQUENCE: 150
ttgtactttg attccttgat tgtc                                          24

<210> SEQ ID NO 151
<211> LENGTH: 22
<212> TYPE: DNA
<213> ORGANISM: Homo sapiens

<400> SEQUENCE: 151
atgggcaaga cccaaacaca ta                                            22

<210> SEQ ID NO 152
<211> LENGTH: 23
<212> TYPE: DNA
<213> ORGANISM: Homo sapiens

<400> SEQUENCE: 152
cccactcgat ttgtttctga acc                                           23

<210> SEQ ID NO 153
<211> LENGTH: 21
<212> TYPE: DNA
<213> ORGANISM: Homo sapiens

<400> SEQUENCE: 153
tgtttctcca tacaggtcac g                                             21

<210> SEQ ID NO 154
<211> LENGTH: 21
<212> TYPE: DNA
<213> ORGANISM: Homo sapiens

<400> SEQUENCE: 154
tcaataggct gatccacatg a                                             21

<210> SEQ ID NO 155
<211> LENGTH: 24
<212> TYPE: DNA
<213> ORGANISM: Homo sapiens

<400> SEQUENCE: 155
ccaattatag tgaacgttac tctg                                          24
```

```
<210> SEQ ID NO 156
<211> LENGTH: 21
<212> TYPE: DNA
<213> ORGANISM: Homo sapiens

<400> SEQUENCE: 156
gatgaaggtg tggacgtatt c                                              21

<210> SEQ ID NO 157
<211> LENGTH: 21
<212> TYPE: DNA
<213> ORGANISM: Homo sapiens

<400> SEQUENCE: 157
caaagcagta aaaccgaaca t                                              21

<210> SEQ ID NO 158
<211> LENGTH: 22
<212> TYPE: DNA
<213> ORGANISM: Homo sapiens

<400> SEQUENCE: 158
cttcctgtgt cgtctgatta ca                                             22

<210> SEQ ID NO 159
<211> LENGTH: 22
<212> TYPE: DNA
<213> ORGANISM: Homo sapiens

<400> SEQUENCE: 159
catctttgtc atcagctgaa ga                                             22

<210> SEQ ID NO 160
<211> LENGTH: 20
<212> TYPE: DNA
<213> ORGANISM: Homo sapiens

<400> SEQUENCE: 160 accactttg gagggagatt                                                 20

<210> SEQ ID NO 161
<211> LENGTH: 20
<212> TYPE: DNA
<213> ORGANISM: Homo sapiens

<400> SEQUENCE: 161
cgaagttcca gcagtgtcac                                                20

<210> SEQ ID NO 162
<211> LENGTH: 19
<212> TYPE: DNA
<213> ORGANISM: Homo sapiens

<400> SEQUENCE: 162
tggcaatcga acgactctc                                                 19

<210> SEQ ID NO 163
<211> LENGTH: 20
<212> TYPE: DNA
<213> ORGANISM: Homo sapiens

<400> SEQUENCE: 163
gttcaggaga ccccactcat                                                20
```

<210> SEQ ID NO 164
<211> LENGTH: 22
<212> TYPE: DNA
<213> ORGANISM: Homo sapiens

<400> SEQUENCE: 164
ctcttttcag cagtaggtgc tt                                              22

<210> SEQ ID NO 165
<211> LENGTH: 21
<212> TYPE: DNA
<213> ORGANISM: Homo sapiens

<400> SEQUENCE: 165
aaccaagcga gaagtaccta a                                               21

<210> SEQ ID NO 166
<211> LENGTH: 21
<212> TYPE: DNA
<213> ORGANISM: Homo sapiens

<400> SEQUENCE: 166
attctgtttc attcccattg t                                               21

<210> SEQ ID NO 167
<211> LENGTH: 20
<212> TYPE: DNA
<213> ORGANISM: Homo sapiens

<400> SEQUENCE: 167
cttgttcatc cagcctgagt                                                 20

<210> SEQ ID NO 168
<211> LENGTH: 19
<212> TYPE: DNA
<213> ORGANISM: Homo sapiens

<400> SEQUENCE: 168
cgtgatgact ttgttggca                                                  19

<210> SEQ ID NO 169
<211> LENGTH: 21
<212> TYPE: DNA
<213> ORGANISM: Homo sapiens

<400> SEQUENCE: 169
gcagcctaaa gaatcaaatg a                                               21

<210> SEQ ID NO 170
<211> LENGTH: 21
<212> TYPE: DNA
<213> ORGANISM: Homo sapiens

<400> SEQUENCE: 170
ggttgcaacc tgttttgtga t                                               21

<210> SEQ ID NO 171
<211> LENGTH: 20
<212> TYPE: DNA
<213> ORGANISM: Homo sapiens

<400> SEQUENCE: 171
tgtggcaagg aaaccaagtc                                                 20

```
<210> SEQ ID NO 172
<211> LENGTH: 23
<212> TYPE: DNA
<213> ORGANISM: Homo sapiens

<400> SEQUENCE: 172
ctgccttctg taggaatggt atc                                           23

<210> SEQ ID NO 173
<211> LENGTH: 20
<212> TYPE: DNA
<213> ORGANISM: Homo sapiens

<400> SEQUENCE: 173
ggaggagcac agtcaggtga                                               20

<210> SEQ ID NO 174
<211> LENGTH: 20
<212> TYPE: DNA
<213> ORGANISM: Homo sapiens

<400> SEQUENCE: 174
gaagacgacg cagatgcttg                                               20

<210> SEQ ID NO 175
<211> LENGTH: 18
<212> TYPE: DNA
<213> ORGANISM: Homo sapiens

<400> SEQUENCE: 175
acaagccttt ccgtgtga                                                 18

<210> SEQ ID NO 176
<211> LENGTH: 23
<212> TYPE: DNA
<213> ORGANISM: Homo sapiens

<400> SEQUENCE: 176
tctttgttgt ctgagaaaac tct                                           23

<210> SEQ ID NO 177
<211> LENGTH: 22
<212> TYPE: DNA
<213> ORGANISM: Homo sapiens

<400> SEQUENCE: 177
aaaagaaacc aacttcacca gt                                            22

<210> SEQ ID NO 178
<211> LENGTH: 21
<212> TYPE: DNA
<213> ORGANISM: Homo sapiens

<400> SEQUENCE: 178
tccttcaata ggcgtgtaat g                                             21

<210> SEQ ID NO 179
<211> LENGTH: 20
<212> TYPE: DNA
<213> ORGANISM: Homo sapiens

<400> SEQUENCE: 179
tttgcttttg attcacctca                                               20
```

```
<210> SEQ ID NO 180
<211> LENGTH: 21
<212> TYPE: DNA
<213> ORGANISM: Homo sapiens

<400> SEQUENCE: 180
gtttaggctg acctcgattt a                                              21

<210> SEQ ID NO 181
<211> LENGTH: 21
<212> TYPE: DNA
<213> ORGANISM: Homo sapiens

<400> SEQUENCE: 181
gaggctaaag ttaccagcca c                                              21

<210> SEQ ID NO 182
<211> LENGTH: 22
<212> TYPE: DNA
<213> ORGANISM: Homo sapiens

<400> SEQUENCE: 182
ttttcttggt caatgtcact ga                                             22

<210> SEQ ID NO 183
<211> LENGTH: 23
<212> TYPE: DNA
<213> ORGANISM: Homo sapiens

<400> SEQUENCE: 183
atactccagt ttgctttct cat                                             23

<210> SEQ ID NO 184
<211> LENGTH: 22
<212> TYPE: DNA
<213> ORGANISM: Homo sapiens

<400> SEQUENCE: 184
aacaggtcat cttcagagtc aa                                             22

<210> SEQ ID NO 185
<211> LENGTH: 21
<212> TYPE: DNA
<213> ORGANISM: Homo sapiens

<400> SEQUENCE: 185
catcaggcta tgctcctaaa t                                              21

<210> SEQ ID NO 186
<211> LENGTH: 21
<212> TYPE: DNA
<213> ORGANISM: Homo sapiens

<400> SEQUENCE: 186
ctgaatcagg ggatagacca t                                              21

<210> SEQ ID NO 187
<211> LENGTH: 21
<212> TYPE: DNA
<213> ORGANISM: Homo sapiens

<400> SEQUENCE: 187
tatgggtggc atattaggtg a                                              21
```

```
<210> SEQ ID NO 188
<211> LENGTH: 20
<212> TYPE: DNA
<213> ORGANISM: Homo sapiens

<400> SEQUENCE: 188
tgaaatggtg atcccagaga                                              20

<210> SEQ ID NO 189
<211> LENGTH: 21
<212> TYPE: DNA
<213> ORGANISM: Homo sapiens

<400> SEQUENCE: 189
agacaagctt cgtctgattc a                                            21

<210> SEQ ID NO 190
<211> LENGTH: 20
<212> TYPE: DNA
<213> ORGANISM: Homo sapiens

<400> SEQUENCE: 190
catttggcct gaaatttctg                                              20

<210> SEQ ID NO 191
<211> LENGTH: 19
<212> TYPE: DNA
<213> ORGANISM: Homo sapiens

<400> SEQUENCE: 191
aggcccacga attctaaaa                                               19

<210> SEQ ID NO 192
<211> LENGTH: 23
<212> TYPE: DNA
<213> ORGANISM: Homo sapiens

<400> SEQUENCE: 192
aggacttgta cttgaggagc tat                                          23

<210> SEQ ID NO 193
<211> LENGTH: 23
<212> TYPE: DNA
<213> ORGANISM: Homo sapiens

<400> SEQUENCE: 193
atgattcata ttccaggagt tcg                                          23

<210> SEQ ID NO 194
<211> LENGTH: 17
<212> TYPE: DNA
<213> ORGANISM: Homo sapiens

<400> SEQUENCE: 194
tggttgctgg gcaggtc                                                 17

<210> SEQ ID NO 195
<211> LENGTH: 22
<212> TYPE: DNA
<213> ORGANISM: Homo sapiens

<400> SEQUENCE: 195
tcaggatcta gagattcgac cc                                           22
```

```
<210> SEQ ID NO 196
<211> LENGTH: 21
<212> TYPE: DNA
<213> ORGANISM: Homo sapiens

<400> SEQUENCE: 196
ggctcatctg tctacctgga g                                       21

<210> SEQ ID NO 197
<211> LENGTH: 22
<212> TYPE: DNA
<213> ORGANISM: Homo sapiens

<400> SEQUENCE: 197
ttcaactaag tcctcaggtt ct                                      22

<210> SEQ ID NO 198
<211> LENGTH: 21
<212> TYPE: DNA
<213> ORGANISM: Homo sapiens

<400> SEQUENCE: 198
tgaaagttga ctggcgtact a                                       21

<210> SEQ ID NO 199
<211> LENGTH: 23
<212> TYPE: DNA
<213> ORGANISM: Homo sapiens

<400> SEQUENCE: 199
caagtggaag tgaatctgat aga                                     23

<210> SEQ ID NO 200
<211> LENGTH: 18
<212> TYPE: DNA
<213> ORGANISM: Homo sapiens

<400> SEQUENCE: 200
atccaccagc ctgaacag                                           18

<210> SEQ ID NO 201
<211> LENGTH: 20
<212> TYPE: DNA
<213> ORGANISM: Homo sapiens

<400> SEQUENCE: 201
taggtcccag gcacaaactc                                         20

<210> SEQ ID NO 202
<211> LENGTH: 20
<212> TYPE: DNA
<213> ORGANISM: Homo sapiens

<400> SEQUENCE: 202
gcttactcga ggaagggatg                                         20

<210> SEQ ID NO 203
<211> LENGTH: 20
<212> TYPE: DNA
<213> ORGANISM: Homo sapiens

<400> SEQUENCE: 203
cgtgagcaca gcaaacattc                                         20
```

```
<210> SEQ ID NO 204
<211> LENGTH: 19
<212> TYPE: DNA
<213> ORGANISM: Homo sapiens

<400> SEQUENCE: 204
cacctgagga aacggtctg                                                  19

<210> SEQ ID NO 205
<211> LENGTH: 21
<212> TYPE: DNA
<213> ORGANISM: Homo sapiens

<400> SEQUENCE: 205
aagtatccgc aaaaggaaca t                                               21

<210> SEQ ID NO 206
<211> LENGTH: 18
<212> TYPE: DNA
<213> ORGANISM: Homo sapiens

<400> SEQUENCE: 206
tcaatcaccg ggggagta                                                   18

<210> SEQ ID NO 207
<211> LENGTH: 23
<212> TYPE: DNA
<213> ORGANISM: Homo sapiens

<400> SEQUENCE: 207
gactgtccca ttaacaatcc tag                                             23

<210> SEQ ID NO 208
<211> LENGTH: 22
<212> TYPE: DNA
<213> ORGANISM: Homo sapiens

<400> SEQUENCE: 208
gtcctggttt tatctcagtt cc                                              22

<210> SEQ ID NO 209
<211> LENGTH: 19
<212> TYPE: DNA
<213> ORGANISM: Homo sapiens

<400> SEQUENCE: 209
cagtgttccc atgcgtacc                                                  19

<210> SEQ ID NO 210
<211> LENGTH: 21
<212> TYPE: DNA
<213> ORGANISM: Homo sapiens

<400> SEQUENCE: 210
tatctgcgct gcttttccta g                                               21

<210> SEQ ID NO 211
<211> LENGTH: 20
<212> TYPE: DNA
<213> ORGANISM: Homo sapiens

<400> SEQUENCE: 211
ctgccagagt gactcctttt                                                 20
```

```
<210> SEQ ID NO 212
<211> LENGTH: 24
<212> TYPE: DNA
<213> ORGANISM: Homo sapiens

<400> SEQUENCE: 212
tcttttaaag tttcatttga aaca                                              24

<210> SEQ ID NO 213
<211> LENGTH: 21
<212> TYPE: DNA
<213> ORGANISM: Homo sapiens

<400> SEQUENCE: 213
aggtctgcgt ttcactaacc t                                                 21

<210> SEQ ID NO 214
<211> LENGTH: 22
<212> TYPE: DNA
<213> ORGANISM: Homo sapiens

<400> SEQUENCE: 214
agccccaatt cagtaactaa ag                                                22

<210> SEQ ID NO 215
<211> LENGTH: 20
<212> TYPE: DNA
<213> ORGANISM: Homo sapiens

<400> SEQUENCE: 215
catctgcttt cttggctgtc                                                   20

<210> SEQ ID NO 216
<211> LENGTH: 21
<212> TYPE: DNA
<213> ORGANISM: Homo sapiens

<400> SEQUENCE: 216
aggattgcct ttaccactca g                                                 21

<210> SEQ ID NO 217
<211> LENGTH: 21
<212> TYPE: DNA
<213> ORGANISM: Homo sapiens

<400> SEQUENCE: 217
gttagtcact ggcagcaaca g                                                 21

<210> SEQ ID NO 218
<211> LENGTH: 23
<212> TYPE: DNA
<213> ORGANISM: Homo sapiens

<400> SEQUENCE: 218
ctcaaaactg cattctgact ttc                                               23

<210> SEQ ID NO 219
<211> LENGTH: 23
<212> TYPE: DNA
<213> ORGANISM: Homo sapiens

<400> SEQUENCE: 219
tgctgaactg tggatagtga gtg                                               23
```

```
<210> SEQ ID NO 220
<211> LENGTH: 21
<212> TYPE: DNA
<213> ORGANISM: Homo sapiens

<400> SEQUENCE: 220
tagtgggatg agcagcatca a                                              21

<210> SEQ ID NO 221
<211> LENGTH: 22
<212> TYPE: DNA
<213> ORGANISM: Homo sapiens

<400> SEQUENCE: 221
gctgctatgt tccctgagac at                                             22

<210> SEQ ID NO 222
<211> LENGTH: 24
<212> TYPE: DNA
<213> ORGANISM: Homo sapiens

<400> SEQUENCE: 222
tgagcattta cttcaaagca gact                                           24

<210> SEQ ID NO 223
<211> LENGTH: 23
<212> TYPE: DNA
<213> ORGANISM: Homo sapiens

<400> SEQUENCE: 223
aggggagtag tttcagaatg tct                                            23

<210> SEQ ID NO 224
<211> LENGTH: 20
<212> TYPE: DNA
<213> ORGANISM: Homo sapiens

<400> SEQUENCE: 224
gggaaaggtt atgcaaggtc                                                20

<210> SEQ ID NO 225
<211> LENGTH: 23
<212> TYPE: DNA
<213> ORGANISM: Homo sapiens

<400> SEQUENCE: 225
agatggtgtc tgctattgta cgt                                            23

<210> SEQ ID NO 226
<211> LENGTH: 23
<212> TYPE: DNA
<213> ORGANISM: Homo sapiens

<400> SEQUENCE: 226
gcctcatcag aaatattgtg agt                                            23

<210> SEQ ID NO 227
<211> LENGTH: 23
<212> TYPE: DNA
<213> ORGANISM: Homo sapiens

<400> SEQUENCE: 227
actcacaata tttctgatga ggc                                            23
```

```
<210> SEQ ID NO 228
<211> LENGTH: 19
<212> TYPE: DNA
<213> ORGANISM: Homo sapiens

<400> SEQUENCE: 228
aggtgtccaa tgctccatg                                                  19

<210> SEQ ID NO 229
<211> LENGTH: 23
<212> TYPE: DNA
<213> ORGANISM: Homo sapiens

<400> SEQUENCE: 229
aaaataggtt ggtaatatgg ctc                                             23

<210> SEQ ID NO 230
<211> LENGTH: 23
<212> TYPE: DNA
<213> ORGANISM: Homo sapiens

<400> SEQUENCE: 230
tgcagatgct atacacaaga ctc                                             23

<210> SEQ ID NO 231
<211> LENGTH: 23
<212> TYPE: DNA
<213> ORGANISM: Homo sapiens

<400> SEQUENCE: 231
aggattgata ggcacttcta gct                                             23

<210> SEQ ID NO 232
<211> LENGTH: 24
<212> TYPE: DNA
<213> ORGANISM: Homo sapiens

<400> SEQUENCE: 232
caagcacata ctcatcttga ctct                                            24

<210> SEQ ID NO 233
<211> LENGTH: 24
<212> TYPE: DNA
<213> ORGANISM: Homo sapiens

<400> SEQUENCE: 233
agagtcaaga tgagtatgtg cttg                                            24

<210> SEQ ID NO 234
<211> LENGTH: 21
<212> TYPE: DNA
<213> ORGANISM: Homo sapiens

<400> SEQUENCE: 234
cagtacgcac aagagcctct a                                               21

<210> SEQ ID NO 235
<211> LENGTH: 23
<212> TYPE: DNA
<213> ORGANISM: Homo sapiens

<400> SEQUENCE: 235
ataagaacaa gatgatggtc tgc                                             23
```

```
<210> SEQ ID NO 236
<211> LENGTH: 23
<212> TYPE: DNA
<213> ORGANISM: Homo sapiens

<400> SEQUENCE: 236
caattctgca acaaaggtaa att                                           23

<210> SEQ ID NO 237
<211> LENGTH: 22
<212> TYPE: DNA
<213> ORGANISM: Homo sapiens

<400> SEQUENCE: 237
gattttgttg agttgtatgc ca                                            22

<210> SEQ ID NO 238
<211> LENGTH: 23
<212> TYPE: DNA
<213> ORGANISM: Homo sapiens

<400> SEQUENCE: 238
ttttagatag ccaggtatca ctg                                           23

<210> SEQ ID NO 239
<211> LENGTH: 18
<212> TYPE: DNA
<213> ORGANISM: Homo sapiens

<400> SEQUENCE: 239
tacggggaac ttcgggta                                                 18

<210> SEQ ID NO 240
<211> LENGTH: 24
<212> TYPE: DNA
<213> ORGANISM: Homo sapiens

<400> SEQUENCE: 240
tggacataaa acctagaaca cttc                                          24

<210> SEQ ID NO 241
<211> LENGTH: 20
<212> TYPE: DNA
<213> ORGANISM: Homo sapiens

<400> SEQUENCE: 241
ggcttgccat gttttagctt                                               20

<210> SEQ ID NO 242
<211> LENGTH: 21
<212> TYPE: DNA
<213> ORGANISM: Homo sapiens

<400> SEQUENCE: 242
acatctgcta aaggctttgg t                                             21

<210> SEQ ID NO 243
<211> LENGTH: 22
<212> TYPE: DNA
<213> ORGANISM: Homo sapiens

<400> SEQUENCE: 243
aagtctcagt ttttcctcaa gg                                            22
```

```
<210> SEQ ID NO 244
<211> LENGTH: 23
<212> TYPE: DNA
<213> ORGANISM: Homo sapiens

<400> SEQUENCE: 244
ccagataaat aactgctcac att                                             23

<210> SEQ ID NO 245
<211> LENGTH: 20
<212> TYPE: DNA
<213> ORGANISM: Homo sapiens

<400> SEQUENCE: 245
ccttgctttg tgcatgttta                                                 20

<210> SEQ ID NO 246
<211> LENGTH: 22
<212> TYPE: DNA
<213> ORGANISM: Homo sapiens

<400> SEQUENCE: 246
tgatctggag ttaatcgaga aa                                              22

<210> SEQ ID NO 247
<211> LENGTH: 22
<212> TYPE: DNA
<213> ORGANISM: Homo sapiens

<400> SEQUENCE: 247
ttttgttgac accctgactc tt                                              22

<210> SEQ ID NO 248
<211> LENGTH: 22
<212> TYPE: DNA
<213> ORGANISM: Homo sapiens

<400> SEQUENCE: 248
aaagtatttt acccaaactg gc                                              22

<210> SEQ ID NO 249
<211> LENGTH: 20
<212> TYPE: DNA
<213> ORGANISM: Homo sapiens

<400> SEQUENCE: 249
cctcttgcag cagccagact                                                 20

<210> SEQ ID NO 250
<211> LENGTH: 23
<212> TYPE: DNA
<213> ORGANISM: Homo sapiens

<400> SEQUENCE: 250
agcagaaagt cagtcccatg aat                                             23

<210> SEQ ID NO 251
<211> LENGTH: 21
<212> TYPE: DNA
<213> ORGANISM: Homo sapiens

<400> SEQUENCE: 251
agcgaaaatt catgggactg a                                               21
```

```
<210> SEQ ID NO 252
<211> LENGTH: 19
<212> TYPE: DNA
<213> ORGANISM: Homo sapiens

<400> SEQUENCE: 252
tccggggaca gcatcaaat                                                19

<210> SEQ ID NO 253
<211> LENGTH: 23
<212> TYPE: DNA
<213> ORGANISM: Homo sapiens

<400> SEQUENCE: 253
ctcttttcac ccatctacag tcc                                           23

<210> SEQ ID NO 254
<211> LENGTH: 20
<212> TYPE: DNA
<213> ORGANISM: Homo sapiens

<400> SEQUENCE: 254
tctgggaagg gacagaagat                                               20

<210> SEQ ID NO 255
<211> LENGTH: 22
<212> TYPE: DNA
<213> ORGANISM: Homo sapiens

<400> SEQUENCE: 255
gttgcttttg atccgtcata aa                                            22

<210> SEQ ID NO 256
<211> LENGTH: 19
<212> TYPE: DNA
<213> ORGANISM: Homo sapiens

<400> SEQUENCE: 256
aggaaggggc tgaggtcac                                                19

<210> SEQ ID NO 257
<211> LENGTH: 23
<212> TYPE: DNA
<213> ORGANISM: Homo sapiens

<400> SEQUENCE: 257
accctctcac tcatgtgatg tca                                           23

<210> SEQ ID NO 258
<211> LENGTH: 22
<212> TYPE: DNA
<213> ORGANISM: Homo sapiens

<400> SEQUENCE: 258
gtgcttctga cgcacaccta tt                                            22
```